United States Patent
Baker et al.

(10) Patent No.: US 6,399,297 B1
(45) Date of Patent: *Jun. 4, 2002

(54) ANTISENSE MODULATION OF EXPRESSION OF TUMOR NECROSIS FACTOR RECEPTOR-ASSOCIATED FACTORS (TRAFS)

(75) Inventors: Brenda F. Baker; Lex M. Cowsert, both of Carlsbad; Brett P. Monia, La Costa, all of CA (US); Xaoxing S. Xu, Maddison, NJ (US)

(73) Assignee: ISIS Pharmaceuticals, Inc., Carlsbad, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/167,109

(22) Filed: Oct. 6, 1998

(51) Int. Cl.$^7$ ............... C07H 21/04; C12Q 1/68; C12N 15/63
(52) U.S. Cl. ............. 435/6; 435/91.1; 435/375; 536/23.1; 536/24.5
(58) Field of Search ............ 514/44; 536/23.1, 536/24.3, 24.5; 435/6, 91.1, 325, 366, 375

(56) References Cited

U.S. PATENT DOCUMENTS 5,789,573 A * 8/1998 Baker et al. ............ 536/24.5

FOREIGN PATENT DOCUMENTS

| JP | WO97/31110 | 2/1997 |
| JP | WO97/38099 | 10/1997 |

OTHER PUBLICATIONS

Min et al., TNF initiates E–selectin transcription in human endothelial cells through parallel TRAF–NF–kB and TRAF–RAC/CDC42–JNK–c–Jun/ATF2 pathways, J. Immunol., vol. 159(7), pp. 3507–3518, Oct. 1996.*

Rojanasakul et al., Antisense oligonucleotidde therapeutics: drug delivery and targeting, Advanced Drug Delivery Reviews, vol. 18, pp. 115–131, 1996.*

Gewirtz et al., Facilitating oligonucleotide delivery: helping antisense deliver on its promise, Proc. Natl. Acad. Sci., vol. 93, pp. 3161–3163, Apr. 1996.*

Branch, A good antisense molecule is hard to find, TIBS, vol. 23, pp. 45–50, Feb. 1998.*

Crooke et al., Basic Principles of Antisense Therapeutics, Antisense Research and Application, pp. 1–50, Jul. 7, 1998.*

Sanghvi, Heterocyclic base modifications in nucleic acids and their applications in antisense oligonucleotides, Antisense Research and Applications, pp. 273–288, 1993.*

Cao, et al., "TRAF6 is a signal transducer for interleukin–1" Nature 1996 93:443–446.

Cheng, et al., "Involvement of CRAF1, a Relative of TRAF, in CD40 Signaling", Science 1995 267, 1494–1498.

Duckett, C.S. and Thompson, C.B., "CD30–dependent degradation of TRAF2: implications for negative regulation of TRAF signaling and the control of cell survival", Genes & Development 1997, 11, 2810–2821.

Ishida, et al., "TRAF5, a novel tumor necrosis factor receptor–associated factor family protein, mediates CD40 signaling", Proc. Natl. Acad. Sci. USA 1996 93, 9437–9442.

Karjewska, et al., "TRAF–4 Expression in Epithelial Progenitor cells Analysis in Normal Adult, Fetal, and Tumor Tissues", Am. J. Of Pathol. 1998 152, 6, 1549–1561.

Malinin et al., "MAP3K–related kinase involved in NF-$_k$B induction by TNF, CD95 and IL–1", Nature 1997 385, 540–544.

Pullen, et al., "CD40–Tumor Necrosis Factor Receptor–Associated Factor (TRAF) Interactions:Regulations of CD40 Signaling through Multiple TRAF Binding Sites and TRAF Hetero–Oligomerization", Biochemistry 1998, 37, 11836–11845.

Rothe, et al., "TRAF2–Mediated Activation of NF-$_k$B by TNF Receptor 2 and CD40", Science 1995 269, 1424–1427.

Rothe, et al., "A Novel Family of Putative Signal Transducers Associated with the Cytoplasmic Domain of the 75 kDA Tumor Necrosis Factor Receptor", Cell 1994 78, 681–692.

Rothe, G. And Baltimore, D., "TANK, a co–inducer with TRAF2 of TNF–and CD40L–mediated NF–kB activation", Genes Dev. 1996 10, 963–973.

Sato, et al., "A novel member of the TRAF family of putative signal transducing proteins binds to the cytosolic domain of CD40", FEBB Lett 1995 358, 113–118.

Speiser, et al., "A Regulatory Role for TRAF1 in Antigen––induced Apoptosis of T Cells", J. Exp. Med 1997 185, 1777–1783.

Takeuchi, et al., "Anatomy of TRAF2", J. Biol. Chem 1996 27, 19935–19942.

Yeh, et al., "Early Lethality, Functional NF-$_k$B Activation, and Increased Sensitivity to TNF–Induced Cell Death in RAF2–Deficient Mice", Immunity 1997, 7, 715–725.

Yuan, J., "Transducing signals of life and death", Curr. Opin. Cell Biol. 1997 9, 247–251.

* cited by examiner

*Primary Examiner*—Andrew Wang
(74) *Attorney, Agent, or Firm*—Licata & Tyrrell P.C.

(57) ABSTRACT

Compositions and methods are provided for modulating the expression of tumor necrosis factor receptor-associated factor (TRAF). Antisense compounds, particularly antisense oligonucleotides, targeted to nucleic acids encoding TRAF are preferred. Methods of using these compounds for modulation of TRAF expression and for treatment of diseases associated with expression of TRAF are provided.

13 Claims, No Drawings

ANTISENSE MODULATION OF EXPRESSION OF TUMOR NECROSIS FACTOR RECEPTOR-ASSOCIATED FACTORS (TRAFS)

FIELD OF THE INVENTION

The present invention provides compositions and methods for modulating the expression of tumor necrosis factor receptor-associated factors (TRAFs). In particular, this invention relates to antisense compounds, particularly oligonucleotides, specifically hybridizable with nucleic acids encoding human TRAFs. Such oligonucleotides have been shown to modulate the expression of TRAFs.

BACKGROUND OF THE INVENTION

Tumor necrosis factor (TNF) receptor superfamily members regulate cellular proliferation,. differentiation and apoptosis in inflammatory and immune responses. This receptor superfamily comprises a group of related cell-surface receptors including, but not limited to, types 1 and 2 TNF receptors (TNFR1 and TNFR2), Fas, CD27, 4-1BB, CD40 and CD30. Signaling through TNF receptor superfamily members is initiated by oligomerization of the receptors with trimeric ligands, bringing intracellular domains in close proximity (Pullen et al., *Biochemistry* 1998, 37, 11836–11845). Two families of adaptor proteins that associate with TNF receptor superfamily members have been identified: the TNF receptor-associated factor (TRAF) family, and the death domain-containing protein family.

Members of the TRAF family of proteins share an amino-terminal RING finger motif and a homologous carboxy-terminal region, referred to in the art as the TRAF domain (Yuan, J., *Curr. Opin. Cell Biol.* 1997, 9, 247–251. This conserved carboxy-terminal region binds to receptor cytoplasmic domains and mediates interactions with the signaling proteins NF-κB inducing kinase (NIK) and I-TRAFT/TANK (Cheng et al., *Science* 1995, 267, 1494–1498; Cheng, G. and Baltimore, D., *Genes Dev.* 1996, 10, 963–973; Rothe et al., *Proc. Natl Acad. Sci. USA* 1996, 93, 8241–8246; Malinin et al., *Nature* 1997, 385, 540–544). A predicted coiled-coil region mediating TRAF homo- and hetero-oligomerization is in a less conserved region N-terminal to the TRAF domain (Cao et al., *Nature* 1996, 383, 443–446; Cheng et al., *Science* 1995, 267, 1494–1498; Rothe et al., *Cell* 1994, 78, 681–692; Sato et al., *FEBS Lett* 1995, 358, 113–118; and Takeuchi et al., *J. Biol. Chem* 1996, 271, 19935–19942).

The mammalian TRAF family currently includes six members, TRAF-1, TRAF-2, TRAF-3, TRAF-4, TRAF-5 and TRAF-6. These proteins have generally been found within the cytosols of cells, either in association with cytosolic vesicles or at the plasma membrane after addition of selected TNF family cytokines to the cells. Members of the TRAF family mediate signals for various different receptors. Subsets of TRAF family members have been shown to interact with the TNF receptor family members (TNFR2, CD40, CD30, LTβR, ATAR, OX40 and 4-1BB).

For example, TRAF-1 and TRAF-2 were identified by their ability to interact with the cytoplasmic domains of TNFR2 (Rothe et al., *Cell* 1994, 78, 681–691). TNFR2 has been associated with TNF's ability to stimulate cell proliferation and activation of NFκB (Tartaglia et al., *Proc. Natl Acad. Sci. USA* 1991, 88, 9292–9296). TRAF-1 is believed to be involved in the regulation of apoptosis (Speiser et al., *J. Exp. Med.* 1997, 185, 1777–1783). Depletion of TRAF-2 and its co-associated proteins has also been shown to increase the sensitivity of the cell to undergo apoptosis during activation of death inducing receptors such as TNFR1 (Duckett, C. S. and Thompson, C. B., *Genes & Development* 1997, 11, 2810–2821; Yeh et al., *Immunity* 1997, 7, 715–725). Accordingly, the rate of receptor-mediated TRAF-2 consumption and TRAF-2 translation has been suggested to play a dynamic role in the regulation of cell survival (Duckett, C. S. and Thompson, C. B., *Genes & Development* 1997, 11, 2810–2821). Targeted disruption of the TRAF-2 gene in mice has also been shown to generate severe defects in c-Jun N-terminal kinase (JNK) activation through TNFR1 (Yeh et al., *Immunity* 1997, 7, 715–725).

TRAF-2 (Rothe et al., *Science* 1995, 269, 1424–1427), TRAF-3 (Cheng et al., *Science* 1995, 267, 1494–1498), TRAF-5 (Ishida et al., *Proc. Natl Acad. Sci USA* 1996, 93, 9437–9442) and TRAF-6 (Pullen et al., *Biochemistry* 1998, 37, 11836–11845) have also been shown to interact with the B lymphocyte receptor CD40. CD40 is a TNF receptor superfamily member that provides activation signals in antigen presenting cells such as B cells, macrophages and dendritic cells. Activation of CD40 leads to B-cell survival, growth and differentiation. In 293T cells, expression of TRAF-3 suppressed constitutive activity of NFκB, whereas expression of TRAF-5 induced NFκB activity. Targeted disruption of the TRAF-3 gene in mice causes impaired immune responses to T-dependent antigens and results in early postnatal lethality (Xu et al., *Immunity* 1996, 5, 407–415). TRAF-2, TRAF-5 or TRAF-6 overexpression in mammalian cells also induces JNK activation.

TRAF-4 is expressed in breast cancers. In in vitro binding assays, TRAF-4 has been shown to interact with the cytosolic domain of the lymphotoxin-β receptor (LTβR) and weakly with the p75 nerve growth factor receptor but not with TNFR1, TNFR2, Fas or CD40 (Karjewska et al., *Am. J. of Pathol.* 1998, 152, 6, 1549–1561).

TRAF-6 has also been reported to mediate the signal transduction pathway induced by IL-1 to activate NFκB by recruiting IL-1 receptor associated kinase (IRAK), a serine/threonine kinase (Cao et al., *Nature* 1996 93:9437–9442). Thus, the role of TRAFs extends beyond being signal transducers for the TNF-receptor superfamily.

The TRAF-5 protein and DNA encoding TRAF-5 are disclosed in WO97/38099. Also disclosed in WO97/38099 is an antisense oligonucleotide against the DNA, an anti-TRAF-5 antibody, a vector containing the DNA, transformants containing this vector and methods of producing TRAF-5 with this vector. In addition, this PCT application discloses methods of screening substances binding to TRAF-5 and substances regulating the activity and expression of this protein.

A TRAF family molecule, a polynucleotide coding for this molecule, an antibody against the molecule and an antisense polynucleotide of the molecule are also disclosed in WO97/31110. Disclosed in this PCT application are the base sequence of the gene and the amino acid of this "unknown" TRAF family molecule, which in addition to the antibody, are suggested to provide means for elucidating the functions of the proteins and the signal transducer system of a TNF-R family in which this molecule participates, to provide probes for research and diagnosis, and to indicate applications for therapeutic agents.

Currently, however, there are no known therapeutic agents which effectively inhibit the synthesis of one or more selected TRAF family members. Consequently, there is a long-felt need for agents capable of effectively inhibiting TRAF expression. Antisense oligonucleotides against one or more TRAFs may therefore prove to be uniquely useful in a number of therapeutic, diagnostic and research applications.

SUMMARY OF THE INVENTION

The present invention is directed to antisense compounds, particularly oligonucleotides, which are targeted to a nucleic acid encoding a selected tumor necrosis factor receptor-associated factor (TRAF), and which modulate the expression of the selected TRAF. Pharmaceutical and other compositions comprising the antisense compounds of the invention are also provided. Further provided are methods of modulating the expression of TRAFs in cells or tissues comprising contacting said cells or tissues with one or more of the antisense compounds or compositions of the invention. Further provided are methods of treating an animal, particularly a human, suspected of having or being prone to a disease or condition associated with expression of a selected TRAF by administering a therapeutically or prophylactically effective amount of one or more of the antisense compounds or compositions of the invention.

DETAILED DESCRIPTION OF THE INVENTION

The present invention employs oligomeric antisense compounds, particularly oligonucleotides, for use in modulating the function of nucleic acid molecules encoding selected tumor necrosis factor receptor-associated factors (TRAFs), ultimately modulating the amount of the selected TRAF produced. This is accomplished by providing antisense compounds which specifically hybridize with one or more nucleic acids encoding the selected TRAF. By "selected TRAF" it is meant any member of the TRAF family of proteins, most preferably TRAF-1, TRAF-2, TRAF-3, TRAF-4, TRAF-5 or TRAF-6. As used herein, the terms "target nucleic acid" and "nucleic acid encoding TRAF" encompass DNA encoding a TRAF family member, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of the selected TRAF. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multi-step process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is one or more nucleic acid molecules encoding one or more selected TRAFs. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding a TRAF, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimens in cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases. Particularly preferred are antisense oligonucleotides comprising from about 8 to about 30 nucleobases (i.e., from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O—(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in U.S. patent application Ser. No. 09/016,520, filed on Jan. 30, 1998, which is commonly owned with the instant application and the contents of which are herein incorporated by reference.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotides. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is incorporated herein by reference.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-Me—C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And*

*Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Crooke, S. T. and Lebleu, B. eds., *Antisense Research and Applications*, CRC Press, Boca Raton, 1993, pp. 289–302. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, U.S. Pat. Nos.: 3,687,808; 4,845,205; 5,130,302; 5,134,066; 5,175,273; 5,367,066; 5,432,272; 5 457,187; 5,459,255; 5,494,908; 5,502,177; 5,525,711; 5,552,540; 5,587,469; 5,594,121; 5,596,091; 5,614,617; 5,681,941; and 5,750,692, each of which is herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al.,*Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-binding Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylaminocarbonyl-oxycholesterol moiety (Crooke et al., *J. Pharmacol. Exp. Ther.*, 1996, 277, 923–937).

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 or in WO 94/26764.

The term "pharmaceutically acceptable salts" refers to physiologically and pharmaceutically acceptable salts of the compounds of the invention: i.e., salts that retain the desired biological activity of the parent compound and do not impart undesired toxicological effects thereto (see, for example, Berge et al., "Pharmaceutical Salts," *J. of Pharma Sci.*, 1977, 66, 1–19).

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of one or more members of the TRAF family is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding one or more selected TRAFs, enabling sandwich and other assays to easily be constructed to exploit this fact. Hybridization of the antisense oligonucleotides of the invention with a nucleic acid encoding one or more TRAFs can be detected by means known in the art. Such means may include conjugation of an enzyme to the oligonucleotide, radiolabelling of the oligonucleotide or any other suitable detection means. Kits using such detection means for detecting the level of TRAF in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; (intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

For example, pharmaceutical compositions and/or formulations comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems*, 1991, 8, 91–192; Muranishi, *Critical Reviews in Therapeutic Drug Carrier Systems*, 1990, 7, 1–33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems*, 1991, 8, 2, 91–192; Muranishi, *Critical Reviews in Thera*- peutic Drug Carrier Systems, 1990, 7, 1, 1–33; El-Hariri et al., J. Pharm. Pharmacol., 1992, 44, 651–654). Examples of some presently preferred fatty acids are sodium caprate and sodium laurate, used singly or in combination at concentrations of 0.5 to 5%.

The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

Regardless of the method by which the antisense compounds of the invention are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layer(s) made up of lipids arranged in a bilayer configuration (see, generally, Chonn et al., Current Op. Biotech., 1995, 6, 698–708).

Liposome preparation is described in pending U.S. patent application Ser. No. 08/961,469, filed on Oct. 31, 1997, which is commonly owned with the instant application and which is herein incorporated by reference.

Certain embodiments of the invention provide for liposomes and other compositions containing (a) one or more antisense compounds and (b) one or more other chemotherapeutic agents which function by a non-antisense mechanism. Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-Alkoxy Amidites 2'-Deoxy and 2'-methoxy beta-cyanoethyldiisopropyl phosphoramidites are purchased from commercial sources (e.g., Chemgenes, Needham, Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides is utilized, except the wait step after pulse delivery of tetrazole and base is increased to 360 seconds.

Oligonucleotides containing 5-methyl-2'-deoxycytidine (5-Me—C) nucleotides were synthesized according to published methods (Sanghvi, et. al., Nucleic Acids Research, 1993, 21, 3197–3203] using commercially available phosphoramidites (Glen Research, Sterling Va. or ChemGenes, Needham, Mass.).

2'-Fluoro Amidites

2'-Fluorodeoxyadenosine Amidites

2'-fluoro oligonucleotides are synthesized as described previously by Kawasaki, et. al., J. Med. Chem., 1993, 36, 831–841 and U.S. Pat. No. 5,670,633, herein incorporated by reference. Briefly, the protected nucleoside N6-benzoyl-2'-deoxy-2'-fluoroadenosine are synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine is selectively protected in moderate yield as the 3',5'-ditetrahydropyranyl (THP) intermediate. Deprotection of the THP and N6-benzoyl groups is accomplished using standard methodologies and standard methods are used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine is accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

2'-Fluorouridine

Synthesis of 2'-deoxy-2'-fluorouridine is accomplished by the modification of a literature procedure in which 2,2'-anhydro-1-beta-D-arabinofuranosyluracil is treated with 70% hydrogen fluoride-pyridine. Standard procedures are used to obtain the 5'-DMT and 5'-DMT-3'phosphoramidites.

2'-Fluorodeoxycytidine

2'-deoxy-2'-fluorocytidine is synthesized via amination of 2'-deoxy-2'-fluorouridine, followed by selective protection to give N4-benzoyl-2'-deoxy-2'-fluorocytidine. Standard procedures are used to obtain the 5'-DMT and 5'-DMT-3'phosphoramidites.

2'-O-(2-Methoxyethyl) Modified Amidites

2'-O-Methoxyethyl-substituted nucleoside amidites were prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum dried in a vacuum oven (60° C. at 1 mm Hg for 24 hours) to give a solid that was crushed to a light tan powder (57 g, 85% crude yield). The NMR spectrum was consistent with the structure, contaminated with phenol as its sodium salt (ca. 5%). The material was used as is for further reactions (or purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/Acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5 methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 hours using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution evaporated. The residue was dissolved in EtOAc (1 L) and the insoluble solids removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH, gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent evaporated to give 85 g (95%) of the title compound.

N4-Benzoyl-2'-O-methoxyethyl-5-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) is added with stirring. The mixture was stirred for 3 hours (tlc showing the reaction to be approximately 95% complete). The solvent was evaporated and the residue azeotroped with MeOH (200 mL). The residue was then dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in CH$_2$Cl$_2$ (1 L) Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (tlc showing the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/Hexane (3:1) as the eluting solvent. The pure fractions were combined to give 90.6 g (87%) of the title compound.

2'-(Aminooxyethyl) Nucleoside Amidites and 2'-(Dimethylaminooxyethyl) Nucleoside Amidites Aminooxyethyl and dimethylaminooxyethyl amidites are prepared as per the methods described in U.S. patent applications Ser. No. 10/037,143, filed Feb. 14, 1998, and Ser. No. 09/016,520, filed Jan. 30, 1998, each of which is herein incorporated by reference.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) were synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 seconds and was followed by the capping step. After cleavage from the CPG column and deblocking in concentrated ammonium hydroxide at 55° C. (18 hours), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O—Me]-[2'-deoxy]-[2'-O—Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5'and 3'wings. The standard synthesis cycle is modified by increasing the wait step after the delivery of tetrazole and base to 600 seconds repeated four times for RNA and twice for 2'-O-methyl. The fully protected oligonucleotide is cleaved from the support and the phosphate group is deprotected in 3:1 Ammonia/Ethanol at room temperature overnight then lyophilized to dryness. Treatment in methanolic ammonia for 24 hours at room temperature is then done to deprotect all bases and sample was again lyophilized to dryness. The pellet is resuspended in 1M TBAF in THF for 24 hours at room temperature to deprotect the 2' positions. The reaction is then quenched with 1 M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides were prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides were purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides are purified by HPLC, as described by Chiang et al., *J. Biol. Chem.* 1991, 266, 18162–18171. Results obtained with HPLC-purified material are similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides were synthesized as per known literature or patented methods. They were utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples were then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR, RNAse protection assay (RPA) or Northern blot analysis. The following four cell types are provided for illustrative purposes, but other cell types can be routinely used.

T-24 Cells:

The transitional cell bladder carcinoma cell line T24 is obtained from the American Type Culture Collection (ATCC) (Manassas, Va.). T-24 cells are routinely cultured in complete McCoy's 5 A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells are routinely passaged by trypsinization and dilution when they reached 90% confluence. Cells are seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 is obtained from the American Type Culture Collection (ATCC) (Manassas, Va.). A549 cells are routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells are routinely passaged by trypsinization and dilution when they reach 90% confluence.

NHDF Cells:

Human neonatal dermal fibroblast (NHDF) are obtained from the Clonetics Corporation (Walkersville Md.). NHDFs are routinely maintained in Fibroblast Growth Medium (Clonetics Corporation, Walkersville, Md.) supplemented as recommended by the supplier. Cells are maintained for up to 10 passages as recommended by the supplier.

HEK Cells:

Human embryonic keratinocytes (HEK) are obtained from the Clonetics Corporation (Walkersville, Md.). HEKs are routinely maintained in Keratinocyte Growth Medium (Clonetics Corporation, Walkersville, Md.) formulated as recommended by the supplier. Cells are routinely maintained for up to 10 passages as recommended by the supplier.

Treatment with Antisense Compounds:

When cells reach 80% confluency, they are treated with oligonucleotide. For cells grown in 96-well plates, wells are washed once with 200 µL OPTI-MEM™-1 reduced-serum medium (Gibco BRL) and then treated with 130 µL of OPTI-MEM™-1 containing 3.75 µg/mL LIPOFECTIN™ (Gibco BRL) and the desired oligonucleotide at a final concentration of 150 nM. After 4 hours of treatment, the medium is replaced with fresh medium. Cells are harvested 16 hours after oligonucleotide treatment.

Example 10

Analysis of Oligonucleotide Inhibition of TRAF Expression

Antisense modulation of TRAF expression can be assayed in a variety of ways known in the art. For example, TRAF mRNA levels can be quantitated by, e.g., Northern blot analysis, RNAse protection assay (RPA), competitive polymerase chain reaction (PCR), or real-time PCR (RT-PCR). RNA analysis can be performed on total cellular RNA or poly(A)+ mRNA. Methods of RNA isolation are taught in, for example, Ausubel, et al., *Current Protocols in Molecular Biology*, Volume 1, John Wiley & Sons, Inc., 1993, pp. 4.1.1–4.2.9 and 4.5.1–4.5.3. Northern blot analysis is routine in the art and is taught in, for example, Ausubel, et al., *Current Protocols in Molecular Biology*, Volume 1, John Wiley & Sons, Inc., 1996, pp. 4.2.1–4.2.9. Real-time quantitative (PCR) can be conveniently accomplished using the commercially available ABI PRISM™ 7700 Sequence Detection System, available from PE-Applied Biosystems, Foster City, Calif. and used according to manufacturer's instructions. Other methods of PCR are also known in the art.

TRAF protein levels can be quantitated in a variety of ways well known in the art, such as immunoprecipitation, Western blot analysis (immunoblotting), ELISA or fluorescence-activated cell sorting (FACS). Antibodies directed to TRAF can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, et al., *Current Protocols in Molecular Biology*, Volume 2, John Wiley & Sons, Inc., 1997, pp. 11.12.1–11.12.9. Preparation of monoclonal antibodies is taught in, for example, Ausubel, et al., *Current Protocols in Molecular Biology*, Volume 2, John Wiley & Sons, Inc., 1997, pp. 11.4.1–11.11.5.

Immunoprecipitation methods are standard in the art and can be found at, for example, Ausubel, et al., *Current Protocols in Molecular Biology*, Volume 2, John Wiley & Sons, Inc., 1998, pp. 11.4.1–11.11.5. Western blot (immunoblot) analysis is standard in the art and can be found at, for example, Ausubel, et al., *Current Protocols in Molecular Biology*, Volume 2, John Wiley & Sons, Inc., 1997, pp. 10.8.1–10.8.21. Enzyme-linked immunosorbent assays (ELISA) are standard in the art and can be found at, for example, Ausubel, et al., *Current Protocols in Molecular Biology*, Volume 2, John Wiley & Sons, Inc., 1991, pp. 11.2.1–11.2.22.

Example 11

Poly(A)+ mRNA Isolation

Poly(A)+ mRNA is isolated according to Miura et al., *Clin. Chem.*, 1996, 42, 1758–1764. Other methods for poly(A)+ mRNA isolation are taught in, for example, Ausubel, et al., *Current Protocols in Molecular Biology*, Volume 1, John Wiley & Sons, Inc., 1993, pp. 4.5.1–4.5.3. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for minutes. 55 µL of lysate is transferred to Oligo d(T) coated 96-well plates (AGCT Inc., Irvine, Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C. is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Example 12

Total RNA Isolation

Total mRNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

Example 13

Real-time Quantitative PCR Analysis of TRAF mRNA Levels

Quantitation of TRAF mRNA levels is determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular (six-second) intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents are obtained from PE-Applied Biosystems, Foster City, Calif. RT-PCR reactions are carried out by adding 25 μL PCR cocktail (1×TAQMAN™ buffer A, 5.5 mM MgCl$_2$, 300 μM each of dATP, dCTP and dGTP, 600 μM of dUTP, 100 nM each of forward primer, reverse primer, and probe, Units RNAse inhibitor, 1.25 Units AMPLITAQ GOLD™, and 12.5 Units MuLV reverse transcriptase) to 96 well plates containing 25 μL poly(A) mRNA solution. The RT reaction is carried out by incubation for 30 minutes at 48° C. Following a 10 minute incubation at 95° C. to activate the AMPLITAQ GOLD™, 40 cycles of a two-step PCR protocol are carried out: 95° C. for 15 seconds (denaturation) followed by 60° C. for 1.5 minutes (annealing/extension). TRAF probes and primers are designed to hybridize to the human TRAF sequence, using published sequence information. For example, GenBank Accession No. U19261, Locus name "HSU 19261" SEQ ID NO: 1; GenBank Accession No. U12597, Locus name "HSU12597" SEQ ID NO. 2; GenBank Accession No U21092, Locus name "HSU21092 SEQ ID NO: 3; GenBank Accession No. X80200, Locus name "HSMLN62" SEQ ID NO. 4; GenBank Accession No. AB000509, Locus name "AB000509 SEQ ID NO. 5; GenBank Accession No. U78798, Locus name "HSU78798" SEQ ID NO. 6.

Example 14

Antisense Inhibition of TRAF-1 Expression-Phosphorothioate Oligodeoxynucleotides In accordance with the present invention, a series of oligonucleotides were designed to target different regions of the human TRAF-1 RNA, using published sequences (GenBank accession number U19261, incorporated herein as SEQ ID NO: 1). The oligonucleotides are shown in Table 1. Target sites are indicated by nucleotide numbers, as given in the sequence source reference (GenBank accession no. U19261), to which the oligonucleotide binds. All compounds in Table 1 are oligodeoxynucleotides with phosphorothioate backbones (internucleoside linkages) throughout.

TABLE 1

Nucleotide Sequences of Human TRAF-1 Phosphorothioate Oligonucleotides

| ISIS NO. | NUCLEOTIDE SEQUENCE[1] (5' → 3') | SEQ ID NO: | TARGET GENE NUCLEO-TIDE COORDI-NATES[2] | GENE TARGET REGION |
|---|---|---|---|---|
| 26698 | TTTAAGTTGCTCCAGGGC | 7 | 0028–0045 | 5'-UTR |
| 26699 | GCCGGGCGAGGACTGCTG | 8 | 0093–0110 | coding |
| 26700 | GCAGACGGTGGGAGGGCA | 9 | 0139–0156 | coding |
| 26701 | CTGGGCTCCTTTGGGTCC | 10 | 0159–0176 | coding |
| 26702 | CACAGCAGAGAGCCCTGG | 11 | 0173–0190 | coding |
| 26703 | ATTCCTCGGGTTCTCAGA | 12 | 0202–0219 | coding |
| 26704 | CCATTCCTCGGGTTCTCA | 13 | 0204–0221 | coding |
| 26705 | CCTCGCCATTCCTCGGGT | 14 | 0209–0226 | coding |
| 26706 | GATCCTCGCCATTCCTCG | 15 | 0212–0229 | coding |
| 26707 | AGACGGCTTCCTGGGCTT | 16 | 0270–0287 | coding |
| 26708 | TTGAAGGAGCAGCCGACA | 17 | 0351–0368 | coding |
| 26709 | GGCCTTCCACTGTTTCAT | 18 | 0442–0459 | coding |
| 26710 | CCACTTCCACGGCTGCCT | 19 | 0527–0544 | coding |
| 26711 | CGCCTGGTGACATTGGTG | 20 | 0894–0911 | coding |
| 26712 | CGCATCATACTCCCCTCT | 21 | 1063–1080 | coding |
| 26713 | AGGCGTCAATGGCGTGCT | 22 | 1142–1159 | coding |
| 26714 | GGAAGGCGTCAATGGCGT | 23 | 1145–1162 | coding |
| 26715 | GGAAGAAGAGTGGGCATC | 24 | 1223–1240 | coding |
| 26716 | CGTAGGCGTGCTTGGGTG | 25 | 1259–1276 | coding |
| 26717 | GCCCCGCCCACCCTAAGT | 26 | 1321–1338 | stop |
| 26718 | GGAGCCCCGCCCACCCTA | 27 | 1324–1341 | stop |
| 26719 | CTCAGGAGCCCCGCCCAC | 28 | 1328–1345 | 3'-UTR |
| 26720 | AAGGGCACGGCATCACAG | 29 | 1380–1397 | 3'-UTR |
| 26721 | TTTGTGCCCTGAGGTCTT | 30 | 1405–1422 | 3'-UTR |
| 26722 | CACCCATCTTTGTCCCCT | 31 | 1413–1430 | 3'-UTR |
| 26723 | GGCCTCCCAGTGTCGCAT | 32 | 1570–1587 | 3'-UTR |
| 26724 | CCCGGTCCTGTTTCTGAC | 33 | 1756–1773 | 3'-UTR |
| 26725 | GCACCCCATCCCTTCCAC | 34 | 1773–1790 | 3'-UTR |
| 26726 | TGGAGCCGTCTGGGTTTG | 35 | 1837–1854 | 3'-UTR |
| 26727 | GTCTTCAAATCCAACCCC | 36 | 1871–1888 | 3'-UTR |
| 26728 | TTCTGGGCTGGAAGGAAA | 37 | 1896–1913 | 3'-UTR |
| 26729 | ACTTTCTGGGCTGGAAGG | 38 | 1899–1916 | 3'-UTR |

TABLE 1-continued

Nucleotide Sequences of Human TRAF-1 Phosphorothioate Oligonucleotides

| ISIS NO. | NUCLEOTIDE SEQUENCE[1] (5' → 3') | SEQ ID NO: | TARGET GENE NUCLEOTIDE COORDINATES[2] | GENE TARGET REGION |
|---|---|---|---|---|
| 26730 | AGAGACTTTCTCCCCTGG | 39 | 1903–1920 | 3'-UTR |
| 26731 | TTTCCAGAACCCCTGTAG | 40 | 1955–1972 | 3'-UTR |
| 26732 | ATCTTTCCAGAACCCCTG | 41 | 1958–1975 | 3'-UTR |
| 26733 | GGGCTGGGTGTGCTCCTG | 42 | 2090–2107 | 3'-UTR |
| 26734 | TTTATGCCCCTCTTCTTC | 43 | 2204–2221 | 3'-UTR |
| 26735 | GGAAAGTTTATGCCCCTC | 44 | 2210–2227 | 3'-UTR |
| 26736 | TACGGGATTCTGGAAAGC | 45 | 2257–2274 | 3'-UTR |
| 26737 | AGGTGTTACGGGATTCTG | 46 | 2263–2280 | 3'-UTR |

[1]All cytidines are 5-methyl-cytidines; all linkages are phosphorothioate linkages.
[2]Coordinates from GenBank Accession No. U19261, locus name "HSU19261" SEQ ID NO.1.

Example 15

Antisense Inhibition of TRAF-1 Expression-Phosphorothioate 2'-MOE Gapmer Oligonucleotides In accordance with the present invention, a second series of oligonucleotides targeted to human TRAF-1 were synthesized. The oligonucleotide sequences are shown in Table 2. Target sites are indicated by nucleotide numbers, as given in the sequence source reference (GenBank accession no. U19261), to which the oligonucleotide binds.

All compounds in Table 2 are chimeric oligonucleotides ("gapmers") 18 nucleotides in length, composed of a central "gap" region consisting of ten 2'-deoxynucleotides, which is flanked on both sides (5' and 3' directions) by four-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

TABLE 2

Nucleotide Sequences of Human TRAF-1 Gapmer Oligonucleotides

| ISIS NO. | NUCLEOTIDE SEQUENCE[1] (5' → 3') | SEQ ID NO: | TARGET GENE NUCLEOTIDE COORDINATES[2] | GENE TARGET REGION |
|---|---|---|---|---|
| 26738 | TTTAAGTTGCTCCAGGGC | 7 | 0028–0045 | 5'-UTR |
| 26739 | GCCGGGCGAGGACTGCTG | 8 | 0093–0110 | coding |
| 26740 | GCAGACGGTGGGAGGGCA | 9 | 0139–0156 | coding |
| 26741 | CTGGGCTCCTTTGGGTCC | 10 | 0159–0176 | coding |
| 26742 | CACAGCAGAGAGCCCTGG | 11 | 0173–0190 | coding |
| 26743 | ATTCCTCGGGTTCTCAGA | 12 | 0202–0219 | coding |
| 26744 | CCATTCCTCGGGTTCTCA | 13 | 0204–0221 | coding |
| 26745 | CCTCGCCATTCCTCGGGT | 14 | 0209–0226 | coding |
| 26746 | GATCCTCGCCATTCCTCG | 15 | 0212–0229 | coding |
| 26747 | AGACGGCTTCCTGGGCTT | 16 | 0270–0287 | coding |
| 26748 | TTGAAGGAGCAGCCGACA | 17 | 0351–0368 | coding |
| 26749 | GGCCTTCCACTGTTTCAT | 18 | 0442–0459 | coding |
| 26750 | CCACTTCCACGGCTGCCT | 19 | 0527–0544 | coding |
| 26751 | CGCCTGGTGACATTGGTG | 20 | 0894–0911 | coding |
| 26752 | CGCATCATACTCCCCTCT | 21 | 1063–1080 | coding |
| 26753 | AGGCGTCAATGGCGTGCT | 22 | 1142–1159 | coding |
| 26754 | GGAAGGCGTCAATGGCGT | 23 | 1145–1162 | coding |
| 26755 | GGAAGAAGAGTGGGCATC | 24 | 1223–1240 | coding |
| 26756 | CGTAGGCGTGCTTGGGTG | 25 | 1259–1276 | coding |
| 26757 | GCCCCGCCCACCCTAAGT | 26 | 1321–1338 | stop |
| 26758 | GGAGCCCCGCCCACCCTA | 27 | 1324–1341 | stop |
| 26759 | CTCAGGAGCCCCGCCCAC | 28 | 1328–1345 | 3'-UTR |
| 26760 | AAGGGCAGGGCATCACAG | 29 | 1380–1397 | 3'-UTR |
| 26761 | TTTGTGCCCTGAGGTCTT | 30 | 1405–1422 | 3'-UTR |
| 26762 | CACCCATCTTTGTGCCCT | 31 | 1413–1430 | 3'-UTR |
| 26763 | GGCCTCCCAGTGTCGCAT | 32 | 1570–1587 | 3'-UTR |
| 26764 | CCCGGTCCTGTTTCTGAC | 33 | 1756–1773 | 3'-UTR |
| 26765 | GCACCCCATCCCTTCCAC | 34 | 1773–1790 | 3'-UTR |
| 26766 | TGGAGCCGTCTGGGTTTG | 35 | 1837–1854 | 3'-UTR |
| 26767 | GTCTTCAAATCCAACCCC | 36 | 1871–1888 | 3'-UTR |
| 26768 | TTCTGGGCTGGAAGGAAA | 37 | 1896–1913 | 3'-UTR |
| 26769 | ACTTTCTGGGCTGGAAGG | 38 | 1899–1916 | 3'-UTR |
| 26770 | AGAGACTTTCTGGGCTGG | 39 | 1903–1920 | 3'-UTR |
| 26771 | TTTCCAGAACCCCTGTAG | 40 | 1955–1972 | 3'-UTR |
| 26772 | ATGTTTCCAGAACCCCTG | 41 | 1958–1975 | 3'-UTR |
| 26773 | GGGCTGGGTGTGCTCCTG | 42 | 2090–2107 | 3'-UTR |
| 26774 | TTTATGCCCCTCTTCTTC | 43 | 2204–2221 | 3'-UTR |
| 26775 | GGAAAGTTTATGCCCCTC | 44 | 2210–2227 | 3'-UTR |
| 26776 | TACGGGATTCTGGAAAGC | 45 | 2257–2274 | 3'-UTR |
| 26777 | AGGTGTTACGGGATTCTG | 46 | 2263–2280 | 3'-UTR |

[1]Emboldened residues are 2'-methoxyethoxy residues (others are 2'-deoxy-). All 2'-methoxyethoxy cytidines and 2'-deoxycytidines are 5-methyl-cytidines; all linkages are phosphorothioate linkages.
[2]Coordinates from GenBank Accession No. 19261, locus name "HSU19261" SEQ ID NO. 1.

Example 16

Antisense Inhibition of TRAF-2 Expression-Phosphorothioate 2'-MOE Gapmer Oligonucleotides In accordance with the present invention, a series of oligonucleotides targeted to human TRAF-2 were synthesized. The oligonucleotide sequences are shown in Table 3. Target sites are indicated by nucleotide numbers, as given in the sequence source reference (GenBank accession no. U12597), to which the oligonucleotide binds.

All compounds in Table 3 are chimeric oligonucleotides ("gapmers") 20 nucleotides in length, composed of a central "gap" region consisting of eight 2'-deoxynucleotides, which is flanked on both sides (5' and 3' directions) by six-nucleotide "wings". The wings are composed of 2'-methoxyethyl (2'-MOE)nucleotides. The internucleoside (backbone) linkages are phosphorothioate (P=S) in the central "deoxy gap" and phosphodiester (P=O) in the wings. Cytidine residues in the 2'-MOE wings are 5-methylcytidines.

TABLE 3

Nucleotide Sequences of TRAF-2 Gapmer Oligonucleotides

| ISIS NO. | NUCLEOTIDE SEQUENCE[1] (5' → 3') | SEQ ID NO: | TARGET GENE NUCLEOTIDE COORDINATES[2] | GENE TARGET REGION |
|---|---|---|---|---|
| 16827 | GoToCoGoCoAsGsCsGsCsGsCsCsGsGoAoAoToToC | 47 | 0001–0020 | 5'-UTR |
| 16828 | CoCoAoAoCoGsGsTsCsGsCsAsGsCsGoCoGoCoCoG | 48 | 0007–0026 | 5'-UTR |
| 16829 | CoAoGoCoCoAsTsGsAsGsAsGsCsTsGoToGoAoCoC | 49 | 0042–0061 | AUG |
| 16830 | AoCoGoCoToAsGsCsTsGsCsAsGsCsCoAoToGoAoG | 50 | 0052–0071 | AUG |
| 16831 | GoCoCoAoCoAsCsTsGsCsGsCsCsTsGoGoAoAoGoG | 51 | 0185–0204 | coding |
| 16832 | CoCoGoGoCoAsGsGsCsTsCsTsCsCsAoCoCoToCoC | 52 | 0348–0367 | coding |
| 16833 | GoCoAoGoCoGsGsCsCsTsTsCsGsTsGoGoCoAoAoC | 53 | 0422–0441 | coding |
| 16834 | CoCoToGoGoTsGsGsTsGsCsGsCsCsToToCoAoCoG | 54 | 0576–0595 | coding |
| 16835 | CoToCoGoAoCsAsCsTsTsGsCsCsAsCoAoAoGoToC | 55 | 0675–0694 | coding |
| 16836 | CoAoCoToGoCsAsCsCsTsCsGsTsGsCoToCoCoToG | 56 | 0751–0770 | coding |
| 16837 | CoCoToCoToGsCsAsGsGsAsGsCsTsCoToGoAoCoC | 57 | 0848–0867 | coding |
| 16838 | CoAoGoCoCoGsGsTsGsCsTsGsCsCsGoGoCoToGoC | 58 | 0962–0981 | coding |
| 16839 | CoCoGoGoToGsCsCsGsTsCsGsCsCsGoToToCoAoG | 59 | 1240–1259 | coding |
| 16840 | AoCoGoToCoGsGsGsCsCsTsGsAsAsGoGoCoGoToC | 60 | 1387–1406 | coding |
| 16841 | CoToGoToCoAsGsGsTsCsCsAsCsAsAoToGoGoCoC | 61 | 1533–1552 | coding |
| 16842 | GoCoCoGoGoCsTsGsTsGsCsCsTsGsGoCoToGoCoC | 62 | 1590–1609 | 3'-UTR |
| 16843 | CoToToGoGoCsTsGsCsAsGsGsCsCsGoAoCoAoCoC | 63 | 1685–1704 | 3'-UTR |
| 16844 | CoGoGoCoCoAsAsTsGsCsCsAsCsCsAoCoAoGoCoC | 64 | 1789–1808 | 3'-UTR |
| 16845 | AoCoToGoToGsCsTsCsCsTsGsCsTsAoCoAoToGoG | 65 | 1916–1935 | 3'-UTR |
| 16846 | GoCoToCoToGsGsCsCsAsGsCsAsGsGoAoGoGoCoC | 66 | 1994–2013 | 3'-UTR |
| 16847 | CoCoAoCoAoGsCsCsAsGsCsCsTsGsGoCoCoAoAoG | 67 | 2117–2136 | 3'-UTR |
| 16848 | CoToCoToGoTsCsTsTsCsGsTsGsAsGoCoToGoGoA | 68 | 2221–2240 | 3'-UTR |
| 26264 | CoCoToCoGoTsGsCsTsGsCsGsGsCsToToCoAoCoG | 69 | mismatch | |
| 26266 | CoCoToGoGoTsGsCsTsCsCsGsGsCsToToCoAoCoG | 70 | mismatch | |
| 27693 | CoCoToCoGsTsGsGsTsGsC̲sGsC̲sC̲sTsToCoAoCoG | 54 | 0576–0595 | coding |
| 27694 | CsCsTsCsGsTsGsGsTsGsC̲sGsC̲sC̲sTsTsCsAsCsG | 54 | 0576–0595 | coding |

[1]Emboldened residues are 2'-methoxyethoxy residues (others are 2'-deoxy). All 2'-methoxyethoxy cytidines are 5-methyl-cytidines, unerlined "C̲" residues are 5-methyl-cytidines; "s" linkages are phosphorothioate linkages, "o" linkages are phosphodiester linkages.
[2]Coordinates from GenBank Accession No. U12597, locus name "HSU12597" SEQ ID NO.2.

HMVEC (human dermal microvascular) cells were purchased from Clonetics (San Diego, Calif.) and cultivated in endothelial basal medium (EBM) supplemented with 10% fetal bovine serum (HyClone, Logan, Utah). Cells were grown in 100 mm petri dishes until 70–80% confluent and then treated with oligonucleotide in the presence of cationic lipid. Briefly, cells were washed with PBS and OPTI-MEM®. OPTI-MEM® containing 10 μg/mL LIPOFECTIN® was added to the cells, followed by addition of oligonucleotide. The cells were incubated for 3–4 hours at 37° C., washed once with EBM/1% FBS, and allowed to recover. For determination of mRNA levels by Northern blot, total RNA was prepared from cells by the guanidinium isothiocyanate procedure or by the Qiagen RNEASY™ method (Qiagen, Valencia, Calif.). Northern blot analysis was performed by standard methods (for example, Ausubel, et al. *Current Protocols in Molecular Biology*, Vol. 1, John Wiley and Sons, Inc., 1996, pp.4.2.1–4.2.9). The probe was a PCR-labeled 1-kb fragment of TRAF-2 amplified by RT-PCR according to the method of Bednarczuk et al., *Biotechniques*, 1991, 10,478. RNA was quantified and normalized to G3 PDH mRNA levels using a Molecular Dynamics (Sunnyvale, Calif.) PhosphorImager in accordance with manufacturer's instructions.

Results are shown in Table 4. Reduction of TRAF-2 mRNA levels with oligonucleotide 16834 (SEQ ID NO. 54) was determined to be dose-dependent in the range of 1 to 100 nM. The $IC_{50}$ was approximately 10 nM. A TRAF-6 antisense oligonucleotide did not affect TRAF-2 mRNA expression.

The effect of oligonucleotide 16834 (SEQ ID NO. 54) on TRAF-2 protein levels was also examined. Cells were treated with oligonucleotide and allowed to recover for 48 to 72 hours before being harvested. Protein levels were determined by western blot analysis. Dose-dependent reduction of TRAF-2 protein expression was detectable 48 hours after treatment and maximal reduction of TRAF-2 protein levels was achieved 72 hours after treatment with 100 nM oligonucleotide.

TABLE 4

Activities of TRAF-2 Gapmer Oligonucleotides

| ISIS No: | SEQ ID NO: | GENE TARGET REGION | % mRNA EXPRESSION | % mRNA INHIBITION |
|---|---|---|---|---|
| LIPOFECTIN only | — | — | 100% | 0% |
| 16827 | 47 | 5'-UTR | 43% | 57% |
| 16828 | 48 | 5'-UTR | 23% | 77% |
| 16829 | 49 | AUG | 48% | 52% |
| 16830 | 50 | AUG | 18% | 82% |
| 16831 | 51 | coding | 49% | 51% |
| 16832 | 52 | coding | 42% | 58% |
| 16833 | 53 | coding | 60% | 40% |
| 16834 | 54 | coding | 3% | 97% |
| 16835 | 55 | coding | 43% | 57% |
| 16836 | 56 | coding | 91% | 9% |
| 16837 | 57 | coding | 60% | 40% |
| 16838 | 58 | coding | 66% | 34% |
| 16839 | 59 | coding | 47% | 53% |
| 16840 | 60 | coding | 45% | 55% |
| 16841 | 61 | coding | 8% | 92% |
| 16842 | 62 | 3'-UTR | 36% | 64% |
| 16843 | 63 | 3'-UTR | 46% | 54% |
| 16844 | 64 | 3'-UTR | 82% | 18% |
| 16845 | 65 | 3'-UTR | 59% | 41% |
| 16846 | 66 | 3'-UTR | 13% | 87% |

TABLE 4-continued

Activities of TRAF-2 Gapmer Oligonucleotides

| ISIS No: | SEQ ID NO: | GENE TARGET REGION | % mRNA EXPRESSION | % mRNA INHIBITION |
|---|---|---|---|---|
| 16847 | 67 | 3'-UTR | 74% | 26% |
| 16848 | 68 | 3'-UTR | 57% | 43% |

ISIS 27693 (SEQ ID NO: 54) was also shown to decrease TRAF-2 mRNA levels in primary human fibroblast-like synoviocytes (obtained from surgical/biopsy specimens). LIPOFECTIN® was included at 3 μg/ml. A dose-response effect was obtained with an $IC_{50}$ of approximately 25 nM and nearly 90% reduction of TRAF-2 mRNA at an oligonucleotide concentration of 100 nM.

Example 17

Antisense Inhibition of TRAF-3 Expression-Phosphorothioate Oligodeoxynucleotides In accordance with the present invention, a series of oligonucleotides were designed to target human TRAF-3 RNA using published sequences (GenBank accession number HSU21092, SEQ ID NO: 3. Oligodeoxynucleotides are shown in Table 5. Target sites are indicated as nucleotide numbers on the TRAF-3 mRNA target (SEQ ID NO: 3).

TABLE 5

Nucleotide Sequences of Human TRAF-3 Phosphorothioate Oligonucleotides

| ISIS NO. | NUCLEOTIDE SEQUENCE[1] (5' → 3') | SEQ ID NO: | TARGET GENE NUCLEOTIDE COORDINATES[2] | GENE TARGET REGION |
|---|---|---|---|---|
| 26778 | AGAGCCGACGACCGCCGC | 71 | 0078–0095 | 5'-UTR |
| 26779 | GGAAGAGCCGACGACCGC | 72 | 0081–0098 | 5'-UTR |
| 26780 | CGCGCCAGGAGAGTCCAT | 73 | 0236–0253 | coding |
| 26781 | TTAGCGGCGGGTTAGTCT | 74 | 0258–0275 | coding |
| 26782 | AGCTTTAGCGGCGGGTTA | 75 | 0262–0279 | coding |
| 26783 | CTCGGTCTGCTTCGGGCT | 76 | 0401–0418 | coding |
| 26784 | TGCCCACACTCGGTCTGC | 77 | 0409–0426 | coding |
| 26785 | CGGTGCCCACACTCGGTC | 78 | 0412–0429 | coding |
| 26786 | GAAGCGGTGCCCACACTC | 79 | 0416–0433 | coding |
| 26787 | TTACACGCCTTCTCCACG | 80 | 0712–0729 | coding |
| 26788 | GTATTTACACGCCTTCTC | 81 | 0716–0733 | coding |
| 26789 | CCGGTATTTACACGCCTT | 82 | 0719–0736 | coding |
| 26790 | GAGGGCAGGACACCACCA | 83 | 0816–0833 | coding |
| 26791 | TGTGAGGGCAGGACACCA | 84 | 0819–0836 | coding |
| 26792 | CACTTGTGAGGGCAGGAC | 85 | 0823–0840 | coding |
| 26793 | GCTGGTTTGTCCCCTGAA | 86 | 0939–0956 | coding |
| 26794 | ATCTGCTGGTTTGTCCCC | 87 | 0943–0960 | coding |
| 26795 | CGCGGTTCTGGAGGGACT | 88 | 1281–1298 | coding |
| 26796 | CCCCGCACTCTTGTCCAC | 89 | 1316–1333 | coding |
| 26797 | TTGCCCCGCACTCTTGTC | 90 | 1319–1336 | coding |
| 26798 | CCACTTGCCCCGCACTCT | 91 | 1323–1340 | coding |
| 26799 | GAGCCACTTGCCCCGCAC | 92 | 1326–1343 | coding |
| 26800 | TTCCGAGCCACTTGCCCC | 93 | 1330–1347 | coding |
| 26801 | TCCGCCGCTTGTAGTCGC | 94 | 1485–1502 | coding |
| 26802 | TGCTTCCGCCGCTTGTAG | 95 | 1489–1506 | coding |
| 26803 | TCCTGCTTCCGCCGCTTG | 96 | 1492–1509 | coding |
| 26804 | GTCCCCGTTCAGGTAGAC | 97 | 1589–1606 | coding |
| 26805 | TCCCGTCCCCGTTCAGGT | 98 | 1593–1610 | coding |
| 26806 | CCATCCCGTCCCCGTTCA | 99 | 1596–1613 | coding |
| 26807 | TCCCCATCCCGTCCCCGT | 100 | 1599–1616 | coding |
| 26808 | CCCTTCCCCATCCCGTCC | 101 | 1603–1620 | coding |
| 26809 | TGCGTCCCCTTCCCCATC | 102 | 1609–1626 | coding |
| 26810 | AAGTGCGTCCCCTTCCCC | 103 | 1612–1629 | coding |
| 26811 | CGACAAGTGCGTCCCCTT | 104 | 1616–1633 | coding |
| 26812 | AAGGAAGCAGGGCATCAT | 105 | 1662–1679 | coding |
| 26813 | CTCTCCAGTGGGCTTCTT | 106 | 1781–1798 | coding |
| 26814 | TCATCTCTCCAGTGGGCT | 107 | 1785–1802 | coding |
| 26815 | GCTAAATCCACCTCCCCA | 108 | 1933–1950 | 3'-UTR |
| 26816 | TCTGCCGCTTCCTCCGTC | 109 | 2027–2044 | 3'-UTR |
| 26817 | CCGCCTTCTGCCGCTTCC | 110 | 2033–2050 | 3'-UTR |

[1]All cytidines are 5-methyl-cytidines; all linkages are phosphorothioate linkages.
[2]Coordinates from GenBank Accession No.U21092, locus name "HSU21092" SEQ ID NO.3.

Example 18

Antisense Inhibition of TRAF-3 Expression-Phosphorothioate 2'-MOE Gapmer Oligonucleotides In accordance with the present invention, a second series of oligonucleotides targeted to human TRAF-3 were synthesized. The oligonucleotide sequences are shown in Table 6. Target sites are indicated by nucleotide numbers, as given in the sequence source reference (GenBank accession no. U21092), to which the oligonucleotide binds.

All compounds in Table 6 are chimeric oligonucleotides ("gapmers") 18 nucleotides in length, composed of a central "gap" region consisting of ten 2'-deoxynucleotides, which is flanked on both sides (5' and 3' directions) by four-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

TABLE 6

Nucleotide Sequences of Human TRAF-3 Gapmer Oligonucleotides

| ISIS NO. | NUCLEOTIDE SEQUENCE[1] (5' → 3') | SEQ ID NO: | TARGET GENE NUCLEOTIDE COORDINATES[2] | GENE TARGET REGION |
|---|---|---|---|---|
| 26818 | AGAGCCGACGACCGCCGC | 71 | 0078–0095 | 5'-UTR |
| 26819 | GGAAGAGCCGACGACCGC | 72 | 0081–0098 | 5'-UTR |
| 26820 | CGCGCCAGGAGAGTCCAT | 73 | 0236–0253 | coding |
| 26821 | TTAGCGGCGGGTTAGTCT | 74 | 0258–0275 | coding |
| 26822 | AGCTTTAGCGGCGGGTTA | 75 | 0262–0279 | coding |
| 26823 | CTCGGTCTGCTTCGGGCT | 76 | 0401–0418 | coding |
| 26824 | TGCCCACACTCGGTCTGC | 77 | 0409–0426 | coding |
| 26825 | CGGTGCCCACACTCGGTC | 78 | 0412–0429 | coding |
| 26826 | GAAGCGGTGCCCACACTC | 79 | 0416–0433 | coding |
| 26827 | TTACACGCCTTCTCCACG | 80 | 0712–0729 | coding |
| 26828 | GTATTTACACGCCTTCTC | 81 | 0716–0733 | coding |
| 26829 | CCGGTATTTACACGCCTT | 82 | 0719–0736 | coding |
| 26830 | GAGGGCAGGACACCACCA | 83 | 0816–0833 | coding |
| 26831 | TGTGAGGGCAGGACACCA | 84 | 0819–0836 | coding |
| 26832 | CACTTGTGAGGGCAGGAC | 85 | 0823–0840 | coding |
| 26833 | GCTGGTTTGTCCCCTGAA | 86 | 0939–0956 | coding |

TABLE 6-continued

Nucleotide Sequences of Human TRAF-3 Gapmer Oligonucleotides

| ISIS NO. | NUCLEOTIDE SEQUENCE[1] (5' → 3') | SEQ ID NO: | TARGET GENE NUCLEOTIDE COORDINATES[2] | GENE TARGET REGION |
|---|---|---|---|---|
| 26834 | ATCTGCTGGTTTGTCCCC | 87 | 0943–0960 | coding |
| 26835 | CGCGGTTCTGGAGGGACT | 88 | 1281–1298 | coding |
| 26836 | CCCCGCACTCTTGTCCAC | 89 | 1316–1333 | coding |
| 26837 | TTGCCCCGCACTCTTGTC | 90 | 1319–1336 | coding |
| 26838 | CCACTTGCCCCGCACTCT | 91 | 1323–1340 | coding |
| 26839 | GAGCCACTTGCCCCGCAC | 92 | 1326–1343 | coding |
| 26840 | TTCCGAGCCACTTGCCCC | 93 | 1330–1347 | coding |
| 26841 | TCCGCCGCTTGTAGTCGC | 94 | 1485–1502 | coding |
| 26842 | TGCTTCCGCCGCTTGTAG | 95 | 1489–1506 | coding |
| 26843 | TCCTGCTTCCGCCGCTTG | 96 | 1492–1509 | coding |
| 26844 | GTCCCCGTTCAGGTAGAC | 97 | 1589–1606 | coding |
| 26845 | TCCCGTCCCCGTTCAGGT | 98 | 1593–1610 | coding |
| 26846 | CCATCCCGTCCCCGTTCA | 99 | 1596–1613 | coding |
| 26847 | TCCCCATCCCGTCCCCGT | 100 | 1599–1616 | coding |
| 26848 | CCCTTCCCCATCCCGTCC | 101 | 1603–1620 | coding |
| 26849 | TGCGTCCCCTTCCCCATC | 102 | 1609–1626 | coding |
| 26850 | AAGTGCGTCCCCTTCCCC | 103 | 1612–1629 | coding |
| 26851 | CGACAAGTGCGTCCCCTT | 104 | 1616–1633 | coding |
| 26852 | AAGGAAGCAGGGCATCAT | 105 | 1662–1679 | coding |
| 26853 | CTCTCCAGTGGGCTTCTT | 106 | 1781–1798 | coding |
| 26854 | TCATCTCTCCAGTGGGCT | 107 | 1785–1802 | coding |
| 26855 | GCTAAATCCACCTCCCCA | 108 | 1933–1950 | 3'-UTR |
| 26856 | TCTGCCGCTTCCTCCGTC | 109 | 2027–2044 | 3'-UTR |
| 26857 | CCGCCTTCTGCCGCTTCC | 110 | 2033–2050 | 3'-UTR |

[1]Emboldened residues are 2'-methoxyethoxy residues (others are 2'-deoxy-). All 2'-methoxyethoxy cytidines and 2'-deoxycytidines are 5-methyl-cytidines; all linkages are phosphorothioate linkages.
[2]Coordinates from GenBank Accession No. U21092, locus name "HSU21092" SEQ ID NO.3.

Example 19

Antisense Inhibition of TRAF-4 Expression-Phosphorothioate Oligodeoxynucleotides In accordance with the present invention, a series of oligonucleotides were designed to target different regions of the human TRAF-4 RNA, using published sequences (GenBank accession number X80200, incorporated herein as SEQ ID NO: 4). The oligonucleotides are shown in Table 7. Target sites are indicated by nucleotide numbers, as given in the sequence source reference (GenBank accession no. X80200), to which the oligonucleotide binds. All compounds in Table 7 oligodeoxynucleotides with phosphorothioate backbones (internucleoside linkages) throughout. The compounds are analyzed for effect on TRAF mRNA levels by quantitative real-time PCR as described in other examples herein.

TABLE 7

Nucleotide Sequences of Human TRAF-4 Phosphorothioate Oligonucleotides

| ISIS NO. | NUCLEOTIDE SEQUENCE[1] (5' → 3') | SEQ ID NO: | TARGET GENE NUCLEOTIDE COORDINATES[2] | GENE TARGET REGION |
|---|---|---|---|---|
| 26860 | GCATGGCGGGCGAGCGGC | 111 | 0072–0089 | AUG |
| 26861 | CCGTCGCTTGGGCTTCTC | 112 | 0113–0130 | coding |
| 26862 | GGGCACTTGAAGACTCCT | 113 | 0232–0249 | coding |
| 26863 | CTCAGGGCACTTGAAGAC | 114 | 0236–0253 | coding |
| 26864 | TGGTCCTCAGGGCACTTG | 115 | 0241–0258 | coding |
| 26865 | AAGCTGGTCCTCAGGGCA | 116 | 0245–0262 | coding |
| 26866 | GCGGCAGCCCTCCTCACT | 117 | 0341–0358 | coding |
| 26867 | CTCCAGCGGCAGCCCTCC | 118 | 0346–0363 | coding |
| 26868 | TAGGGCAGGGAATGACAT | 119 | 0411–0428 | coding |
| 26869 | CGATTAGGGCAGGGAATG | 120 | 0415–0432 | coding |
| 26870 | GGGCAGCGATTAGGGCAG | 121 | 0421–0438 | coding |
| 26871 | GCCTCCCCACTGAAGTCA | 122 | 0523–0540 | coding |
| 26872 | ATGCGGGCACCACACTTA | 123 | 0592–0609 | coding |
| 26873 | GGGCAGGCAACAGGCAGC | 124 | 0733–0750 | coding |
| 26874 | CCACAGTGCCCACACCAC | 125 | 0759–0776 | coding |
| 26875 | CGAGCCACAGTGCCCACA | 126 | 0763–0780 | coding |
| 26876 | TCCTCCCGAGCCACAGTG | 127 | 0769–0786 | coding |
| 26877 | CAGGTCCTCCCGAGCCAC | 128 | 0773–0790 | coding |
| 26878 | GGCAGAGCACCAGGGCGG | 129 | 0819–0836 | coding |
| 26879 | CTTTGAATGGGCAGAGCA | 130 | 0828–0845 | coding |
| 26880 | GGAGTCTTTGAATGGGCA | 131 | 0833–0850 | coding |
| 26881 | ATGCCGTGCCATTGCCAG | 132 | 0875–0892 | coding |
| 26882 | CTCACCAGGGCACACATC | 133 | 0925–0942 | coding |
| 26883 | CAGCTCCTGCCGTTGCCG | 134 | 0944–0961 | coding |
| 26884 | ATGAGCACGCCATCACTG | 135 | 1000–1017 | coding |
| 26885 | TGTAGCCGCCGTCCATAG | 136 | 1033–1050 | coding |
| 26886 | GCCTCCTGTAGCCGCCGT | 137 | 1039–1056 | coding |
| 26887 | TAGAAGGCTGGGCTGAAG | 138 | 1081–1098 | coding |
| 26888 | GTGTGTAGAAGGCTGGGC | 139 | 1086–1103 | coding |
| 26889 | GTGTGCCCTCACCACTGC | 140 | 1152–1169 | coding |
| 26890 | GACACGGCGGGCAAAGGG | 141 | 1226–1243 | coding |
| 26891 | GAAGGTGACACGGCGGGC | 142 | 1232–1249 | coding |
| 26892 | GCCCAGGGTCGCTCTGAT | 143 | 1260–1277 | coding |
| 26893 | CTTCCAGTTTGGGTCGGG | 144 | 1313–1330 | coding |
| 26894 | GATAACCAAAGCCCAGAG | 145 | 1377–1394 | coding |
| 26895 | CATCGTCCTTTCCCCTCG | 146 | 1513–1530 | 3'-UTR |
| 26896 | GGCCAGGGCTGAAGCACC | 147 | 1660–1677 | 3'-UTR |
| 26897 | TTGTTTCCAGCCCTTCAT | 148 | 1703–1720 | 3'-UTR |
| 26898 | CATGTCTGCCCTACCCAA | 149 | 1746–1763 | 3'-UTR |
| 26899 | GCTCCCCTGCTGTGCCCT | 150 | 1948–1965 | 3'-UTR |

[1]All cytidines are 5-methyl-cytidines; all linkages are phosphorothioate linkages.
[2]Coordinates from GenBank Accession No. X80200, locus name "HSMLN62" SEQ ID NO. 4.

Example 20

Antisense Inhibition of TRAF-4 Expression-Phosphorothioate 2'-MOE Gapmer Oligonucleotides In accordance with the present invention, a second series of oligonucleotides targeted to human TRAF-4 were synthesized. The oligonucleotide sequences are shown in Table 8. Target sites are indicated by nucleotide numbers, as given in the sequence source reference (GenBank accession no. X80200), to which the oligonucleotide binds.

All compounds in Table 8 are chimeric oligonucleotides ("gapmers") 18 nucleotides in length, composed of a central "gap" region consisting of ten 2'-deoxynucleotides, which is flanked on both sides (5' and 3' directions) by four-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

Data are obtained by real-time quantitative PCR as described in other examples herein.

TABLE 8

Nucleotide Sequences of Human TRAF-4 Gapmer Oligonucleotides

| ISIS NO. | NUCLEOTIDE SEQUENCE[1] (5' -> 3') | SEQ ID NO: | TARGET GENE NUCLEOTIDE COORDINATES[2] | GENE TARGET REGION |
|---|---|---|---|---|
| 26900 | GCATGGCGGGCGAGCGGC | 111 | 0072–0089 | AUG |
| 26901 | CCGTCGCTTGGGCTTCTC | 112 | 0113–0130 | coding |
| 26902 | GGGCACTTGAAGACTCCT | 113 | 0232–0249 | coding |
| 26903 | CTCAGGGCACTTGAAGAC | 114 | 0236–0253 | coding |
| 26904 | TGGTCCTCAGGGCACTTG | 115 | 0241–0258 | coding |
| 26905 | AAGCTGGTCCTCAGGGCA | 116 | 0245–0262 | coding |
| 26906 | GCGGCAGCCCTCCTCACT | 117 | 0341–0358 | coding |
| 26907 | CTCCAGCGGCAGCCCTCC | 118 | 0346–0363 | coding |
| 26908 | TAGGGCAGGGAATGACAT | 119 | 0411–0428 | coding |
| 26909 | CGATTAGGGCAGGGAATG | 120 | 0415–0432 | coding |
| 26910 | GGGCAGCGATTAGGGCAG | 121 | 0421–0438 | coding |
| 26911 | GCCTCCCCACTGAAGTCA | 122 | 0523–0540 | coding |
| 26912 | ATGCGGGCACCACACTTA | 123 | 0592–0609 | coding |
| 26913 | GGGCAGGCAACAGGCAGC | 124 | 0733–0750 | coding |
| 26914 | CCACAGTGCCCACACCAC | 125 | 0759–0776 | coding |
| 26915 | CGAGCCACAGTGCCCACA | 126 | 0763–0780 | coding |
| 26916 | TCCTCCCGAGCCACAGTG | 127 | 0769–0786 | coding |
| 26917 | CAGGTCCTCCCGAGCCAC | 128 | 0773–0790 | coding |
| 26918 | GGCAGAGCACCAGGGCGG | 129 | 0819–0836 | coding |
| 26919 | CTTTGAATGGGCAGAGCA | 130 | 0828–0845 | coding |
| 26920 | GGAGTCTTTGAATGGGCA | 131 | 0833–0850 | coding |
| 26921 | ATGCCGTGCCATTGCCAG | 132 | 0875–0892 | coding |
| 26922 | CTCACCAGGGCACACATC | 133 | 0925–0942 | coding |
| 26923 | CAGCTCCTGCCGTTGCCG | 134 | 0944–0961 | coding |
| 26924 | ATGAGCACGCCATCACTG | 135 | 1000–1017 | coding |
| 26925 | TGTAGCCGCCGTCCATAG | 136 | 1033–1050 | coding |
| 26926 | GCCTCCTGTAGCCGCCGT | 137 | 1039–1056 | coding |
| 26927 | TAGAAGGCTGGGCTGAAG | 138 | 1081–1098 | coding |
| 26928 | GTGTGTAGAAGGCTGGGC | 139 | 1086–1103 | coding |
| 26929 | GTGTGCCCTCACCACTGC | 140 | 1152–1169 | coding |
| 26930 | GACACGGCGGGCAAAGGG | 141 | 1226–1243 | coding |
| 26931 | GAAGGTGACACGGCGGGC | 142 | 1232–1249 | coding |
| 26932 | GCCCAGGGTCGCTCTGAT | 143 | 1260–1277 | coding |
| 26933 | CTTCCAGTTTGGGTCGGG | 144 | 1313–1330 | coding |
| 26934 | GATAACCAAAGCCCAGAG | 145 | 1377–1394 | coding |
| 26935 | CATCGTCCTTTCCCCTCG | 146 | 1513–1530 | 3'-UTR |
| 26936 | GGCCAGGGCTGAAGCACC | 147 | 1660–1677 | 3'-UTR |
| 26937 | TTGTTTCCAGCCCTTCAT | 148 | 1703–1720 | 3'-UTR |
| 26938 | CATGTCTGCCCTACCCAA | 149 | 1746–1763 | 3'-UTR |
| 26939 | GCTCCCCTGCTGTGCCCT | 150 | 1948–1965 | 3'-UTR |

[1]Emboldened residues are 2'-methoxyethoxy residues (others are 2'-deoxy-). All 2'-methoxyethoxy cytidines and 2'-deoxycytidines are 5-methyl-cytidines; all linkages are phosphorothioate linkages.
[2]Coordinates from GenBank Accession No. X80200, locus name "HSMLN62" SEQ ID NO. 4.

Example 21

Antisense Inhibition of TRAF-5 Expression- Phosphorothioate Oligodeoxynucleotides In accordance with the present invention, a series of oligonucleotides were designed to target different regions of the human TRAF-5 RNA, using published sequences (GenBank accession number AB000509, incorporated herein as SEQ ID NO: 5). The oligonucleotides are shown in Table 9. Target sites are indicated by nucleotide numbers, as given in the sequence source reference (GenBank accession no. AB000509), to which the oligonucleotide binds. All compounds in Table 9 are oligodeoxynucleotides with phosphorothioate backbones (internucleoside linkages) throughout.

TABLE 9

Nucleotide Sequences of Human TRAF-5 Phosphorothioate Oligonucleotides

| ISIS NO. | NUCLEOTIDE SEQUENCE[1] (5' -> 3') | SEQ ID NO: | TARGET GENE NUCLEOTIDE COORDINATES[2] | GENE TARGET REGION |
|---|---|---|---|---|
| 26940 | TGAATAAGCCATTGTGGG | 151 | 0049–0066 | AUG |
| 26941 | CTTTATGCTCTTCTGAAT | 152 | 0062–0079 | coding |
| 26942 | GGATGAAACCACAGGGCA | 153 | 0083–0100 | coding |
| 26943 | TCAAAGTCCAAGGAAATG | 154 | 0120–0137 | coding |
| 26944 | TGAAGCACCGAGTGGCAG | 155 | 0195–0212 | coding |
| 26945 | GGGCAGATTGGCACTGTG | 156 | 0282–0299 | coding |

TABLE 9-continued

Nucleotide Sequences of Human TRAF-5 Phosphorothioate Oligonucleotides

| ISIS NO. | NUCLEOTIDE SEQUENCE[1] (5' -> 3') | SEQ ID NO: | TARGET GENE NUCLEOTIDE COORDINATES[2] | GENE TARGET REGION |
|---|---|---|---|---|
| 26946 | CTCCTGAGATTTGATGAC | 157 | 0313–0330 | coding |
| 26947 | CTTTCCGTAGGACTGGCT | 158 | 0491–0508 | coding |
| 26948 | GATTCTGTAGATTGATGA | 159 | 0584–0601 | coding |
| 26949 | TTCATCTACCTCAGTTTT | 160 | 0667–0684 | coding |
| 26950 | TCCGTTACAGCACAGCCA | 161 | 0735–0752 | coding |
| 26951 | GCATGTGCTCCCGTAAGG | 162 | 0788–0805 | coding |
| 26952 | CTTTTCAAGTTTCTTTAT | 163 | 0907–0924 | coding |
| 26953 | CTTCCATCAAAGGTCTCA | 164 | 1079–1096 | coding |
| 26954 | TCTAAAACGGCTAATCTT | 165 | 1146–1163 | coding |
| 26955 | TCATCTTGTAATCTGTCA | 166 | 1283–1300 | coding |
| 26956 | GGACTGGCTGAAGATGGA | 167 | 1333–1350 | coding |
| 26957 | CCCTCCCTGACCCATCCC | 168 | 1403–1420 | coding |
| 26958 | GAATGAGCCACAAAGCGG | 169 | 1620–1637 | coding |
| 26959 | CAAGAACAGAGTGTCATC | 170 | 1672–1689 | coding |
| 26960 | GTCTAAATCCAGGTCAAT | 171 | 1799–1816 | 3'-UTR |
| 26961 | AAACTTACCATCTTTCAA | 172 | 1964–1981 | 3'-UTR |
| 26962 | CTCTGTGTCCTCCATAAC | 173 | 2053–2070 | 3'-UTR |
| 26963 | CTTAACTGGAACAGCCTA | 174 | 2167–2184 | 3'-UTR |
| 26964 | GCAGGAAGAATGAAAATG | 175 | 2352–2369 | 3'-UTR |
| 26965 | TATTTGGTTGAATCTTAT | 176 | 2501–2518 | 3'-UTR |
| 26966 | AAATTCTATCCATCCTCA | 177 | 2611–2628 | 3'-UTR |
| 26967 | AAATTGTAAAGGTTTTCT | 178 | 2683–2700 | 3'-UTR |
| 26968 | ACAATGAAACTCTGTCTC | 179 | 2779–2796 | 3'-UTR |
| 26969 | GCAAAACTCCGTCTCTAC | 180 | 2940–2957 | 3'-UTR |
| 26970 | CAATAGTTGTCAGAGGCT | 181 | 3055–3072 | 3'-UTR |
| 26971 | AAGGACTCATCTCAGTTT | 182 | 3209–3226 | 3'-UTR |
| 26972 | TAACAACGCAGAAGGGCT | 183 | 3280–3297 | 3'-UTR |
| 26973 | AGTAGGGAAGTGGCATAA | 184 | 3295–3312 | 3'-UTR |
| 26974 | CATCACCAGGTAAGCAGC | 185 | 3377–3394 | 3'-UTR |
| 26975 | TCCTGTTGTGAACCTATT | 186 | 3553–3570 | 3'-UTR |
| 26976 | GGACTTGTGGGCTAAAGA | 187 | 3656–3673 | 3'-UTR |
| 26977 | GCTCAGGAAGACAGAGTG | 188 | 3724–3741 | 3'-UTR |
| 26978 | TGAACTCCTAAGCAAACC | 189 | 3873–3890 | 3'-UTR |
| 26979 | GATGATGAAGGAACTCTG | 190 | 3889–3906 | 3'-UTR |

[1]All cytidines are 5-methyl-cytidines; all linkages are phosphorothioate linkages.
[2]Coordinates from GenBank Accession No. AB000509, locus name "AB000509" SEQ ID NO. 5.

Example 22

Antisense Inhibition of TRAF-5 Expression-Phosphorothioate 2'-MOE Gapmer Oligonucleotides In accordance with the present invention, a second series of oligonucleotides targeted to human TRAF-5 were synthesized. The oligonucleotide sequences are shown in Table 10. Target sites are indicated by nucleotide numbers, as given in the sequence source reference (GenBank accession no. AB000509), to which the oligonucleotide binds.

All compounds in Table 10 are chimeric oligonucleotides ("gapmers") 18 nucleotides in length, composed of a central "gap" region consisting of ten 2'-deoxynucleotides, which is flanked on both sides (5' and 3' directions) by four-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

TABLE 10

Nucleotide Sequences of Human TRAF-5 Gapmer Oligonucleotides

| ISIS NO. | NUCLEOTIDE SEQUENCE[1] (5' -> 3') | SEQ ID NO: | TARGET GENE NUCLEOTIDE COORDINATES[2] | GENE TARGET REGION |
|---|---|---|---|---|
| 26980 | TGAATAAGCCATTGTGGG | 151 | 0049–0066 | AUG |
| 26981 | CTTTATGCTCTTCTGAAT | 152 | 0062–0079 | coding |
| 26982 | GGATGAAACCACAGGGCA | 153 | 0083–0100 | coding |
| 26983 | TCAAAGTCCAAGGAAATG | 154 | 0120–0137 | coding |
| 26984 | TGAAGCACCGAGTGGCAG | 155 | 0195–0212 | coding |
| 26985 | GGGCAGATTGGCACTGTG | 156 | 0282–0299 | coding |
| 26986 | CTCCTGAGATTTGATGAC | 157 | 0313–0330 | coding |
| 26987 | CTTTCCGTAGGACTGGCT | 158 | 0491–0508 | coding |
| 26988 | GATTCTGTAGATTGATGA | 159 | 0584–0601 | coding |
| 26989 | TTCATCTACCTCAGTTTT | 160 | 0667–0684 | coding |

TABLE 10-continued

Nucleotide Sequences of Human TRAF-5 Gapmer Oligonucleotides

| ISIS NO. | NUCLEOTIDE SEQUENCE[1] (5' -> 3') | SEQ ID NO: | TARGET GENE NUCLEOTIDE COORDINATES[2] | GENE TARGET REGION |
|---|---|---|---|---|
| 26990 | TCCGTTACAGCACAGCCA | 161 | 0735–0752 | coding |
| 26991 | GCATGTGCTCCCGTAAGG | 162 | 0788–0805 | coding |
| 26992 | CTTTTCAAGTTTCTTTAT | 163 | 0907–0924 | coding |
| 26993 | CTTCCATCAAAGGTCTCA | 164 | 1079–1096 | coding |
| 26994 | TCTAAAACGGCTAATCTT | 165 | 1146–1163 | coding |
| 26995 | TCATCTTGTAATCTGTCA | 166 | 1283–1300 | coding |
| 26996 | GGACTGGCTGAAGATGGA | 167 | 1333–1350 | coding |
| 26997 | CCCTCCCTGACCCATCCC | 168 | 1403–1420 | coding |
| 26998 | GAATGAGCCACAAAGCGG | 169 | 1620–1637 | coding |
| 26999 | CAAGAACAGAGTGTCATC | 170 | 1672–1689 | coding |
| 27000 | GTCTAAATCCAGGTCAAT | 171 | 1799–1816 | 3'-UTR |
| 27001 | AAACTTACCATCTTTCAA | 172 | 1964–1981 | 3'-UTR |
| 27002 | CTCTGTGTCCTCCATAAC | 173 | 2053–2070 | 3'-UTR |
| 27003 | CTTAACTGGAACAGCCTA | 174 | 2167–2184 | 3'-UTR |
| 27004 | GCAGGAAGAATGAAAATG | 175 | 2352–2369 | 3'-UTR |
| 27005 | TATTTGGTTGAATCTTAT | 176 | 2501–2518 | 3'-UTR |
| 27006 | AAATTCTATCCATCCTCA | 177 | 2611–2628 | 3'-UTR |
| 27007 | AAATTGTAAAGGTTTTCT | 178 | 2683–2700 | 3'-UTR |
| 27008 | ACAATGAAACTCTGTCTC | 179 | 2779–2796 | 3'-UTR |
| 27009 | GCAAAACTCCGTCTCTAC | 180 | 2940–2957 | 3'-UTR |
| 27010 | CAATAGTTGTCAGAGGCT | 181 | 3055–3072 | 3'-UTR |
| 27011 | AAGGACTCATCTCAGTTT | 182 | 3209–3226 | 3'-UTR |
| 27012 | TAACAACGCAGAAGGGCT | 183 | 3280–3297 | 3'-UTR |
| 27013 | AGTAGGGAAGTGGCATAA | 184 | 3295–3312 | 3'-UTR |
| 27014 | CATCACCAGGTAAGCAGC | 185 | 3377–3394 | 3'-UTR |
| 27015 | TCCTGTTGTGAACCTATT | 186 | 3553–3570 | 3'-UTR |
| 27016 | GGACTTGTGGGCTAAAGA | 187 | 3656–3673 | 3'-UTR |
| 27017 | GCTCAGGAAGACAGAGTG | 188 | 3724–3741 | 3'-UTR |
| 27018 | TGAACTCCTAAGCAAACC | 189 | 3873–3890 | 3'-UTR |
| 27019 | GATGATGAAGGAACTCTG | 190 | 3889–3906 | 3'-UTR |

[1]Emboldened residues are 2'-methoxyethoxy residues (others are 2'-deoxy-). All 2'-methoxyethoxy cytidines and 2'-deoxycytidines are 5-methyl-cytidines; all linkages are phosphorothioate linkages.
[2]Coordinates from GenBank Accession No. AB000509, locus name "AB000509" SEQ ID NO. 5.

Example 23

Antisense Inhibition of TRAF-6 Expression-Phosphorothioate 2'-MOE Gapmer Oligonucleotides In accordance with the present invention, a series of oligonucleotides targeted to human TRAF-6 were synthesized. The oligonucleotide sequences are shown in Table 11. Target sites are indicated by nucleotide numbers, as given in the sequence source reference (GenBank accession no. U78798), to which the oligonucleotide binds.

All compounds in Table 11 are chimeric oligonucleotides ("gapmers") 20 nucleotides in length, composed of a central "gap" region consisting of eight 2'-deoxynucleotides, which is flanked on both sides (5' and 3' directions) by six-nucleotide "wings". The wings are composed of 2'-methoxyethyl (2'-MOE) nucleotides. The internucleoside (backbone) linkages are phosphorothioate (P=S) in the "deoxy gap" and phosphodiester (P=O) in the wings. Cytidine residues in the 2'-MOE wings are 5-methylcytidines.

TABLE 11

Nucleotide Sequences of TRAF-6 Gapmer Oligonucleotides

| ISIS NO. | NUCLEOTIDE SEQUENCE[1] (5' -> 3') | SEQ ID NO: | TARGET GENE NUCLEOTIDE COORDINATES[2] | GENE TARGET REGION |
|---|---|---|---|---|
| 15779 | AoGoGoCoCoAsAsGsCsCsCsAsGsCoToGoCoGoG | 191 | 0001–0020 | 5'-UTR |
| 15880 | CoGoCoCoAoCsCsTsTsCsGsCsTsGsGoCoCoGoCoC | 192 | 0024–0043 | 5'-UTR |
| 15881 | GoAoGoAoCoGsAsGsGsCsTsGsCsTsToGoGoAoCoG | 193 | 0071–0090 | 5'-UTR |
| 15882 | GoGoAoCoAoCsAsGsAsCsAsCsTsGsCoGoCoGoCoC | 194 | 0091–0110 | 5'-UTR |
| 15883 | CoCoAoAoGoGsCsGsCsTsGsGsTsAsGoAoGoGoAoC | 195 | 0111–0130 | 5'-UTR |
| 15884 | ToToGoCoToCsGsTsTsCsTsAsGsTsGoCoGoCoGoG | 196 | 0185–0204 | 5'-UTR |
| 15885 | CoAoToAoGoTsAsAsCsTsTsGsAsTsToAoToCoAoC | 197 | 0205–0224 | AUG |
| 15886 | AoGoCoAoGoAsCsTsCsAsTsAsGsTsAoAoCoToToG | 198 | 0213–0232 | AUG |
| 15887 | AoCoAoGoToTsTsAsGsCsAsGsAsCsToCoAoToAoG | 199 | 0220–0239 | AUG |
| 15888 | AoCoAoGoCoGsCsTsAsCsAsGsGsAsGoCoToGoGoC | 200 | 0291–0310 | coding |
| 15889 | AoToToGoAoTsTsTsTsAsTsGsAsTsGoCoAoGoGoC | 201 | 0495–0514 | coding |
| 15890 | GoToGoAoCoCsTsGsCsAsTsCsCsCsToToAoToToG | 202 | 0511–0530 | coding |
| 15891 | GoToCoToCoAsGsTsTsCsCsAsTsCsToToGoToGoC | 203 | 0641–0660 | coding |
| 15892 | AoGoAoGoCoAsAsAsCsTsCsAsCsAsAoToGoToGoC | 204 | 0678–0697 | coding |

TABLE 11-continued

Nucleotide Sequences of TRAF-6 Gapmer Oligonucleotides

| ISIS NO. | NUCLEOTIDE SEQUENCE[1] (5' -> 3') | SEQ ID NO: | TARGET GENE NUCLEOTIDE COORDINATES[2] | GENE TARGET REGION |
|---|---|---|---|---|
| 15893 | ToToToToGoGsAsAsGsGsGsAsCsGsCoToGoGoCoA | 205 | 0714–0733 | coding |
| 15894 | AoAoAoToGoCsCsAsTsTsGsAsTsGsCoAoGoCoAoC | 206 | 0796–0815 | coding |
| 15895 | AoToToCoAoCsAsGsAsTsGsAsCsAsToToToGoCoC | 207 | 0851–0870 | coding |
| 15896 | CoGoToGoCoCsAsAsGsTsGsAsTsTsCoCoToCoToG | 208 | 0981–1000 | coding |
| 15897 | GoGoToGoToTsCsTsCsTsTsGsTsAsGoGoToGoGoC | 209 | 1000–1019 | coding |
| 15898 | GoGoCoCoAoAsCsAsTsTsCsTsCsAsToGoToGoToG | 210 | 1024–1043 | coding |
| 15899 | CoGoCoToCoAsAsAsCsTsAsTsGsAsAoCoAoGoCoC | 211 | 1046–1065 | coding |
| 15900 | AoGoGoCoGoAsCsCsCsTsCsTsAsAsCoToGoGoToG | 212 | 1119–1138 | coding |
| 15901 | CoCoAoToToTsTsAsGsCsAsGsTsCsAoGoCoToCoC | 213 | 1163–1182 | coding |
| 15902 | CoGoAoAoToGsGsTsTsCsGsTsTsTsGoAoGoCoToC | 214 | 1206–1225 | coding |
| 15903 | CoCoAoToToGsCsAsCsTsGsCsTsGsToGoCoToToC | 215 | 1254–1273 | coding |
| 15904 | GoCoAoGoToCsGsGsTsAsAsCsTsGsAoAoGoGoToG | 216 | 1401–1420 | coding |
| 15905 | GoCoCoToToAsCsAsGsGsTsGsCsTsToCoAoGoAoC | 217 | 1532–1551 | coding |
| 15906 | AoGoCoAoAoGsCsAsGsCsTsCsTsGsGoToToToGoG | 218 | 1576–1595 | coding |
| 15907 | GoGoCoToAoCsCsCsAsTsGsTsCsAsAoAoGoCoGoG | 219 | 1724–1743 | coding |
| 15908 | ToToGoToToTsTsTsGsAsGsCsAsAsGoToGoAoGoG | 220 | 1796–1815 | 3'-UTR |
| 15909 | GoGoCoAoCoTsGsTsTsTsTsCsTsCsCoAoGoGoToA | 221 | 1817–1836 | 3'-UTR |
| 15910 | AoCoAoToAoTsTsTsCsCsCsGsTsGsGoCoToToGoT | 222 | 1871–1890 | 3'-UTR |
| 15911 | GoGoAoAoCoGsTsGsTsGsGsAsTsTsCoCoCoAoGoG | 223 | 1967–1986 | 3'-UTR |
| 15912 | ToGoCoToGoCsAsAsCsAsTsGsCsCsAoCoAoGoGoC | 224 | 2017–2036 | 3'-UTR |
| 15913 | AoToAoCoAoCsCsAsGsAsGsCsAsAsAoAoGoCoCoC | 225 | 2078–2097 | 3'-UTR |
| 15914 | AoAoAoGoAsCsTsGsAsAsCsTsTsToToAoAoGoG | 226 | scrambled control | |
| 23247 | AoCoToToAoAsTsTsAsCsCsAsTsGsAoCoToAoGoT | 227 | 15910 mismatch | |
| 23248 | CoCoAoCoGoAsGsGsAsGsCsAsCsCsAoToCoAoAoG | 228 | 16834 mismatch | |
| 27691 | AsCsAsTsAsTsTsTsCsCsCsGsTsGsGsCsTsTsGsT | 222 | 1871–1890 | 3'-UTR |
| 27692 | AoCoAoToAsTsTsTsCsCsCsGsTsGsGsGsCoToToGoT | 222 | 1871–1890 | 3'-UTR |

[1]Emboldened residues are 2'-methoxyethoxy residues (others are 2'-deoxy). All 2'-methoxyethoxy cytidines are 5-methyl-cytidines; underlined "C" are 5-methyl-cytidine; "s" linkages are phosphorothioate linkages, "o" linkages are phosphodiester linkages.
[2]Coordinates from GenBank Accession No. U78798, locus name "HSU78798" SEQ ID NO. 6.

HMVEC cells were grown in 100 mm petri dishes until 70–80% confluent and then treated with oligonucleotide in the presence of cationic lipid. Briefly, cells were washed with PBS and OPTI-MEM®. OPTI-MEM® containing 10 μg/mL LIPOFECTIN® (Life Technologies, Rockville Md.) was added to the cells, followed by addition of oligonucleotide. The cells were incubated for 3–4 hours at 37° C., washed once with EBM/1% FBS, and allowed to recover. For determination of mRNA levels by Northern blot, total RNA was prepared from cells by the guanidinium isothiocyanate procedure or by the Qiagen RNEASY™ method (Qiagen, Valencia, Calif.). Northern blot analysis was performed by standard methods (for example, Ausubel, et al. *Current Protocols in Molecular Biology*, Vol. 1, John Wiley and Sons, Inc., 1996, pp.4.2.1–4.2.9). The probe was a PCR-labeled 1-kb fragment of TRAF-6 amplified by RT-PCR according to the method of Bednarczuk et al., 1991, Biotechniques 10,478. RNA was quantified and normalized to G3 PDH mRNA levels using a Molecular Dynamics (Sunnyvale, Calif.) PhosphorImager in accordance with manufacturer's instructions.

Results are shown in Table 12. Reduction of TRAF-6 mRNA levels with oligonucleotide 15910 (SEQ ID NO. 224) was determined to be dose-dependent in the range of 1 to 100 nM. The $IC_{50}$ was approximately 2.5 nM. A TRAF-2 antisense oligonucleotide did not affect TRAF-6 mRNA expression.

TABLE 12

Activities of TRAF-6 Gapmer Oligonucleotides

| ISIS No: | SEQ ID NO: | GENE TARGET REGION | % mRNA EXPRESSION | % mRNA INHIBITION |
|---|---|---|---|---|
| LIPOFECTIN ® only | — | — | 100% | 0% |
| 15779 | 191 | 5'-UTR | 62% | 38% |
| 15880 | 192 | 5'-UTR | 73% | 27% |
| 15881 | 193 | 5'-UTR | 28% | 72% |
| 15882 | 194 | 5'-UTR | 96% | 4% |
| 15883 | 195 | 5'-UTR | 57% | 43% |
| 15884 | 196 | 5'-UTR | 73% | 27% |
| 15885 | 197 | AUG | 61% | 39% |
| 15886 | 198 | AUG | 37% | 63% |
| 15887 | 199 | AUG | 23% | 77% |
| 15888 | 200 | coding | 31% | 69% |
| 15889 | 201 | coding | 42% | 58% |
| 15890 | 202 | coding | 49% | 51% |
| 15891 | 203 | coding | 50% | 50% |
| 15892 | 204 | coding | 32% | 68% |
| 15893 | 205 | coding | 18% | 82% |
| 15894 | 206 | coding | 43% | 57% |
| 15895 | 207 | coding | 41% | 59% |
| 15896 | 208 | coding | 20% | 80% |
| 15897 | 209 | coding | 60% | 40% |
| 15898 | 210 | coding | 23% | 77% |
| 15899 | 211 | coding | 66% | 34% |
| 15900 | 212 | coding | 54% | 46% |
| 15901 | 213 | coding | 60% | 40% |
| 15902 | 214 | coding | 76% | 24% |
| 15903 | 215 | coding | 58% | 42% |
| 15904 | 216 | coding | 77% | 23% |
| 15905 | 217 | coding | 108% | — |
| 15906 | 218 | coding | 90% | 10% |

TABLE 12-continued

Activities of TRAF-6 Gapmer Oligonucleotides

| ISIS No: | SEQ ID NO: | GENE TARGET REGION | % mRNA EXPRESSION | % mRNA INHIBITION |
|---|---|---|---|---|
| 15907 | 219 | coding | 62% | 38% |
| 15908 | 220 | 3'-UTR | 82% | 18% |
| 15909 | 221 | 3'-UTR | 28% | 72% |
| 15910 | 222 | 3'-UTR | 13% | 87% |
| 15911 | 223 | 3'-UTR | 103% | — |
| 15912 | 224 | 3'-UTR | 20% | 80% |
| 15913 | 225 | 3'-UTR | 97% | 3% |
| 15914 | 226 | scrambled control | 70% | 30% |

Example 24

Effect of Inhibiting TRAF Gene Expression on the Induction of E-selectin

The effect of TRAF antisense oligonucleotides on the induction of E-selectin by TNFα or IL-1β was examined. HMVEC cells were treated with either ISIS 16834 or ISIS 15910 under dose-response conditions followed by stimulation of E-selectin expression by TNFα or IL-1β for 5 hours. The cell surface expression of E-selectin was determined by flow cytometry analysis. Dose-dependent inhibition of E-selectin cell surface induction by TNFα was observed in cells treated with the TRAF-2 antisense oligonucleotide ISIS 16834, as expected. Surprisingly, the TRAF-6 antisense compound, ISIS 15910, was able to inhibit TNFα mediated E-selectin surface expression as well, especially at higher dose. At low doses (20–50 nM), ISIS 16834 was a more effective inhibitor of TNFα-mediated E-selectin induction than ISIS 15910. Maximal inhibition of E-selectin induction for both antisense compounds was approximately 70% at 100 nM. Control oligonucleotides exhibited little to no effect on E-selectin induction. When IL-1β was used as the stimulator, however, ISIS 15910 appeared to be a more specific and potent inhibitor of E-selectin induction than ISIS 16834, especially at relatively low doses.

Example 25

Effect of TRAF Antisense Oligonucleotide on IκBα Phosphorylation and Degradation Multiple transcription factors are activated by cytokines to facilitate the induction of E-selectin. The most important and best studied transcription factors involved in the regulation of E-selectin activation include NF-κB, c-Jun and ATF-2. To clarify the roles of TRAF proteins in the activation of NF-κB by cytokines, IκBα phosphorylation and degradation assays were performed with antisense oligonucleotide treated cells. Cells were treated with either ISIS 16834 or ISIS 15910 and allowed to recover for 48–72 hours. Tumor necrosis factor-α (TNF-α) or interleukin-1-β (IL-1β) was added for 5 to 30 minutes before cells were harvested. Western blot analysis with antibody specific for phospho-IκBα was performed to study the phosphorylation of IκBα. The blots were then stripped and reblotted with antibody against IκBα to study the degradation of IκBα. IκBα was heavily phosphorylated 5 minutes after addition of either cytokine. By 30 minutes, IκBα was reduced, probably as a result of IκBα degradation. In TNFα-stimulated cells, the majority of the IκBα had been degraded after 5 minutes of stimulation. By 30 minutes, IκBα was almost completely gone. In contrast, the degradation of IκBα in IL-1β stimulated cells was slower with the majority of IκBα degraded by 30 minutes. Neither ISIS 16834 nor ISIS 15910 affected IκBα phosphorylation and degradation induced by TNFα. ISIS 15910 has little effect on IL-1β mediated IκBα phosphorylation and degradation either. Hyperphosphorylation of IκBα was observed in ISIS 16834 treated, IL-1β induced cells. In summary, the antisense oligonucleotides do not inhibit the phosphorylation and degradation of IκBα.

Example 26

Effect of TRAF Antisense Oligonucleotides on JNK Activities

MAP kinases play central roles in the activation of specific transcription factors crucial to the induction of cell adhesion molecules. To examine the effect of TRAF antisense oligonucleotides on JNK activities, in vitro kinase assays were performed on extracts derived from cells treated with TRAF antisense oligonucleotides. Cells were treated with TRAF-2 or TRAF-6 antisense compounds, (ISIS 16834 or ISIS 15910, respectively) allowed to recover for 48–72 hours, at which time TNF was added for 15 minutes prior to the cell lysis and the initiation of the kinase assays. Specific c-Jun conjugated agarose beads were used to precipitate JNK. ATP was added to the immunoprecipitated kinase complexes and the reaction mixes were analyzed on SDS-PAGE. Western blotting with antibodies specific for phosphorylated c-Jun was carried out to determine relative kinase activity. JNK was activated by TNFα after a 15 minute incubation, as indicated by the heavy phosphorylation of c-Jun. ISIS 16834 reduced JNK activity in TNFα-treated cells but not in IL-1β treated cells. Some hyperphosphorylation of c-Jun induced by IL-1β in ISIS 16834 treated cells was observed. ISIS 15910 reduced the c-Jun phosphorylation mediated by both IL-1β and TNFα. Some inhibitory effect of ISIS 15910 on JNK activity was also observed in TNFα-induced cells. This result is consistent with the inhibitory effects of TRAF antisense oligonucleotides on the surface expression of E-selectin.

What is claimed is:

1. An antisense compound 8 to 30 nucleotides in length comprising at least an 8 nucleobase portion of SEQ ID NO: 151, 152, 153, 154, 155, 156, 157, 158, 159, 160, 161, 162, 163, 164, 165, 166, 167, 168, 169, 170, 171, 172, 173, 174, 175, 276, 177, 178, 179, 180, 181, 182, 183, 184, 185, 186, 187, 188, 189 or 190.

2. The antisense compound of claim 1 which is an antisense oligonucleotide.

3. The antisense oligonucleotide of claim 2 which comprises at least one modified internucleoside linkage.

4. The antisense oligonucleotide of claim 3 wherein the modified internucleoside linkage is a phosphorothioate linkage.

5. The antisense oligonucleotide of claim 2 which comprises at least one modified sugar moiety.

6. The antisense oligonucleotide of claim 5 wherein the modified sugar moiety is a 2'-o-methoxyethyl sugar.

7. The antisense oligonucleotide of claim 2 which comprises at least one modified nucleobase.

8. The antisense oligonucleotide of claim 7 wherein the modified nucleobase is a 5-methylcytosine.

9. The antisense compound of claim 1 which is a chimeric oligonucleotide.

10. A composition comprising the antisense compound of claim 1 and a pharmaceutically acceptable carrier or diluent.

11. The composition of claim 10 comprising a colloidal dispersion system.

12. The composition of claim 10 wherein the antisense compound is an antisense oligonucleotide.

13. A method for inhibiting the expression of tumor necrosis factor receptor-associated factor 5 in human cell or tissues comprising contacting said cells or tissues in vitro with the antisense compound of claim 1 so that expression of tumor necrosis factor receptor-associated factor 5 is inhibited.

* * * * *

SEQUENCE LISTING

<160> NUMBER OF SEQ ID NOS: 228

<210> SEQ ID NO 1
<211> LENGTH: 2380
<212> TYPE: DNA

-continued

```
<213> ORGANISM: Homo sapiens
<220> FEATURE:
<221> NAME/KEY: CDS
<222> LOCATION: (76)..(1326)
<300> PUBLICATION INFORMATION:
<308> DATABASE ACCESSION NUMBER: U19261 Genbank
<309> DATABASE ENTRY DATE: 1995-02-21

<400> SEQUENCE: 1
```

| | |
|---|---:|
| gccaggactc cacaaggctg gtccctgcc ctggagcaac ttaaacaggc c ctctggcca | 60 |

| gcctggaacc ctgag atg gcc tcc agc tca ggc agc agt cct cgc ccg gcc | 111 |
|---|---:|
|                     Met  Ala Ser Ser Ser Gly Ser Ser Pro Arg Pro Ala<br>                      1              5                  10 | |

| cct gat gag aat gag ttt ccc ttt ggg tgc c ct ccc acc gtc tgc cag | 159 |
|---|---:|
| Pro Asp Glu Asn Glu Phe Pro Phe Gly Cys P ro Pro Thr Val Cys Gln<br>         15                  20               25 | |

| gac cca aag gag ccc agg gct ctc tgc tgt g ca ggc tgt ctc tct gag | 207 |
|---|---:|
| Asp Pro Lys Glu Pro Arg Ala Leu Cys Cys A la Gly Cys Leu Ser Glu<br>    30                      35               40 | |

| aac ccg agg aat ggc gag gat cag atc tgc c cc aaa tgc aga ggg gaa | 255 |
|---|---:|
| Asn Pro Arg Asn Gly Glu Asp Gln Ile Cys P ro Lys Cys Arg Gly Glu<br>45                 50               55               60 | |

| gac ctc cag tct ata agc cca gga agc cgt c tt cga act cag gag aag | 303 |
|---|---:|
| Asp Leu Gln Ser Ile Ser Pro Gly Ser Arg L eu Arg Thr Gln Glu Lys<br>             65                   70              75 | |

| gct cac ccc gag gtg gct gag gct gga att g gg tgc ccc ttt gca ggt | 351 |
|---|---:|
| Ala His Pro Glu Val Ala Glu Ala Gly Ile G ly Cys Pro Phe Ala Gly<br>         80                      85               90 | |

| gtc ggc tgc tcc ttc aag gga agc cca cag t ct gtg caa gag cat gag | 399 |
|---|---:|
| Val Gly Cys Ser Phe Lys Gly Ser Pro Gln S er Val Gln Glu His Glu<br>             95                   100             105 | |

| gtc acc tcc cag acc tcc cac cta aac ctg c tg ttg ggg ttc atg aaa | 447 |
|---|---:|
| Val Thr Ser Gln Thr Ser His Leu Asn Leu L eu Leu Gly Phe Met Lys<br>    110                   115             120 | |

| cag tgg aag gcc cgg ctg ggc tgt ggc ctg g ag tct ggg ccc atg gcc | 495 |
|---|---:|
| Gln Trp Lys Ala Arg Leu Gly Cys Gly Leu G lu Ser Gly Pro Met Ala<br>125                 130               135              140 | |

| ctg gag cag aac ctg tca gac ctg cag ctg c ag gca gcc gtg gaa gtg | 543 |
|---|---:|
| Leu Glu Gln Asn Leu Ser Asp Leu Gln Leu G ln Ala Ala Val Glu Val<br>                  145               150              155 | |

| gcg ggg gac ctg gag gtc gat tgc tac cgg g ca ccc tgc tcc gag agc | 591 |
|---|---:|
| Ala Gly Asp Leu Glu Val Asp Cys Tyr Arg A la Pro Cys Ser Glu Ser<br>             160                  165             170 | |

| cag gag gag ctg gcc ctg cag cac ttc atg a ag gag aag ctt ctg gct | 639 |
|---|---:|
| Gln Glu Glu Leu Ala Leu Gln His Phe Met L ys Glu Lys Leu Leu Ala<br>           175                  180             185 | |

| gag ctg gag ggg aag ctg cgt gtg ttt gag a ac att gtt gct gtc ctc | 687 |
|---|---:|
| Glu Leu Glu Gly Lys Leu Arg Val Phe Glu A sn Ile Val Ala Val Leu<br>    190                   195              200 | |

| aac aag gag gtg gag gcc tcc cac ctg gcc c tg gcc acc tct atc cac | 735 |
|---|---:|
| Asn Lys Glu Val Glu Ala Ser His Leu Ala L eu Ala Thr Ser Ile His<br>205                 210               215              220 | |

| cag agc cag ctg gac cgt gag cgc atc ctg a gc ttg gag cag agg gtg | 783 |
|---|---:|
| Gln Ser Gln Leu Asp Arg Glu Arg Ile Leu S er Leu Glu Gln Arg Val<br>                  225               230              235 | |

| gtg gag ctt cag cag acc ctg gcc cag aaa g ac cag gcc ctg ggc aag | 831 |
|---|---:|
| Val Glu Leu Gln Gln Thr Leu Ala Gln Lys A sp Gln Ala Leu Gly Lys<br>             240                  245             250 | |

| ctg gag cag agc ttg cgc ctc atg gag gag g cc tcc ttc gat ggc act | 879 |
|---|---:|
| Leu Glu Gln Ser Leu Arg Leu Met Glu Glu A la Ser Phe Asp Gly Thr<br>           255                  260             265 | |

-continued

```
ttc ctg tgg aag atc acc aat gtc acc agg c gg tgc cat gag tcg gcc      927
Phe Leu Trp Lys Ile Thr Asn Val Thr Arg A rg Cys His Glu Ser Ala
        270                 275                 280 tgt ggc agg acc gtc agc ctc ttc tcc cca g cc ttc tac act gcc aag      975
Cys Gly Arg Thr Val Ser Leu Phe Ser Pro A la Phe Tyr Thr Ala Lys
285                 290                 295                 300 tat ggc tac aag ttg tgc ctg cgg ctg tac c tg aat gga gat ggc act     1023
Tyr Gly Tyr Lys Leu Cys Leu Arg Leu Tyr L eu Asn Gly Asp Gly Thr
                305                 310                 315 gga aag aga acc cat ctg tcg ctc ttc atc g tg atc atg aga ggg gag     1071
Gly Lys Arg Thr His Leu Ser Leu Phe Ile V al Ile Met Arg Gly Glu
            320                 325                 330 tat gat gcg ctg ctg ccg tgg ccc ttc cgg a ac aag gtc acc ttc atg     1119
Tyr Asp Ala Leu Leu Pro Trp Pro Phe Arg A sn Lys Val Thr Phe Met
        335                 340                 345 ctg ctg gac cag aac aac cgt gag cac gcc a tt gac gcc ttc cgg cct     1167
Leu Leu Asp Gln Asn Asn Arg Glu His Ala I le Asp Ala Phe Arg Pro
    350                 355                 360 gac cta agc tca gcg tcc ttc cag agg ccc c ag agt gaa acc aac gtg     1215
Asp Leu Ser Ser Ala Ser Phe Gln Arg Pro G ln Ser Glu Thr Asn Val
365                 370                 375                 380 gcc agt gga tgc cca ctc ttc ttc ccc ctc a gc aaa ctg cag tca ccc     1263
Ala Ser Gly Cys Pro Leu Phe Phe Pro Leu S er Lys Leu Gln Ser Pro
                385                 390                 395 aag cac gcc tac gtg aag gac gac aca atg t tc ctc aag tgc att gtg     1311
Lys His Ala Tyr Val Lys Asp Asp Thr Met P he Leu Lys Cys Ile Val
            400                 405                 410 gag acc agc act tag ggtgggcggg gctcctgagg gagctcca ac tcagaaggga     1366
Glu Thr Ser Thr
            415 gctagccaga ggactgtgat gccctgccct tggcacccaa gacctcaggg c acaaagatg   1426 ggtgaaggct ggcatgatcc aagcaagact gagggtcga cttcgggctg g ccatctggt    1486 taggatggca ggacgtgggc tgggcccaca aaggcaaagg gtccagaagg a gacaggcag  1546 agctgctccc ctctgcacgg accatgcgac actgggaggc cagtgagcca c tccggcccc  1606 gaatgttgag gtggactctc accaaatgag aagaaaatgg aaccaggctt g gaaccgtag  1666 gacccaagca gagaagctct cgggctagga agatctctgc agggccgcca g ggagacctg  1726 gacacaggcc tgctctcttt ttctccaggg tcagaaacag gaccgggtgg a agggatggg  1786 gtgccagttt gaatgcagtc tgtccaggct cgtcattgga ggtgaacaag c aaacccaga  1846 cggctccact aggacttcaa attgggggtt ggatttgaag acttttaagt t tccttccag  1906 cccagaaagt ctctcattct agcctcctgg cccaggtgag tcctagagct a cagggttc   1966 tggaaacatt caggagcttc ctgtcctccc agctcctcac tcaccttcag t aaccccac   2026 tggactgacc tggtccacag ggcacctgcc acctgggcc tggcagctca g cttcccaac   2086 acgcaggagc acacccagcc cccacatcct gtgcctccat cagctaaaca c cacgtcact  2146 tcatgcaggt gaaacccagt cactgtgagc tcccaggtgc agccagaggc a cctcaagaa  2206 gaagagggc ataaactttc ctcttcctgc ctagaggccc caccctttggt g ctttccaga  2266 atcccgtaac acctgattaa ctgaggcatc cacttctttc agcagactga t caggacctc  2326 caagccactg agcaatgtat aaccccaaag ggaattcaaa aaaaaaaaaa a aaa        2380
```

<210> SEQ ID NO 2
<211> LENGTH: 2262

-continued

```
<212> TYPE: DNA
<213> ORGANISM: Homo sapiens
<220> FEATURE:
<221> NAME/KEY: CDS
<222> LOCATION: (55)..(1560)
<300> PUBLICATION INFORMATION:
<308> DATABASE ACCESSION NUMBER: U12597 Genbank
<309> DATABASE ENTRY DATE: 1996-02-16

<400> SEQUENCE: 2
```

| | | |
|---|---|---|
| gaattccggc gcgctgcgac cgttgggct ttgttcgcgg gggtcacagc t ctc atg<br>                                                                                                      Met<br>                                                                                                      1 | 57 |

```
gct gca gct agc gtg acc ccc cct ggc tcc c tg gag ttg cta cag ccc       105
Ala Ala Ala Ser Val Thr Pro Pro Gly Ser L eu Glu Leu Leu Gln Pro
            5                  10                  15 ggc ttc tcc aag acc ctc ctg ggg acc aag c tg gaa gcc aag tac ctg       153
Gly Phe Ser Lys Thr Leu Leu Gly Thr Lys L eu Glu Ala Lys Tyr Leu
 20                  25                  30 tgc tcc gcc tgc aga aac gtc ctc cgc agg c cc ttc cag gcg cag tgt       201
Cys Ser Ala Cys Arg Asn Val Leu Arg Arg P ro Phe Gln Ala Gln Cys
 35                  40                  45 ggc cac cgg tac tgc tcc ttc tgc ctg gcc a gc atc ctc agc tct ggg       249
Gly His Arg Tyr Cys Ser Phe Cys Leu Ala S er Ile Leu Ser Ser Gly
 50                  55                  60                 65 cct cag aac tgt gct gcc tgt gtt cac gag g gc ata tat gaa gaa ggc       297
Pro Gln Asn Cys Ala Ala Cys Val His Glu G ly Ile Tyr Glu Glu Gly
         70                  75                  80 att tct att tta gaa agc agt tcg gcc ttc c ca gat aat gct gcc cgc       345
Ile Ser Ile Leu Glu Ser Ser Ser Ala Phe P ro Asp Asn Ala Ala Arg
             85                  90                  95 agg gag gtg gag agc ctg ccg gcc gtc tgt c cc agt gat gga tgc acc       393
Arg Glu Val Glu Ser Leu Pro Ala Val Cys P ro Ser Asp Gly Cys Thr
100                 105                 110 tgg aag ggg acc ctg aaa gaa tac gag agc t gc cac gaa ggc cgc tgc       441
Trp Lys Gly Thr Leu Lys Glu Tyr Glu Ser C ys His Glu Gly Arg Cys
115                 120                 125 ccg ctc atg ctg acc gaa tgt ccc gcg tgt a aa ggc ctg gtc cgc ctt       489
Pro Leu Met Leu Thr Glu Cys Pro Ala Cys L ys Gly Leu Val Arg Leu
130                 135                 140                 145 ggt gaa aag gag cgc cac ctg gag cac gag t gc ccg gag aga agc ctg       537
Gly Glu Lys Glu Arg His Leu Glu His Glu C ys Pro Glu Arg Ser Leu
            150                 155                 160 agc tgc cgg cat tgc cgg gca ccc tgc tgc g ga gca gac gtg aag gcg       585
Ser Cys Arg His Cys Arg Ala Pro Cys Cys G ly Ala Asp Val Lys Ala
                165                 170                 175 cac cac gag gtc tgc ccc aag ttc ccc tta a ct tgt gac ggc tgc ggc       633
His His Glu Val Cys Pro Lys Phe Pro Leu T hr Cys Asp Gly Cys Gly
        180                 185                 190 aag aag aag atc ccc cgg gag aag ttt cag g ac cac gtc aag act tgt       681
Lys Lys Lys Ile Pro Arg Glu Lys Phe Gln A sp His Val Lys Thr Cys
    195                 200                 205 ggc aag tgt cga gtc cct tgc aga ttc cac g cc atc ggc tgc ctc gag       729
Gly Lys Cys Arg Val Pro Cys Arg Phe His A la Ile Gly Cys Leu Glu
210                 215                 220                 225 acg gta gag ggt gag aaa cag cag gag cac g ag gtg cag tgg ctg cgg       777
Thr Val Glu Gly Glu Lys Gln Gln Glu His G lu Val Gln Trp Leu Arg
            230                 235                 240 gag cac ctg gcc atg cta ctg agc tcg gtg c tg gag gca aag ccc ctc       825
Glu His Leu Ala Met Leu Leu Ser Ser Val L eu Glu Ala Lys Pro Leu
                245                 250                 255
```

```
ttg gga gac cag agc cac gcg ggg tca gag c tc ctg cag agg tgc gag        873
Leu Gly Asp Gln Ser His Ala Gly Ser Glu L eu Leu Gln Arg Cys Glu
            260                 265                 270 agc ctg gag aag aag acg gcc act ttt gag a ac att gtc tgc gtc ctg        921
Ser Leu Glu Lys Lys Thr Ala Thr Phe Glu A sn Ile Val Cys Val Leu
        275                 280                 285 aac cgg gag gtg gag agg gtg gcc atg act g cc gag gcc tgc agc cgg        969
Asn Arg Glu Val Glu Arg Val Ala Met Thr A la Glu Ala Cys Ser Arg
290                 295                 300                 305 cag cac cgg ctg gac caa gac aag att gaa g cc ctg agt agc aag gtg       1017
Gln His Arg Leu Asp Gln Asp Lys Ile Glu A la Leu Ser Ser Lys Val
                310                 315                 320 cag cag ctg gag agg agc att ggc ctc aag g ac ctg gcg atg gct gac       1065
Gln Gln Leu Glu Arg Ser Ile Gly Leu Lys A sp Leu Ala Met Ala Asp
            325                 330                 335 ttg gag cag aag gtc agg ccc ttc cag gcg c ag tgt ggc cac cgg tac       1113
Leu Glu Gln Lys Val Arg Pro Phe Gln Ala G ln Cys Gly His Arg Tyr
        340                 345                 350 tgc tcc ttc tgc ctg gcc agc atc ctc agg a ag ctc cag gaa gct gtg       1161
Cys Ser Phe Cys Leu Ala Ser Ile Leu Arg L ys Leu Gln Glu Ala Val
    355                 360                 365 gct ggc cgc ata ccc gcc atc ttc tcc cca g cc ttc tac acc agc agg       1209
Ala Gly Arg Ile Pro Ala Ile Phe Ser Pro A la Phe Tyr Thr Ser Arg
370                 375                 380                 385 tac ggc tac aag atg tgt ctg cgt atc tac c tg aac ggc gac ggc acc       1257
Tyr Gly Tyr Lys Met Cys Leu Arg Ile Tyr L eu Asn Gly Asp Gly Thr
                390                 395                 400 ggg cga gga aca cac ctg tcc ctc ttc ttt g tg gtg atg aag ggc ccg       1305
Gly Arg Gly Thr His Leu Ser Leu Phe Phe V al Val Met Lys Gly Pro
            405                 410                 415 aat gac gcc ctg ctg cgg tgg ccc ttc aac c ag aag gtg acc tta atg       1353
Asn Asp Ala Leu Leu Arg Trp Pro Phe Asn G ln Lys Val Thr Leu Met
        420                 425                 430 ctg ctc gac cag aat aac cgg gag cac gtg a tt gac gcc ttc agg ccc       1401
Leu Leu Asp Gln Asn Asn Arg Glu His Val I le Asp Ala Phe Arg Pro
    435                 440                 445 gac gtg act tca tcc tct ttt cag agg cca g tc aac gac atg aac atc       1449
Asp Val Thr Ser Ser Ser Phe Gln Arg Pro V al Asn Asp Met Asn Ile
450                 455                 460                 465 gca agc ggc tgc ccc ctc ttc tgc ccc gtc t cc aag atg gag gca aag       1497
Ala Ser Gly Cys Pro Leu Phe Cys Pro Val S er Lys Met Glu Ala Lys
                470                 475                 480 aat tcc tac gtg cgg gac gat gcc atc ttc a tc aag gcc att gtg gac       1545
Asn Ser Tyr Val Arg Asp Asp Ala Ile Phe I le Lys Ala Ile Val Asp
            485                 490                 495 ctg aca ggg ctc taa ctgccccta ctggtgtctg ggggttgg gg gcagccaggc        1600
Leu Thr Gly Leu
        500 acagccggct cacggagggg ccaccacgct gggccaggt ctcactgtac a agtgggcag      1660 ggcccccgct tgggcgcttg ggagggtgtc ggcctgcagc caagttcact g tcacggggg    1720 aaggagccac cagccagtcc tcagatttca gagactgcgg aggggcttgg c agacggtct   1780 tagccaaggg ctgtggtggc attggccgag ggtcttcggg tgcttcccag c acaagctgc   1840 ccttgctgtc ctgtgcagtg aagggagagg ccctgggtgg gggacactca g agtgggagc   1900 acatcccagc agtgcccatg tagcaggagc acagtggatg gccttgtgtc c ctcgggcat   1960 gacaggcaga aacgagggct gctccaggag aagggcctcc tgctggccag a gcaaggaag   2020 gctgagcagc ttggttctcc cctctggccc ctggagagaa gggagcattc c tagacccct   2080
```

```
gggtgcttgt ctgcacagag ctctggtctg tgccaccttg gccaggctgg c tgtgggagg      2140 gtctggtccc acgccgcctc tgctcagaca ctgtgtggga gggcacagca c agctgcggg      2200 taaagtgtga gagcttgcca tccagctcac gaagacagag ttattaaacc a ttacaaatc      2260 tc                                                                      2262
```

<210> SEQ ID NO 3
<211> LENGTH: 2455
<212> TYPE: DNA
<213> ORGANISM: Homo sapiens
<220> FEATURE:
<221> NAME/KEY: CDS
<222> LOCATION: (218)..(1924)
<300> PUBLICATION INFORMATION:
<308> DATABASE ACCESSION NUMBER: U21092
<309> DATABASE ENTRY DATE: 1995-03-23

<400> SEQUENCE: 3

```
cgggggagcg cggcgcggcc gccgcgtgcg cgagccgggg ttgcagccca g ccgggactt      60 tccagccggc ggcagccgcg gcggtcgtcg gctcttcccc gccccccgtc a tggggcagc     120 ccggggagca gaacgctgcg gaccgcggcg gaggacgcgc ccggcgcccc t gagccggcc    180 gagcggcgac ggaccgcgag aactcctctt tcctaaa atg gag tcg agt aaa aag       235
                                         Met Glu Ser Ser Lys Lys
                                           1               5 atg gac tct cct ggc gcg ctg cag act aac c cg ccg cta aag ctg cac       283
Met Asp Ser Pro Gly Ala Leu Gln Thr Asn P ro Pro Leu Lys Leu His
         10                  15                  20 act gac cgt agt gct ggg acg cca gtt ttt g tc cct gaa caa gga ggt       331
Thr Asp Arg Ser Ala Gly Thr Pro Val Phe V al Pro Glu Gln Gly Gly
     25                  30                  35 tac aag gaa aag ttt gtg aag acc gtg gag g ac aag tac aag tgt gag       379
Tyr Lys Glu Lys Phe Val Lys Thr Val Glu A sp Lys Tyr Lys Cys Glu
 40                  45                  50 aag tgc cac ctg gtg ctg tgc agc ccg aag c ag acc gag tgt ggg cac       427
Lys Cys His Leu Val Leu Cys Ser Pro Lys G ln Thr Glu Cys Gly His
 55                  60                  65                  70 cgc ttc tgc gag agc tgc atg gcg gcc ctg c tg agc tct tca agt cca       475
Arg Phe Cys Glu Ser Cys Met Ala Ala Leu L eu Ser Ser Ser Ser Pro
                 75                  80                  85 aaa tgt aca gcg tgt caa gag agc atc gtt a aa gat aag gtg ttt aag       523
Lys Cys Thr Ala Cys Gln Glu Ser Ile Val L ys Asp Lys Val Phe Lys
             90                  95                 100 gat aat tgc tgc aag aga gaa att ctg gct c tt cag atc tat tgt cgg       571
Asp Asn Cys Cys Lys Arg Glu Ile Leu Ala L eu Gln Ile Tyr Cys Arg
        105                 110                 115 aat gaa agc aga ggt tgt gca gag cag tta a cg ctg gga cat ctg ctg       619
Asn Glu Ser Arg Gly Cys Ala Glu Gln Leu T hr Leu Gly His Leu Leu
    120                 125                 130 gtg cat tta aaa aat gat tgc cat ttt gaa g aa ctt cca tgt gtg cgt       667
Val His Leu Lys Asn Asp Cys His Phe Glu G lu Leu Pro Cys Val Arg
135                 140                 145                 150 cct gac tgc aaa gaa aag gtc ttg agg aaa g ac ctg cga gac cac gtg       715
Pro Asp Cys Lys Glu Lys Val Leu Arg Lys A sp Leu Arg Asp His Val
                155                 160                 165 gag aag gcg tgt aaa tac cgg gaa gcc aca t gc agc cac tgc aag agt       763
Glu Lys Ala Cys Lys Tyr Arg Glu Ala Thr C ys Ser His Cys Lys Ser
            170                 175                 180 cag gtt ccg atg atc gcg ctg cag aaa cac g aa gac acc gac tgt ccc       811
Gln Val Pro Met Ile Ala Leu Gln Lys His G lu Asp Thr Asp Cys Pro
```

|     |     |     |     |     |     |     |     |     |     |     |     |     |     |     |     |
|-----|-----|-----|-----|-----|-----|-----|-----|-----|-----|-----|-----|-----|-----|-----|-----|
|     |     |     | 185 |     |     |     |     | 190 |     |     |     |     | 195 |     |     |
| tgc | gtg | gtg | gtg | tcc | tgc | cct | cac | aag | tgc | a gc | gtc | cag | act | ctc | ctg | 859 |
| Cys | Val | Val | Val | Ser | Cys | Pro | His | Lys | Cys | S er | Val | Gln | Thr | Leu | Leu |
|     | 200 |     |     |     | 205 |     |     |     | 210 |     |     |     |     |     |     |
| agg | agc | gag | ttg | agt | gca | cac | ttg | tca | gag | t gt | gtc | aat | gcc | ccc | agc | 907 |
| Arg | Ser | Glu | Leu | Ser | Ala | His | Leu | Ser | Glu | C ys | Val | Asn | Ala | Pro | Ser |
| 215 |     |     |     | 220 |     |     |     | 225 |     |     |     |     | 230 |     |     |
| acc | tgt | agt | ttt | aag | cgc | tat | ggc | tgc | gtt | t tt | cag | ggg | aca | aac | cag | 955 |
| Thr | Cys | Ser | Phe | Lys | Arg | Tyr | Gly | Cys | Val | P he | Gln | Gly | Thr | Asn | Gln |
|     |     |     | 235 |     |     |     | 240 |     |     |     |     | 245 |     |     |     |
| cag | atc | aag | gcc | cac | gag | gcc | agc | tcc | gcc | g tg | cag | cac | gtc | aac | ctg | 1003 |
| Gln | Ile | Lys | Ala | His | Glu | Ala | Ser | Ser | Ala | V al | Gln | His | Val | Asn | Leu |
|     |     | 250 |     |     |     | 255 |     |     |     | 260 |     |     |     |     |     |
| ctg | aag | gag | tgg | agc | aac | tcg | ctc | gaa | aag | a ag | gtt | tcc | ttg | ttg | cag | 1051 |
| Leu | Lys | Glu | Trp | Ser | Asn | Ser | Leu | Glu | Lys | L ys | Val | Ser | Leu | Leu | Gln |
|     | 265 |     |     |     | 270 |     |     |     | 275 |     |     |     |     |     |     |
| aat | gaa | agt | gta | gaa | aaa | aac | aag | agc | ata | c aa | agt | ttg | cac | aat | cag | 1099 |
| Asn | Glu | Ser | Val | Glu | Lys | Asn | Lys | Ser | Ile | G ln | Ser | Leu | His | Asn | Gln |
| 280 |     |     |     | 285 |     |     |     | 290 |     |     |     |     |     |     |     |
| ata | tgt | agc | ttt | gaa | att | gaa | att | gag | aga | c aa | aag | gaa | atg | ctt | cga | 1147 |
| Ile | Cys | Ser | Phe | Glu | Ile | Glu | Ile | Glu | Arg | G ln | Lys | Glu | Met | Leu | Arg |
| 295 |     |     |     | 300 |     |     |     | 305 |     |     |     |     | 310 |     |     |
| aat | aat | gaa | tcc | aaa | atc | ctt | cat | tta | cag | c ga | gtg | atc | gac | agc | caa | 1195 |
| Asn | Asn | Glu | Ser | Lys | Ile | Leu | His | Leu | Gln | A rg | Val | Ile | Asp | Ser | Gln |
|     |     |     | 315 |     |     |     | 320 |     |     |     |     | 325 |     |     |     |
| gca | gag | aaa | ctg | aag | gag | ctt | gac | aag | gag | a tc | cgg | ccc | ttc | cgg | cag | 1243 |
| Ala | Glu | Lys | Leu | Lys | Glu | Leu | Asp | Lys | Glu | I le | Arg | Pro | Phe | Arg | Gln |
|     |     | 330 |     |     |     | 335 |     |     |     | 340 |     |     |     |     |     |
| aac | tgg | gag | gaa | gca | gac | agc | atg | aag | agc | a gc | gtg | gag | tcc | ctc | cag | 1291 |
| Asn | Trp | Glu | Glu | Ala | Asp | Ser | Met | Lys | Ser | S er | Val | Glu | Ser | Leu | Gln |
|     | 345 |     |     |     | 350 |     |     |     | 355 |     |     |     |     |     |     |
| aac | cgc | gtg | acc | gag | ctg | gag | agc | gtg | gac | a ag | agt | gcg | ggg | caa | gtg | 1339 |
| Asn | Arg | Val | Thr | Glu | Leu | Glu | Ser | Val | Asp | L ys | Ser | Ala | Gly | Gln | Val |
|     | 360 |     |     |     | 365 |     |     |     | 370 |     |     |     |     |     |     |
| gct | cgg | aac | aca | ggc | ctg | ctg | gag | tcc | cag | c tg | agc | cgg | cat | gac | cag | 1387 |
| Ala | Arg | Asn | Thr | Gly | Leu | Leu | Glu | Ser | Gln | L eu | Ser | Arg | His | Asp | Gln |
| 375 |     |     |     | 380 |     |     |     | 385 |     |     |     |     | 390 |     |     |
| atg | ctg | agt | gtg | cac | gac | atc | cgc | cta | gcc | g ac | atg | gac | ctg | cgc | ttc | 1435 |
| Met | Leu | Ser | Val | His | Asp | Ile | Arg | Leu | Ala | A sp | Met | Asp | Leu | Arg | Phe |
|     |     |     | 395 |     |     |     | 400 |     |     |     |     | 405 |     |     |     |
| cag | gtc | ctg | gag | acc | gcc | agc | tac | aat | gga | g tg | ctc | atc | tgg | aag | att | 1483 |
| Gln | Val | Leu | Glu | Thr | Ala | Ser | Tyr | Asn | Gly | V al | Leu | Ile | Trp | Lys | Ile |
|     |     | 410 |     |     |     | 415 |     |     |     | 420 |     |     |     |     |     |
| cgc | gac | tac | aag | cgg | cgg | aag | cag | gag | gcc | g tc | atg | ggg | aag | acc | ctg | 1531 |
| Arg | Asp | Tyr | Lys | Arg | Arg | Lys | Gln | Glu | Ala | V al | Met | Gly | Lys | Thr | Leu |
|     | 425 |     |     |     | 430 |     |     |     | 435 |     |     |     |     |     |     |
| tcc | ctt | tac | agc | cag | cct | ttc | tac | act | ggt | t ac | ttt | ggt | tat | aag | atg | 1579 |
| Ser | Leu | Tyr | Ser | Gln | Pro | Phe | Tyr | Thr | Gly | T yr | Phe | Gly | Tyr | Lys | Met |
|     | 440 |     |     |     | 445 |     |     |     | 450 |     |     |     |     |     |     |
| tgt | gcc | agg | gtc | tac | ctg | aac | ggg | gac | ggg | a tg | ggg | aag | ggg | acg | cac | 1627 |
| Cys | Ala | Arg | Val | Tyr | Leu | Asn | Gly | Asp | Gly | M et | Gly | Lys | Gly | Thr | His |
| 455 |     |     |     | 460 |     |     |     | 465 |     |     |     |     | 470 |     |     |
| ttg | tcg | ctg | ttt | ttt | gtc | atc | atg | cgt | gga | g aa | tat | gat | gcc | ctg | ctt | 1675 |
| Leu | Ser | Leu | Phe | Phe | Val | Ile | Met | Arg | Gly | G lu | Tyr | Asp | Ala | Leu | Leu |
|     |     |     | 475 |     |     |     | 480 |     |     |     |     | 485 |     |     |     |
| cct | tgg | ccg | ttt | aag | cag | aaa | gtg | aca | ctc | a tg | ctg | atg | gat | cag | ggg | 1723 |
| Pro | Trp | Pro | Phe | Lys | Gln | Lys | Val | Thr | Leu | M et | Leu | Met | Asp | Gln | Gly |
|     |     | 490 |     |     |     | 495 |     |     |     | 500 |     |     |     |     |     |
| tcc | tct | cga | cgt | cat | ttg | gga | gat | gca | ttc | a ag | ccc | gac | ccc | aac | agc | 1771 |

```
Ser Ser Arg Arg His Leu Gly Asp Ala Phe Lys Pro Asp Pro Asn Ser
        505                 510                 515 agc agc ttc aag aag ccc act gga gag atg a at atc gcc tct ggc tgc    1819
Ser Ser Phe Lys Lys Pro Thr Gly Glu Met Asn Ile Ala Ser Gly Cys
    520                 525                 530 cca gtc ttt gtg gcc caa act gtt cta gaa a at ggg aca tat att aaa    1867
Pro Val Phe Val Ala Gln Thr Val Leu Glu Asn Gly Thr Tyr Ile Lys
535                 540                 545                 550 gat gat aca att ttt att aaa gtc ata gtg g at act tcg gat ctg ccc    1915
Asp Asp Thr Ile Phe Ile Lys Val Ile Val Asp Thr Ser Asp Leu Pro
                555                 560                 565 gat ccc tga taagtagctg gggaggtgga tttagcagaa ggcaactc ct            1964
Asp Pro ctgggggatt tgaaccggtc tgtcttcact gaggtcctcg cgctcagaaa a ggaccttgt  2024 gagacggagg aagcggcaga aggcggacgc gtgccggcgg gaggagccac g cgtgagcac  2084 acctgacacg ttttataata gactagccac acttcactct gaagaattat t tatccttca  2144 acaagataaa tattgctgtc agagaaggtt ttcattttca ttttttaaaga t ctagttaat 2204 taaggtggaa aacatatatg ctaaacaaaa gaaacatgat ttttcttcct t aaacttgaa  2264 caccaaaaaa acacacacac acacacacgt ggggatagct ggacatgtca g catgttaag  2324 taaaaggaga atttatgaaa tagtaatgca attctgatat cttctttcta a aattcaaga  2384 gtgcaatttt gtttcaaata cagtatattg tctatttta aggcctccaa a aaaaaaaa    2444 aattccggcc g                                                        2455

<210> SEQ ID NO 4
<211> LENGTH: 1999
<212> TYPE: DNA
<213> ORGANISM: Homo sapiens
<220> FEATURE:
<221> NAME/KEY: CDS
<222> LOCATION: (86)..(1498)
<300> PUBLICATION INFORMATION:
<308> DATABASE ACCESSION NUMBER: X80200
<309> DATABASE ENTRY DATE: 1998-04-15

<400> SEQUENCE: 4
gccgggagcg ccgctccagc gaggcgcggg ctgtggggcc gccgcgtgcc t ggccccgct   60 cgcccgtgcc ggccgctcgc ccgcc atg cct ggc ttc gac tac aag ttc ctg    112
                              Met Pro Gly Phe Asp Tyr Lys Phe Leu
                                1               5 gag aag ccc aag cga cgg ctg ctg tgc cca c tg tgc ggg aag ccc atg    160
Glu Lys Pro Lys Arg Arg Leu Leu Cys Pro Leu Cys Gly Lys Pro Met
 10              15                  20                  25 cgc gag cct gtg cag gtt tcc acc tgc ggc c ac cgt ttc tgc gat acc    208
Arg Glu Pro Val Gln Val Ser Thr Cys Gly His Arg Phe Cys Asp Thr
                 30                  35                  40 tgc ctg cag gag ttc ctc agt gaa gga gtc t tc aag tgc cct gag gac    256
Cys Leu Gln Glu Phe Leu Ser Glu Gly Val Phe Lys Cys Pro Glu Asp
             45                  50                  55 cag ctt cct ctg gac tat gcc aag atc tac c ca gac ccg gag ctg gaa    304
Gln Leu Pro Leu Asp Tyr Ala Lys Ile Tyr Pro Asp Pro Glu Leu Glu
         60                  65                  70 gta caa gta ttg ggc ctg cct atc cgc tgc a tc cac agt gag gag ggc    352
Val Gln Val Leu Gly Leu Pro Ile Arg Cys Ile His Ser Glu Glu Gly
 75                  80                  85 tgc cgc tgg agt ggg cca cta cgt cat cta c ag ggc cac ctg aat acc    400
Cys Arg Trp Ser Gly Pro Leu Arg His Leu Gln Gly His Leu Asn Thr
 90                  95                 100                 105
```

```
tgc agc ttc aat gtc att ccc tgc cct aat c gc tgc ccc atg aag ctg      448
Cys Ser Phe Asn Val Ile Pro Cys Pro Asn A rg Cys Pro Met Lys Leu
            110                 115                 120 agc cgc cgt gat cta cct gca cac ttg cag c at gac tgc ccc aag cgg      496
Ser Arg Arg Asp Leu Pro Ala His Leu Gln H is Asp Cys Pro Lys Arg
        125                 130                 135 cgc ctc aag tgc gag ttt tgt ggc tgt gac t tc agt ggg gag gcc tat      544
Arg Leu Lys Cys Glu Phe Cys Gly Cys Asp P he Ser Gly Glu Ala Tyr
        140                 145                 150 gag agc cat gag ggt atg tgc ccc cag gag a gt gtc tac tgt gag aat      592
Glu Ser His Glu Gly Met Cys Pro Gln Glu S er Val Tyr Cys Glu Asn
    155                 160                 165 aag tgt ggt gcc cgc atg atg cgg ggg ctg c tg gcc cag cat gcc acc      640
Lys Cys Gly Ala Arg Met Met Arg Gly Leu L eu Ala Gln His Ala Thr
170                 175                 180                 185 tct gag tgc ccc aag cgc act cag ccc tgc a cc tac tgc act aag gag      688
Ser Glu Cys Pro Lys Arg Thr Gln Pro Cys T hr Tyr Cys Thr Lys Glu
                190                 195                 200 ttc gtc ttt gac acc atc cag agc cac cag t ac cag tgc cca agg ctg      736
Phe Val Phe Asp Thr Ile Gln Ser His Gln T yr Gln Cys Pro Arg Leu
            205                 210                 215 cct gtt gcc tgc ccc aac caa tgt ggt gtg g gc act gtg gct cgg gag      784
Pro Val Ala Cys Pro Asn Gln Cys Gly Val G ly Thr Val Ala Arg Glu
        220                 225                 230 gac ctg cca ggc cat ctg aag gac agc tgt a ac acc gcc ctg gtg ctc      832
Asp Leu Pro Gly His Leu Lys Asp Ser Cys A sn Thr Ala Leu Val Leu
        235                 240                 245 tgc cca ttc aaa gac tcc ggc tgc aag cac a gg tgc cct aag ctg gca      880
Cys Pro Phe Lys Asp Ser Gly Cys Lys His A rg Cys Pro Lys Leu Ala
250                 255                 260                 265 atg gca cgg cat gtg gag gag agt gtg aag c ca cat ctg gcc atg atg      928
Met Ala Arg His Val Glu Glu Ser Val Lys P ro His Leu Ala Met Met
                270                 275                 280 tgt gcc ctg gtg agc cgg caa cgg cag gag c tg cag gag ctt cgg cga      976
Cys Ala Leu Val Ser Arg Gln Arg Gln Glu L eu Gln Glu Leu Arg Arg
            285                 290                 295 gag ctg gag gag cta tca gtg ggc agt gat g gc gtg ctc atc tgg aag     1024
Glu Leu Glu Glu Leu Ser Val Gly Ser Asp G ly Val Leu Ile Trp Lys
        300                 305                 310 att ggc agc tat gga cgg cgg cta cag gag g cc aag gcc aag ccc aac     1072
Ile Gly Ser Tyr Gly Arg Arg Leu Gln Glu A la Lys Ala Lys Pro Asn
        315                 320                 325 ctt gag tgc ttc agc cca gcc ttc tac aca c at aag tat ggt tac aag     1120
Leu Glu Cys Phe Ser Pro Ala Phe Tyr Thr H is Lys Tyr Gly Tyr Lys
330                 335                 340                 345 ctg cag gtg tct gca ttc ctc aat ggc aat g gc agt ggt gag ggc aca     1168
Leu Gln Val Ser Ala Phe Leu Asn Gly Asn G ly Ser Gly Glu Gly Thr
                350                 355                 360 cac ctc tca ctg tac att cgt gtg ctg cct g gt gcc ttt gac aat ctc     1216
His Leu Ser Leu Tyr Ile Arg Val Leu Pro G ly Ala Phe Asp Asn Leu
            365                 370                 375 ctt gag tgg ccc ttt gcc cgc cgt gtc acc t tc tcc ctg ctg gat cag     1264
Leu Glu Trp Pro Phe Ala Arg Arg Val Thr P he Ser Leu Leu Asp Gln
        380                 385                 390 agc gac cct ggg ctg gct aaa cca cag cac g tc act gag acc ttc cac     1312
Ser Asp Pro Gly Leu Ala Lys Pro Gln His V al Thr Glu Thr Phe His
395                 400                 405 ccc gac cca aac tgg aag aat ttc cag aag c ca ggc acg tgg cgg ggc     1360
Pro Asp Pro Asn Trp Lys Asn Phe Gln Lys P ro Gly Thr Trp Arg Gly
```

-continued

| | | |
|---|---|---|
| 410 | 415 | 420 | 425 |

| | |
|---|---|
| tcc ctg gat gag agt tct ctg ggc ttt ggt t at ccc aag ttc atc tcc<br>Ser Leu Asp Glu Ser Ser Leu Gly Phe Gly T yr Pro Lys Phe Ile Ser<br>430                435                440 | 1408 |
| cac cag gac att cga aag cga aac tat gtg c gg gat gat gca gtc ttc<br>His Gln Asp Ile Arg Lys Arg Asn Tyr Val A rg Asp Asp Ala Val Phe<br>    445                450                455 | 1456 |
| atc cgt gct gct gtt gaa ctg ccc cgg aag a tc ctc agc tga<br>Ile Arg Ala Ala Val Glu Leu Pro Arg Lys I le Leu Ser<br>460                465                470 | 1498 |
| gtgcaggtgg ggttcgaggg gaaaggacga tgggcatga cctcagtcag g cactggctg | 1558 |
| aacttggaga gggggccgga ccccgtcag ctgcttctgc tgcctaggtt c tgttacccc | 1618 |
| atcctcccctc ccccagccac caccctcagg tgcctccaat tggtgcttca g ccctggccc | 1678 |
| ctgtggggaa caggtcttgg ggtcatgaag ggctggaaac aagtgacccc a gggcctgtc | 1738 |
| tcccttcttg ggtagggcag acatgccttg gtgccggtca cactctacac g gactgaggt | 1798 |
| gcctgctcag gtgctatgtc ccaagagcca taaggggtg ggaattgggg a gggagaaag | 1858 |
| ggtagttcaa agagtctgtc ttgagatctg attttttccc cctttaccta g ctgtgcccc | 1918 |
| ctctggttat ttatttcctt agtgccagga gggcacagca ggggagccct g attttaat | 1978 |
| aaatccggaa ttgtatttat t | 1999 |

<210> SEQ ID NO 5
<211> LENGTH: 3993
<212> TYPE: DNA
<213> ORGANISM: Homo sapiens
<220> FEATURE:
<221> NAME/KEY: CDS
<222> LOCATION: (55)..(1728)
<300> PUBLICATION INFORMATION:
<308> DATABASE ACCESSION NUMBER: AB000509
<309> DATABASE ENTRY DATE: 1998-03-25

<400> SEQUENCE: 5

| | |
|---|---|
| gcagcagccg cgcctgcaga ccggcctcgc ggagcccgcg cgccgagccc c aca atg<br>                                                                Met<br>                                                                 1 | 57 |
| gct tat tca gaa gag cat aaa ggt atg ccc t gt ggt ttc atc cgc cag<br>Ala Tyr Ser Glu Glu His Lys Gly Met Pro C ys Gly Phe Ile Arg Gln<br>        5                10                15 | 105 |
| aat tcc ggc aac tcc att tcc ttg gac ttt g ag ccc agt ata gag tac<br>Asn Ser Gly Asn Ser Ile Ser Leu Asp Phe G lu Pro Ser Ile Glu Tyr<br>    20                25                30 | 153 |
| cag ttt gtg gag cgg ttg gaa gag cgc tac a aa tgt gcc ttc tgc cac<br>Gln Phe Val Glu Arg Leu Glu Glu Arg Tyr L ys Cys Ala Phe Cys His<br>35                40                45 | 201 |
| tcg gtg ctt cac aac ccc cac cag aca gga t gt ggg cac cgc ttc tgc<br>Ser Val Leu His Asn Pro His Gln Thr Gly C ys Gly His Arg Phe Cys<br>50                55                60                65 | 249 |
| cag cac tgc atc ctg tcc ctg aga gaa tta a ac aca gtg cca atc tgc<br>Gln His Cys Ile Leu Ser Leu Arg Glu Leu A sn Thr Val Pro Ile Cys<br>        70                75                80 | 297 |
| cct gta gat aaa gag gtc atc aaa tct cag g ag gtt ttt aaa gac aat<br>Pro Val Asp Lys Glu Val Ile Lys Ser Gln G lu Val Phe Lys Asp Asn<br>    85                90                95 | 345 |
| tgt tgc aaa aga gaa gtc ctc aac tta tat g ta tat tgc agc aat gct<br>Cys Cys Lys Arg Glu Val Leu Asn Leu Tyr V al Tyr Cys Ser Asn Ala<br>100                105                110 | 393 |
| cct gga tgt aat gcc aag gtt att ctg ggc c gg tac cag gat cac ctt | 441 |

```
Pro Gly Cys Asn Ala Lys Val Ile Leu Gly A rg Tyr Gln Asp His Leu
    115                 120                 125 cag cag tgc tta ttt caa cct gtg cag tgt t ct aat gag aag tgc cgg       489
Gln Gln Cys Leu Phe Gln Pro Val Gln Cys S er Asn Glu Lys Cys Arg
130             135                 140                 145 gag cca gtc cta cgg aaa gac ctg aaa gag c at ttg agt gca tcc tgt       537
Glu Pro Val Leu Arg Lys Asp Leu Lys Glu H is Leu Ser Ala Ser Cys
                150                 155                 160 cag ttt cga aag gaa aaa tgc ctt tat tgc a aa aag gat gtg gta gtc       585
Gln Phe Arg Lys Glu Lys Cys Leu Tyr Cys L ys Lys Asp Val Val Val
            165                 170                 175 atc aat cta cag aat cat gag gaa aac ttg t gt cct gaa tac cca gta       633
Ile Asn Leu Gln Asn His Glu Glu Asn Leu C ys Pro Glu Tyr Pro Val
        180                 185                 190 ttt tgt ccc aac aat tgt gcg aag att att c ta aaa act gag gta gat       681
Phe Cys Pro Asn Asn Cys Ala Lys Ile Ile L eu Lys Thr Glu Val Asp
    195                 200                 205 gaa cac ctg gct gta tgt cct gaa gct gag c aa gac tgt cct ttt aag       729
Glu His Leu Ala Val Cys Pro Glu Ala Glu G ln Asp Cys Pro Phe Lys
210             215                 220                 225 cac tat ggc tgt gct gta acg gat aaa cgg a gg aac ctg cag caa cat       777
His Tyr Gly Cys Ala Val Thr Asp Lys Arg A rg Asn Leu Gln Gln His
                230                 235                 240 gag cat tca gcc tta cgg gag cac atg cgt t tg gtt tta gaa aag aat       825
Glu His Ser Ala Leu Arg Glu His Met Arg L eu Val Leu Glu Lys Asn
            245                 250                 255 gtc caa tta gaa gaa cag att tct gac tta c ac aag agc cta gaa cag       873
Val Gln Leu Glu Glu Gln Ile Ser Asp Leu H is Lys Ser Leu Glu Gln
        260                 265                 270 aaa gaa agt aaa atc cag cag cta gca gaa a ct ata aag aaa ctt gaa       921
Lys Glu Ser Lys Ile Gln Gln Leu Ala Glu T hr Ile Lys Lys Leu Glu
    275                 280                 285 aag gag ttc aag cag ttt gca cag ttg ttt g gc aaa aat gga agc ttc       969
Lys Glu Phe Lys Gln Phe Ala Gln Leu Phe G ly Lys Asn Gly Ser Phe
290             295                 300                 305 ctc cca aac atc cag gtt ttt gcc agt cac a tt gac aag tca gct tgg      1017
Leu Pro Asn Ile Gln Val Phe Ala Ser His I le Asp Lys Ser Ala Trp
                310                 315                 320 cta gaa gct caa gtg cat caa tta tta caa a tg gtt aac cag caa caa      1065
Leu Glu Ala Gln Val His Gln Leu Leu Gln M et Val Asn Gln Gln Gln
            325                 330                 335 aat aaa ttt gac ctg aga cct ttg atg gaa g ca gtt gat aca gtg aaa      1113
Asn Lys Phe Asp Leu Arg Pro Leu Met Glu A la Val Asp Thr Val Lys
        340                 345                 350 cag aaa att acc ctg cta gaa aac aat gat c aa aga tta gcc gtt tta      1161
Gln Lys Ile Thr Leu Leu Glu Asn Asn Asp G ln Arg Leu Ala Val Leu
    355                 360                 365 gaa gag gaa act aac aaa cat gat acc cac a tt aat att cat aaa gca      1209
Glu Glu Glu Thr Asn Lys His Asp Thr His I le Asn Ile His Lys Ala
370             375                 380                 385 cag ctg agt aaa aat gaa gag cga ttt aaa c tg ctg gag ggt act tgc      1257
Gln Leu Ser Lys Asn Glu Glu Arg Phe Lys L eu Leu Glu Gly Thr Cys
                390                 395                 400 tat aat gga aag ctc att tgg aag gtg aca g at tac aag atg aag aag      1305
Tyr Asn Gly Lys Leu Ile Trp Lys Val Thr A sp Tyr Lys Met Lys Lys
            405                 410                 415 aga gag gcg gtg gat ggg cac aca gtg tcc a tc ttc agc cag tcc ttc      1353
Arg Glu Ala Val Asp Gly His Thr Val Ser I le Phe Ser Gln Ser Phe
        420                 425                 430
```

```
tac acc agc cgc tgt ggc tac cgg ctc tgt g ct aga gca tac ctg aat    1401
Tyr Thr Ser Arg Cys Gly Tyr Arg Leu Cys A la Arg Ala Tyr Leu Asn
            435                 440                 445 ggg gat ggg tca ggg agg ggg tca cac ctg t cc cta tac ttt gtg gtc    1449
Gly Asp Gly Ser Gly Arg Gly Ser His Leu S er Leu Tyr Phe Val Val
450                 455                 460                 465 atg cga gga gag ttt gac tca ctg ttg cag t gg cca ttc agg cag agg    1497
Met Arg Gly Glu Phe Asp Ser Leu Leu Gln T rp Pro Phe Arg Gln Arg
                470                 475                 480 gtg acc ctg atg ctt ctg gac cag agt ggc a aa aag aac att atg gag    1545
Val Thr Leu Met Leu Leu Asp Gln Ser Gly L ys Lys Asn Ile Met Glu
            485                 490                 495 acc ttc aaa cct gac ccc aat agc agc agc t tt aaa aga cct gat ggg    1593
Thr Phe Lys Pro Asp Pro Asn Ser Ser Ser P he Lys Arg Pro Asp Gly
        500                 505                 510 gag atg aac att gca tct ggc tgt ccc cgc t tt gtg gct cat tct gtt    1641
Glu Met Asn Ile Ala Ser Gly Cys Pro Arg P he Val Ala His Ser Val
    515                 520                 525 ttg gag aat gcc aag aac gcc tac att aaa g at gac act ctg ttc ttg    1689
Leu Glu Asn Ala Lys Asn Ala Tyr Ile Lys A sp Asp Thr Leu Phe Leu
530                 535                 540                 545 aaa gtg gcc gtg gac tta act gac ctg gag g at ctc tag tcactgttat    1738
Lys Val Ala Val Asp Leu Thr Asp Leu Glu A sp Leu
                550                 555 ggggtgataa gaggacttct tggggccaga actgtggagg agcacatt t gattatcat    1798
attgacctgg atttagactc aaagcacatt tgtatttgcc tttttcctta a cgtttgaag    1858
tcagtttaaa acttctgaag tgctgtcttt ttacatttta ctctgtccca g tttgaaact    1918
taaaactctt agaatattct cttattattt atatttttat atttcttgaa a gatggtaag    1978
tttcttgaag tttttggggc gtttctcttt tactggtgct tagcgcagtg t ctcgggcac    2038
tctaaatatt gagtgttatg gaggacacag aggtagcaga atcccagttg a aaatgtttt    2098
gatattttat tgtttggcct attgattcta gacctggcct taagtctgca a aagccatct    2158
ttataaggta ggctgttcca gttaagaagt gggtgatgta gttacaaaga t aatatgctc    2218
agtttggacc ttttttttcag ttaaatgcta aatatatgaa aattactata c ctctaagta    2278
ttttcatgaa attcaccagc agtttgcaag cacagttttg caaggctgca t aagaactgg    2338
tgaatggggt aagcattttc attcttcctg ctgaagtaaa gcagaaagta c tgcatagta    2398
tatgagatat agccagctag ctaaagttca gattttgtta ggttcaaccc t atgaaaaaa    2458
actattttca taggtcaaaa atggtaaaaa attagcagtt tcataagatt c aaccaaata    2518
aatatatata tacacacaca catacatata cacctatata tgtgtgtata c aaacagttc    2578
gaatgtattt tggtgacagt aataaatcaa tgtgaggatg atagaattt a gtatatgat    2638
agagaaaatg tcataaatgg ataaaaggaa tttacaactt gaggagaaaa c ctttacaat    2698
ttcctatggg tgtcagaagt actctcagcg aaaactgatg gctaaaacag t atctactat    2758
tctctgataa cttttttttt gagacagagt ttcattgtca cccaggctgg a gtacagtgg    2818
catgatctca gctcactgca aactctgcct cccgaattca agtgattctc c tgcctcagc    2878
ctcctgagta gctgggatta caggcgcccg tcaccacacc caggtaattt t tgtattttt    2938
agtagagacg gagttttgcc atgttggcca agctgatctc aaactcctga c ctcaagtga    2998
tctgcccgcc tcggcctccc aaagtgctga gattacaggc atgacccacc g cgtcaagcc    3058
tctgacaact attgaatttg taagctgcta tgcaaatggg catttatata a acttgtgat    3118
gtttcttgtc agaattctga gtactctgtg aagaacagaa atgatcatat t cttatgcat    3178
```

-continued

```
ctatctgtat gggtctgaag gtgtatatac aaactgagat gagtccttat g actcttgat    3238 aagcctgagt ttaacaacaa caaaaatgcc aagttgtcct gagcccttct g cgttgttat    3298 gccacttccc tactgctcat atgcacgctg gctcccctgg gcacgcaagg a tgagtatgg    3358 gccatgggcc cctgtagagc tgcttacctg tgatgacca tgcaccttac a atttctgaa    3418 cagttaaccc tatagaagca tgctttatat gagtgtcttc tgggaagagg a accttctta    3478 atctcttctg tgggattttc aaaatgctaa agactcacac tgcagcaatc a tcccagatg    3538 attaaattca agaaatagg ttcacaacag gaatatactg aagaactaga g tgtcactgc    3598 tggtgaactg tggcacggtt gctcaacaca tcacctcgga caaattcagg a agcatttct    3658 ttagcccaca agtccagacc caggtgctct gtatgtttgt ttttaatatt c atcatatcc    3718 aagttcactc tgtcttcctg agcagtggaa gatcatattg ctgtaacttc t tttaagtag    3778 ttgatgtgga aaacatttta aagtgaattt gtcaaaatgc tggttttgtg t tttatccaa    3838 cttttgtgca tatatataaa gtatgtcatg gcatggtttg cttaggagtt c agagttcct    3898 tcatcatcga aatagtgatt aagtgatccc agaacaagga atactagagt a aaaagcacc    3958 tcttttttcag aaaaaaaaaa aaaaaaaaaa aaaaa                              3993
```

<210> SEQ ID NO 6
<211> LENGTH: 2264
<212> TYPE: DNA
<213> ORGANISM: Homo sapiens
<220> FEATURE:
<221> NAME/KEY: CDS
<222> LOCATION: (222)..(1790)
<300> PUBLICATION INFORMATION:
<308> DATABASE ACCESSION NUMBER: U78798
<309> DATABASE ENTRY DATE: 1996-12-12

<400> SEQUENCE: 6

```
ccgcagctgg ggcttggcct gcgggcggcc agcgaaggtg gcgaaggctc c cactggatc     60 cagagtttgc cgtccaagca gcctcgtctc ggcgcgcagt gtctgtgtcc g tcctctacc    120 agcgccttgg ctgagcggag tcgtgcggtt ggtggggag ccctgccctc c tggttcggc    180 ctccccgcgc actagaacga gcaagtgata atcaagttac t atg agt   ctg cta aac   236
                                              Met Ser Leu Leu Asn
                                                1               5 tgt gaa aac agc tgt gga tcc agc cag tct g aa agt gac tgc tgt gtg     284
Cys Glu Asn Ser Cys Gly Ser Ser Gln Ser G lu Ser Asp Cys Cys Val
             10                  15                  20 gcc atg gcc agc tcc tgt agc gct gta aca a aa gat gat agt gtg ggt     332
Ala Met Ala Ser Ser Cys Ser Ala Val Thr L ys Asp Asp Ser Val Gly
         25                  30                  35 gga act gcc agc acg ggg aac ctc tcc agc t ca ttt atg gag gag atc    380
Gly Thr Ala Ser Thr Gly Asn Leu Ser Ser S er Phe Met Glu Glu Ile
     40                  45                  50 cag gga tat gat gta gag ttt gac cca ccc c tg gaa agc aag tat gaa    428
Gln Gly Tyr Asp Val Glu Phe Asp Pro Pro L eu Glu Ser Lys Tyr Glu
 55                  60                  65 tgc ccc atc tgc ttg atg gca tta cga gaa g ca gtg caa acg cca tgc    476
Cys Pro Ile Cys Leu Met Ala Leu Arg Glu A la Val Gln Thr Pro Cys
 70                  75                  80                  85 ggc cat agg ttc tgc aaa gcc tgc atc ata a aa tca ata agg gat gca    524
Gly His Arg Phe Cys Lys Ala Cys Ile Ile L ys Ser Ile Arg Asp Ala
         90                  95                 100 ggt cac aaa tgt cca gtt gac aat gaa ata c tg ctg gaa aat caa cta    572
Gly His Lys Cys Pro Val Asp Asn Glu Ile L eu Leu Glu Asn Gln Leu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 105 |     |     |     | 110 |     |     |     | 115 |     |     |     |     |     |      |
| ttt | cca | gac | aat | ttt | gca | aaa | cgt | gag | att | c tt | tct | ctg | atg | gtg | aaa | 620  |
| Phe | Pro | Asp | Asn | Phe | Ala | Lys | Arg | Glu | Ile | L eu | Ser | Leu | Met | Val | Lys |      |
|     |     | 120 |     |     |     | 125 |     |     |     | 130 |     |     |     |     |     |      |
| tgt | cca | aat | gaa | ggt | tgt | ttg | cac | aag | atg | g aa | ctg | aga | cat | ctt | gag | 668  |
| Cys | Pro | Asn | Glu | Gly | Cys | Leu | His | Lys | Met | G lu | Leu | Arg | His | Leu | Glu |      |
|     |     | 135 |     |     |     | 140 |     |     |     | 145 |     |     |     |     |     |      |
| gat | cat | caa | gca | cat | tgt | gag | ttt | gct | ctt | a tg | gat | tgt | ccc | caa | tgc | 716  |
| Asp | His | Gln | Ala | His | Cys | Glu | Phe | Ala | Leu | M et | Asp | Cys | Pro | Gln | Cys |      |
| 150 |     |     |     | 155 |     |     |     | 160 |     |     |     |     | 165 |     |     |      |
| cag | cgt | ccc | ttc | caa | aaa | ttc | cat | att | aat | a tt | cac | att | ctg | aag | gat | 764  |
| Gln | Arg | Pro | Phe | Gln | Lys | Phe | His | Ile | Asn | I le | His | Ile | Leu | Lys | Asp |      |
|     |     | 170 |     |     |     | 175 |     |     |     | 180 |     |     |     |     |     |      |
| tgt | cca | agg | aga | cag | gtt | tct | tgt | gac | aac | t gt | gct | gca | tca | atg | gca | 812  |
| Cys | Pro | Arg | Arg | Gln | Val | Ser | Cys | Asp | Asn | C ys | Ala | Ala | Ser | Met | Ala |      |
|     |     | 185 |     |     |     | 190 |     |     |     | 195 |     |     |     |     |     |      |
| ttt | gaa | gat | aaa | gag | atc | cat | gac | cag | aac | t gt | cct | ttg | gca | aat | gtc | 860  |
| Phe | Glu | Asp | Lys | Glu | Ile | His | Asp | Gln | Asn | C ys | Pro | Leu | Ala | Asn | Val |      |
|     |     | 200 |     |     |     | 205 |     |     |     | 210 |     |     |     |     |     |      |
| atc | tgt | gaa | tac | tgc | aat | act | ata | ctc | atc | a ga | gaa | cag | atg | cct | aat | 908  |
| Ile | Cys | Glu | Tyr | Cys | Asn | Thr | Ile | Leu | Ile | A rg | Glu | Gln | Met | Pro | Asn |      |
| 215 |     |     |     | 220 |     |     |     | 225 |     |     |     |     |     |     |     |      |
| cat | tat | gat | cta | gac | tgc | cct | aca | gcc | cca | a tt | cca | tgc | aca | ttc | agt | 956  |
| His | Tyr | Asp | Leu | Asp | Cys | Pro | Thr | Ala | Pro | I le | Pro | Cys | Thr | Phe | Ser |      |
| 230 |     |     |     | 235 |     |     |     | 240 |     |     |     |     | 245 |     |     |      |
| act | ttt | ggt | tgc | cat | gaa | aag | atg | cag | agg | a at | cac | ttg | gca | cgc | cac | 1004 |
| Thr | Phe | Gly | Cys | His | Glu | Lys | Met | Gln | Arg | A sn | His | Leu | Ala | Arg | His |      |
|     |     | 250 |     |     |     | 255 |     |     |     | 260 |     |     |     |     |     |      |
| cta | caa | gag | aac | acc | cag | tca | cac | atg | aga | a tg | ttg | gcc | cag | gct | gtt | 1052 |
| Leu | Gln | Glu | Asn | Thr | Gln | Ser | His | Met | Arg | M et | Leu | Ala | Gln | Ala | Val |      |
|     |     | 265 |     |     |     | 270 |     |     |     | 275 |     |     |     |     |     |      |
| cat | agt | ttg | agc | gtt | ata | ccc | gac | tct | ggg | t at | atc | tca | gag | gtc | cgg | 1100 |
| His | Ser | Leu | Ser | Val | Ile | Pro | Asp | Ser | Gly | T yr | Ile | Ser | Glu | Val | Arg |      |
|     |     | 280 |     |     |     | 285 |     |     |     | 290 |     |     |     |     |     |      |
| aat | ttc | cag | gaa | act | att | cac | cag | tta | gag | g gt | cgc | ctt | gta | aga | caa | 1148 |
| Asn | Phe | Gln | Glu | Thr | Ile | His | Gln | Leu | Glu | G ly | Arg | Leu | Val | Arg | Gln |      |
|     |     | 295 |     |     |     | 300 |     |     |     | 305 |     |     |     |     |     |      |
| gac | cat | caa | atc | cgg | gag | ctg | act | gct | aaa | a tg | gaa | act | cag | agt | atg | 1196 |
| Asp | His | Gln | Ile | Arg | Glu | Leu | Thr | Ala | Lys | M et | Glu | Thr | Gln | Ser | Met |      |
| 310 |     |     |     | 315 |     |     |     | 320 |     |     |     |     | 325 |     |     |      |
| tat | gta | agt | gag | ctc | aaa | cga | acc | att | cga | a cc | ctt | gag | gac | aaa | gtt | 1244 |
| Tyr | Val | Ser | Glu | Leu | Lys | Arg | Thr | Ile | Arg | T hr | Leu | Glu | Asp | Lys | Val |      |
|     |     | 330 |     |     |     | 335 |     |     |     | 340 |     |     |     |     |     |      |
| gct | gaa | atc | gaa | gca | cag | cag | tgc | aat | gga | a tt | tat | att | tgg | aag | att | 1292 |
| Ala | Glu | Ile | Glu | Ala | Gln | Gln | Cys | Asn | Gly | I le | Tyr | Ile | Trp | Lys | Ile |      |
|     |     | 345 |     |     |     | 350 |     |     |     | 355 |     |     |     |     |     |      |
| ggc | aac | ttt | gga | atg | cat | ttg | aaa | tgt | caa | g aa | gag | gag | aaa | cct | gtt | 1340 |
| Gly | Asn | Phe | Gly | Met | His | Leu | Lys | Cys | Gln | G lu | Glu | Glu | Lys | Pro | Val |      |
|     |     | 360 |     |     |     | 365 |     |     |     | 370 |     |     |     |     |     |      |
| gtg | att | cat | agc | cct | gga | ttc | tac | act | ggc | a aa | ccc | ggg | tac | aaa | ctg | 1388 |
| Val | Ile | His | Ser | Pro | Gly | Phe | Tyr | Thr | Gly | L ys | Pro | Gly | Tyr | Lys | Leu |      |
|     |     | 375 |     |     |     | 380 |     |     |     | 385 |     |     |     |     |     |      |
| tgc | atg | cgc | ttg | cac | ctt | cag | tta | ccg | act | g ct | cag | cgc | tgt | gca | aac | 1436 |
| Cys | Met | Arg | Leu | His | Leu | Gln | Leu | Pro | Thr | A la | Gln | Arg | Cys | Ala | Asn |      |
| 390 |     |     |     | 395 |     |     |     | 400 |     |     |     |     | 405 |     |     |      |
| tat | ata | tcc | ctt | ttt | gtc | cac | aca | atg | caa | g ga | gaa | tat | gac | agc | cac | 1484 |
| Tyr | Ile | Ser | Leu | Phe | Val | His | Thr | Met | Gln | G ly | Glu | Tyr | Asp | Ser | His |      |
|     |     | 410 |     |     |     | 415 |     |     |     | 420 |     |     |     |     |     |      |
| ctc | cct | tgg | ccc | ttc | cag | ggt | aca | ata | cgc | c tt | aca | att | ctt | gat | cag | 1532 |

```
                                          -continued

Leu Pro Trp Pro Phe Gln Gly Thr Ile Arg L eu Thr Ile Leu Asp Gln
            425                 430                 435 tct gaa gca cct gta agg caa aac cac gaa g ag ata atg gat gcc aaa    1580
Ser Glu Ala Pro Val Arg Gln Asn His Glu G lu Ile Met Asp Ala Lys
            440                 445                 450 cca gag ctg ctt gct ttc cag cga ccc aca a tc cca cgg aac cca aaa    1628
Pro Glu Leu Leu Ala Phe Gln Arg Pro Thr I le Pro Arg Asn Pro Lys
            455                 460                 465 ggt ttt ggc tat gta act ttt atg cat ctg g aa gcc cta aga caa aga    1676
Gly Phe Gly Tyr Val Thr Phe Met His Leu G lu Ala Leu Arg Gln Arg
470             475                 480                 485 act ttc att aag gat gac aca tta tta gtg c gc tgt gag gtc tcc acc    1724
Thr Phe Ile Lys Asp Asp Thr Leu Leu Val A rg Cys Glu Val Ser Thr
                490                 495                 500 cgc ttt gac atg ggt agc ctt cgg agg gag g gt ttt cag cca cga agt    1772
Arg Phe Asp Met Gly Ser Leu Arg Arg Glu G ly Phe Gln Pro Arg Ser
                505                 510                 515 act gat gca ggg gta tag cttgccctca cttgctcaaa a acaactacc           1820
Thr Asp Ala Gly Val
        520 tggagaaaac agtgcctttc cttgccctgt tctcaataac atgcaaacaa a caagccacg  1880 ggaaatatgt aatatctact agtgagtgtt gttagagagg tcacttacta t ttcttcctg  1940 ttacaaatga tctgaggcag ttttttcctg ggaatccaca cgttccatgc t ttttcagaa  2000 atgttaggcc tgaagtgcct gtggcatgtt gcagcagcta ttttgccagt t agtatacct  2060 ctttgttgta ctttcttggg cttttgctct ggtgtatttt attgtcagaa a gtccagact  2120 caagagtact aaacttttaa taataatgga ttttccttaa aacttcagtc t ttttgtagt  2180 attatatgta atatattaaa agtgaaaatc actaccgcct tgaaaaaaaa a aaaaaaaaa  2240 ctcgaggggg gcccgtaccc aatg                                         2264

<210> SEQ ID NO 7
<211> LENGTH: 18
<212> TYPE: DNA
<213> ORGANISM: Artificial Sequence
<220> FEATURE:
<223> OTHER INFORMATION: antisense sequence

<400> SEQUENCE: 7
tttaagttgc tccagggc                                                  18

<210> SEQ ID NO 8
<211> LENGTH: 18
<212> TYPE: DNA
<213> ORGANISM: Artificial Sequence
<220> FEATURE:
<223> OTHER INFORMATION: antisense sequence

<400> SEQUENCE: 8
gccgggcgag gactgctg                                                  18

<210> SEQ ID NO 9
<211> LENGTH: 18
<212> TYPE: DNA
<213> ORGANISM: Artificial Sequence
<220> FEATURE:
<223> OTHER INFORMATION: antisense sequence

<400> SEQUENCE: 9
gcagacggtg ggagggca                                                  18
```

```
<210> SEQ ID NO 10
<211> LENGTH: 18
<212> TYPE: DNA
<213> ORGANISM: Artificial Sequence
<220> FEATURE:
<223> OTHER INFORMATION: antisense sequence

<400> SEQUENCE: 10
ctgggctcct ttgggtcc                                                 18

<210> SEQ ID NO 11
<211> LENGTH: 18
<212> TYPE: DNA
<213> ORGANISM: Artificial Sequence
<220> FEATURE:
<223> OTHER INFORMATION: antisense sequence

<400> SEQUENCE: 11
cacagcagag agccctgg                                                 18

<210> SEQ ID NO 12
<211> LENGTH: 18
<212> TYPE: DNA
<213> ORGANISM: Artificial Sequence
<220> FEATURE:
<223> OTHER INFORMATION: antisense sequence

<400> SEQUENCE: 12
attcctcggg ttctcaga                                                 18

<210> SEQ ID NO 13
<211> LENGTH: 18
<212> TYPE: DNA
<213> ORGANISM: Artificial Sequence
<220> FEATURE:
<223> OTHER INFORMATION: antisense sequence

<400> SEQUENCE: 13
ccattcctcg ggttctca                                                 18

<210> SEQ ID NO 14
<211> LENGTH: 18
<212> TYPE: DNA
<213> ORGANISM: Artificial Sequence
<220> FEATURE:
<223> OTHER INFORMATION: antisense sequence

<400> SEQUENCE: 14
cctcgccatt cctcgggt                                                 18

<210> SEQ ID NO 15
<211> LENGTH: 18
<212> TYPE: DNA
<213> ORGANISM: Artificial Sequence
<220> FEATURE:
<223> OTHER INFORMATION: antisense sequence

<400> SEQUENCE: 15
gatcctcgcc attcctcg                                                 18

<210> SEQ ID NO 16
<211> LENGTH: 18
<212> TYPE: DNA
<213> ORGANISM: Artificial Sequence
<220> FEATURE:
<223> OTHER INFORMATION: antisense sequence
```

```
<400> SEQUENCE: 16
agacggcttc ctgggctt                                                18

<210> SEQ ID NO 17
<211> LENGTH: 18
<212> TYPE: DNA
<213> ORGANISM: Artificial Sequence
<220> FEATURE:
<223> OTHER INFORMATION: antisense sequence

<400> SEQUENCE: 17
ttgaaggagc agccgaca                                                18

<210> SEQ ID NO 18
<211> LENGTH: 18
<212> TYPE: DNA
<213> ORGANISM: Artificial Sequence
<220> FEATURE:
<223> OTHER INFORMATION: antisense sequence

<400> SEQUENCE: 18
ggccttccac tgtttcat                                                18

<210> SEQ ID NO 19
<211> LENGTH: 18
<212> TYPE: DNA
<213> ORGANISM: Artificial Sequence
<220> FEATURE:
<223> OTHER INFORMATION: antisense sequence

<400> SEQUENCE: 19
ccacttccac ggctgcct                                                18

<210> SEQ ID NO 20
<211> LENGTH: 18
<212> TYPE: DNA
<213> ORGANISM: Artificial Sequence
<220> FEATURE:
<223> OTHER INFORMATION: antisense sequence

<400> SEQUENCE: 20
cgcctggtga cattggtg                                                18

<210> SEQ ID NO 21
<211> LENGTH: 18
<212> TYPE: DNA
<213> ORGANISM: Artificial Sequence
<220> FEATURE:
<223> OTHER INFORMATION: antisense sequence

<400> SEQUENCE: 21
cgcatcatac tcccctct                                                18

<210> SEQ ID NO 22
<211> LENGTH: 18
<212> TYPE: DNA
<213> ORGANISM: Artificial Sequence
<220> FEATURE:
<223> OTHER INFORMATION: antisense sequence

<400> SEQUENCE: 22
aggcgtcaat ggcgtgct                                                18

<210> SEQ ID NO 23
```

```
<211> LENGTH: 18
<212> TYPE: DNA
<213> ORGANISM: Artificial Sequence
<220> FEATURE:
<223> OTHER INFORMATION: antisense sequence

<400> SEQUENCE: 23
ggaaggcgtc aatggcgt                                                 18

<210> SEQ ID NO 24
<211> LENGTH: 18
<212> TYPE: DNA
<213> ORGANISM: Artificial Sequence
<220> FEATURE:
<223> OTHER INFORMATION: antisense sequence

<400> SEQUENCE: 24
ggaagaagag tgggcatc                                                 18

<210> SEQ ID NO 25
<211> LENGTH: 18
<212> TYPE: DNA
<213> ORGANISM: Artificial Sequence
<220> FEATURE:
<223> OTHER INFORMATION: antisense sequence

<400> SEQUENCE: 25
cgtaggcgtg cttgggtg                                                 18

<210> SEQ ID NO 26
<211> LENGTH: 18
<212> TYPE: DNA
<213> ORGANISM: Artificial Sequence
<220> FEATURE:
<223> OTHER INFORMATION: antisense sequence

<400> SEQUENCE: 26
gccccgccca ccctaagt                                                 18

<210> SEQ ID NO 27
<211> LENGTH: 18
<212> TYPE: DNA
<213> ORGANISM: Artificial Sequence
<220> FEATURE:
<223> OTHER INFORMATION: antisense sequence

<400> SEQUENCE: 27
ggagccccgc ccaccctca                                                18

<210> SEQ ID NO 28
<211> LENGTH: 18
<212> TYPE: DNA
<213> ORGANISM: Artificial Sequence
<220> FEATURE:
<223> OTHER INFORMATION: antisense sequence

<400> SEQUENCE: 28
ctcaggagcc ccgcccac                                                 18

<210> SEQ ID NO 29
<211> LENGTH: 18
<212> TYPE: DNA
<213> ORGANISM: Artificial Sequence
<220> FEATURE:
<223> OTHER INFORMATION: antisense sequence

<400> SEQUENCE: 29
```

-continued aagggcaggg catcacag                                        18

<210> SEQ ID NO 30
<211> LENGTH: 18
<212> TYPE: DNA
<213> ORGANISM: Artificial Sequence
<220> FEATURE:
<223> OTHER INFORMATION: antisense sequence

<400> SEQUENCE: 30
tttgtgccct gaggtctt                                        18

<210> SEQ ID NO 31
<211> LENGTH: 18
<212> TYPE: DNA
<213> ORGANISM: Artificial Sequence
<220> FEATURE:
<223> OTHER INFORMATION: antisense sequence

<400> SEQUENCE: 31
cacccatctt tgtgccct                                        18

<210> SEQ ID NO 32
<211> LENGTH: 18
<212> TYPE: DNA
<213> ORGANISM: Artificial Sequence
<220> FEATURE:
<223> OTHER INFORMATION: antisense sequence

<400> SEQUENCE: 32
ggcctcccag tgtcgcat                                        18

<210> SEQ ID NO 33
<211> LENGTH: 18
<212> TYPE: DNA
<213> ORGANISM: Artificial Sequence
<220> FEATURE:
<223> OTHER INFORMATION: antisense sequence

<400> SEQUENCE: 33
cccggtcctg tttctgac                                        18

<210> SEQ ID NO 34
<211> LENGTH: 18
<212> TYPE: DNA
<213> ORGANISM: Artificial Sequence
<220> FEATURE:
<223> OTHER INFORMATION: antisense sequence

<400> SEQUENCE: 34
gcaccccatc ccttccac                                        18

<210> SEQ ID NO 35
<211> LENGTH: 18
<212> TYPE: DNA
<213> ORGANISM: Artificial Sequence
<220> FEATURE:
<223> OTHER INFORMATION: antisense sequence

<400> SEQUENCE: 35
tggagccgtc tgggtttg                                        18

<210> SEQ ID NO 36
<211> LENGTH: 18
<212> TYPE: DNA

```
<213> ORGANISM: Artificial Sequence
<220> FEATURE:
<223> OTHER INFORMATION: antisense sequence

<400> SEQUENCE: 36
gtcttcaaat ccaacccc                                                 18

<210> SEQ ID NO 37
<211> LENGTH: 18
<212> TYPE: DNA
<213> ORGANISM: Artificial Sequence
<220> FEATURE:
<223> OTHER INFORMATION: antisense sequence

<400> SEQUENCE: 37
ttctgggctg gaaggaaa                                                 18

<210> SEQ ID NO 38
<211> LENGTH: 18
<212> TYPE: DNA
<213> ORGANISM: Artificial Sequence
<220> FEATURE:
<223> OTHER INFORMATION: antisense sequence

<400> SEQUENCE: 38
actttctggg ctggaagg                                                 18

<210> SEQ ID NO 39
<211> LENGTH: 18
<212> TYPE: DNA
<213> ORGANISM: Artificial Sequence
<220> FEATURE:
<223> OTHER INFORMATION: antisense sequence

<400> SEQUENCE: 39
agagactttc tgggctgg                                                 18

<210> SEQ ID NO 40
<211> LENGTH: 18
<212> TYPE: DNA
<213> ORGANISM: Artificial Sequence
<220> FEATURE:
<223> OTHER INFORMATION: antisense sequence

<400> SEQUENCE: 40
tttccagaac ccctgtag                                                 18

<210> SEQ ID NO 41
<211> LENGTH: 18
<212> TYPE: DNA
<213> ORGANISM: Artificial Sequence
<220> FEATURE:
<223> OTHER INFORMATION: antisense sequence

<400> SEQUENCE: 41
atgtttccag aacccctg                                                 18

<210> SEQ ID NO 42
<211> LENGTH: 18
<212> TYPE: DNA
<213> ORGANISM: Artificial Sequence
<220> FEATURE:
<223> OTHER INFORMATION: antisense sequence

<400> SEQUENCE: 42
gggctgggtg tgctcctg                                                 18
```

<210> SEQ ID NO 43
<211> LENGTH: 18
<212> TYPE: DNA
<213> ORGANISM: Artificial Sequence
<220> FEATURE:
<223> OTHER INFORMATION: antisense sequence

<400> SEQUENCE: 43
tttatgcccc tcttcttc                                                 18

<210> SEQ ID NO 44
<211> LENGTH: 18
<212> TYPE: DNA
<213> ORGANISM: Artificial Sequence
<220> FEATURE:
<223> OTHER INFORMATION: antisense sequence

<400> SEQUENCE: 44
ggaaagttta tgcccctc                                                 18

<210> SEQ ID NO 45
<211> LENGTH: 18
<212> TYPE: DNA
<213> ORGANISM: Artificial Sequence
<220> FEATURE:
<223> OTHER INFORMATION: antisense sequence

<400> SEQUENCE: 45
tacgggattc tggaaagc                                                 18

<210> SEQ ID NO 46
<211> LENGTH: 18
<212> TYPE: DNA
<213> ORGANISM: Artificial Sequence
<220> FEATURE:
<223> OTHER INFORMATION: antisense sequence

<400> SEQUENCE: 46
aggtgttacg ggattctg                                                 18

<210> SEQ ID NO 47
<211> LENGTH: 20
<212> TYPE: DNA
<213> ORGANISM: Artificial Sequence
<220> FEATURE:
<223> OTHER INFORMATION: antisense sequence

<400> SEQUENCE: 47
gtcgcagcgc gccggaattc                                               20

<210> SEQ ID NO 48
<211> LENGTH: 20
<212> TYPE: DNA
<213> ORGANISM: Artificial Sequence
<220> FEATURE:
<223> OTHER INFORMATION: antisense sequence

<400> SEQUENCE: 48
ccaacggtcg cagcgcgccg                                               20

<210> SEQ ID NO 49
<211> LENGTH: 20
<212> TYPE: DNA
<213> ORGANISM: Artificial Sequence
<220> FEATURE:

-continued

<223> OTHER INFORMATION: antisense sequence

<400> SEQUENCE: 49
cagccatgag agctgtgacc                                        20

<210> SEQ ID NO 50
<211> LENGTH: 20
<212> TYPE: DNA
<213> ORGANISM: Artificial Sequence
<220> FEATURE:
<223> OTHER INFORMATION: antisense sequence

<400> SEQUENCE: 50
acgctagctg cagccatgag                                        20

<210> SEQ ID NO 51
<211> LENGTH: 20
<212> TYPE: DNA
<213> ORGANISM: Artificial Sequence
<220> FEATURE:
<223> OTHER INFORMATION: antisense sequence

<400> SEQUENCE: 51
gccacactgc gcctggaagg                                        20

<210> SEQ ID NO 52
<211> LENGTH: 20
<212> TYPE: DNA
<213> ORGANISM: Artificial Sequence
<220> FEATURE:
<223> OTHER INFORMATION: antisense sequence

<400> SEQUENCE: 52
ccggcaggct ctccacctcc                                        20

<210> SEQ ID NO 53
<211> LENGTH: 20
<212> TYPE: DNA
<213> ORGANISM: Artificial Sequence
<220> FEATURE:
<223> OTHER INFORMATION: antisense sequence

<400> SEQUENCE: 53
gcagcggcct tcgtggcagc                                        20

<210> SEQ ID NO 54
<211> LENGTH: 20
<212> TYPE: DNA
<213> ORGANISM: Artificial Sequence
<220> FEATURE:
<223> OTHER INFORMATION: antisense sequence

<400> SEQUENCE: 54
cctcgtggtg cgccttcacg                                        20

<210> SEQ ID NO 55
<211> LENGTH: 20
<212> TYPE: DNA
<213> ORGANISM: Artificial Sequence
<220> FEATURE:
<223> OTHER INFORMATION: antisense sequence

<400> SEQUENCE: 55
ctcgacactt gccacaagtc                                        20

```
<210> SEQ ID NO 56
<211> LENGTH: 20
<212> TYPE: DNA
<213> ORGANISM: Artificial Sequence
<220> FEATURE:
<223> OTHER INFORMATION: antisense sequence

<400> SEQUENCE: 56
cactgcacct cgtgctcctg                                              20

<210> SEQ ID NO 57
<211> LENGTH: 20
<212> TYPE: DNA
<213> ORGANISM: Artificial Sequence
<220> FEATURE:
<223> OTHER INFORMATION: antisense sequence

<400> SEQUENCE: 57
cctctgcagg agctctgacc                                              20

<210> SEQ ID NO 58
<211> LENGTH: 20
<212> TYPE: DNA
<213> ORGANISM: Artificial Sequence
<220> FEATURE:
<223> OTHER INFORMATION: antisense sequence

<400> SEQUENCE: 58
cagccggtgc tgccggctgc                                              20

<210> SEQ ID NO 59
<211> LENGTH: 20
<212> TYPE: DNA
<213> ORGANISM: Artificial Sequence
<220> FEATURE:
<223> OTHER INFORMATION: antisense sequence

<400> SEQUENCE: 59
ccggtgccgt cgccgttcag                                              20

<210> SEQ ID NO 60
<211> LENGTH: 20
<212> TYPE: DNA
<213> ORGANISM: Artificial Sequence
<220> FEATURE:
<223> OTHER INFORMATION: antisense sequence

<400> SEQUENCE: 60
acgtcgggcc tgaaggcgtc                                              20

<210> SEQ ID NO 61
<211> LENGTH: 20
<212> TYPE: DNA
<213> ORGANISM: Artificial Sequence
<220> FEATURE:
<223> OTHER INFORMATION: antisense sequence

<400> SEQUENCE: 61
ctgtcaggtc cacaatggcc                                              20

<210> SEQ ID NO 62
<211> LENGTH: 20
<212> TYPE: DNA
<213> ORGANISM: Artificial Sequence
<220> FEATURE:
<223> OTHER INFORMATION: antisense sequence
```

<400> SEQUENCE: 62
gccggctgtg cctggctgcc                                               20

<210> SEQ ID NO 63
<211> LENGTH: 20
<212> TYPE: DNA
<213> ORGANISM: Artificial Sequence
<220> FEATURE:
<223> OTHER INFORMATION: antisense sequence

<400> SEQUENCE: 63
cttggctgca ggccgacacc                                               20

<210> SEQ ID NO 64
<211> LENGTH: 20
<212> TYPE: DNA
<213> ORGANISM: Artificial Sequence
<220> FEATURE:
<223> OTHER INFORMATION: antisense sequence

<400> SEQUENCE: 64
cggccaatgc caccacagcc                                               20

<210> SEQ ID NO 65
<211> LENGTH: 20
<212> TYPE: DNA
<213> ORGANISM: Artificial Sequence
<220> FEATURE:
<223> OTHER INFORMATION: antisense sequence

<400> SEQUENCE: 65
actgtgctcc tgctacatgg                                               20

<210> SEQ ID NO 66
<211> LENGTH: 20
<212> TYPE: DNA
<213> ORGANISM: Artificial Sequence
<220> FEATURE:
<223> OTHER INFORMATION: antisense sequence

<400> SEQUENCE: 66
gctctggcca gcaggaggcc                                               20

<210> SEQ ID NO 67
<211> LENGTH: 20
<212> TYPE: DNA
<213> ORGANISM: Artificial Sequence
<220> FEATURE:
<223> OTHER INFORMATION: antisense sequence

<400> SEQUENCE: 67
ccacagccag cctggccaag                                               20

<210> SEQ ID NO 68
<211> LENGTH: 20
<212> TYPE: DNA
<213> ORGANISM: Artificial Sequence
<220> FEATURE:
<223> OTHER INFORMATION: antisense sequence

<400> SEQUENCE: 68
ctctgtcttc gtgagctgga                                               20

<210> SEQ ID NO 69
<211> LENGTH: 20

```
<212> TYPE: DNA
<213> ORGANISM: Artificial Sequence
<220> FEATURE:
<223> OTHER INFORMATION: control sequence

<400> SEQUENCE: 69
cctcgtgctg cggcttcacg                                            20

<210> SEQ ID NO 70
<211> LENGTH: 20
<212> TYPE: DNA
<213> ORGANISM: Artificial Sequence
<220> FEATURE:
<223> OTHER INFORMATION: control sequence

<400> SEQUENCE: 70
cctggtgctc cggcttcacg                                            20

<210> SEQ ID NO 71
<211> LENGTH: 18
<212> TYPE: DNA
<213> ORGANISM: Artificial Sequence
<220> FEATURE:
<223> OTHER INFORMATION: antisense sequence

<400> SEQUENCE: 71
agagccgacg accgccgc                                              18

<210> SEQ ID NO 72
<211> LENGTH: 18
<212> TYPE: DNA
<213> ORGANISM: Artificial Sequence
<220> FEATURE:
<223> OTHER INFORMATION: antisense sequence

<400> SEQUENCE: 72
ggaagagccg acgaccgc                                              18

<210> SEQ ID NO 73
<211> LENGTH: 18
<212> TYPE: DNA
<213> ORGANISM: Artificial Sequence
<220> FEATURE:
<223> OTHER INFORMATION: antisense sequence

<400> SEQUENCE: 73
cgcgccagga gagtccat                                              18

<210> SEQ ID NO 74
<211> LENGTH: 18
<212> TYPE: DNA
<213> ORGANISM: Artificial Sequence
<220> FEATURE:
<223> OTHER INFORMATION: antisense sequence

<400> SEQUENCE: 74
ttagcggcgg gttagtct                                              18

<210> SEQ ID NO 75
<211> LENGTH: 18
<212> TYPE: DNA
<213> ORGANISM: Artificial Sequence
<220> FEATURE:
<223> OTHER INFORMATION: antisense sequence

<400> SEQUENCE: 75
```
agctttagcg gcgggtta                                                        18

<210> SEQ ID NO 76
<211> LENGTH: 18
<212> TYPE: DNA
<213> ORGANISM: Artificial Sequence
<220> FEATURE:
<223> OTHER INFORMATION: antisense sequence

<400> SEQUENCE: 76
ctcggtctgc ttcgggct                                                        18

<210> SEQ ID NO 77
<211> LENGTH: 18
<212> TYPE: DNA
<213> ORGANISM: Artificial Sequence
<220> FEATURE:
<223> OTHER INFORMATION: antisense sequence

<400> SEQUENCE: 77
tgcccacact cggtctgc                                                        18

<210> SEQ ID NO 78
<211> LENGTH: 18
<212> TYPE: DNA
<213> ORGANISM: Artificial Sequence
<220> FEATURE:
<223> OTHER INFORMATION: antisense sequence

<400> SEQUENCE: 78
cggtgcccac actcggtc                                                        18

<210> SEQ ID NO 79
<211> LENGTH: 18
<212> TYPE: DNA
<213> ORGANISM: Artificial Sequence
<220> FEATURE:
<223> OTHER INFORMATION: antisense sequence

<400> SEQUENCE: 79
gaagcggtgc ccacactc                                                        18

<210> SEQ ID NO 80
<211> LENGTH: 18
<212> TYPE: DNA
<213> ORGANISM: Artificial Sequence
<220> FEATURE:
<223> OTHER INFORMATION: antisense sequence

<400> SEQUENCE: 80
ttacacgcct tctccacg                                                        18

<210> SEQ ID NO 81
<211> LENGTH: 18
<212> TYPE: DNA
<213> ORGANISM: Artificial Sequence
<220> FEATURE:
<223> OTHER INFORMATION: antisense sequence

<400> SEQUENCE: 81
gtatttacac gccttctc                                                        18

<210> SEQ ID NO 82
<211> LENGTH: 18
<212> TYPE: DNA
<213> ORGANISM: Artificial Sequence

```
<220> FEATURE:
<223> OTHER INFORMATION: antisense sequence

<400> SEQUENCE: 82
ccggtattta cacgcctt                                                   18

<210> SEQ ID NO 83
<211> LENGTH: 18
<212> TYPE: DNA
<213> ORGANISM: Artificial Sequence
<220> FEATURE:
<223> OTHER INFORMATION: antisense sequence

<400> SEQUENCE: 83
gagggcagga caccacca                                                   18

<210> SEQ ID NO 84
<211> LENGTH: 18
<212> TYPE: DNA
<213> ORGANISM: Artificial Sequence
<220> FEATURE:
<223> OTHER INFORMATION: antisense sequence

<400> SEQUENCE: 84
tgtgagggca ggacacca                                                   18

<210> SEQ ID NO 85
<211> LENGTH: 18
<212> TYPE: DNA
<213> ORGANISM: Artificial Sequence
<220> FEATURE:
<223> OTHER INFORMATION: antisense sequence

<400> SEQUENCE: 85
cacttgtgag ggcaggac                                                   18

<210> SEQ ID NO 86
<211> LENGTH: 18
<212> TYPE: DNA
<213> ORGANISM: Artificial Sequence
<220> FEATURE:
<223> OTHER INFORMATION: antisense sequence

<400> SEQUENCE: 86
gctggtttgt cccctgaa                                                   18

<210> SEQ ID NO 87
<211> LENGTH: 18
<212> TYPE: DNA
<213> ORGANISM: Artificial Sequence
<220> FEATURE:
<223> OTHER INFORMATION: antisense sequence

<400> SEQUENCE: 87
atctgctggt ttgtcccc                                                   18

<210> SEQ ID NO 88
<211> LENGTH: 18
<212> TYPE: DNA
<213> ORGANISM: Artificial Sequence
<220> FEATURE:
<223> OTHER INFORMATION: antisense sequence

<400> SEQUENCE: 88
cgcggttctg gagggact                                                   18
```

```
<210> SEQ ID NO 89
<211> LENGTH: 18
<212> TYPE: DNA
<213> ORGANISM: Artificial Sequence
<220> FEATURE:
<223> OTHER INFORMATION: antisense sequence

<400> SEQUENCE: 89
ccccgcactc ttgtccac                                          18

<210> SEQ ID NO 90
<211> LENGTH: 18
<212> TYPE: DNA
<213> ORGANISM: Artificial Sequence
<220> FEATURE:
<223> OTHER INFORMATION: antisense sequence

<400> SEQUENCE: 90
ttgccccgca ctcttgtc                                          18

<210> SEQ ID NO 91
<211> LENGTH: 18
<212> TYPE: DNA
<213> ORGANISM: Artificial Sequence
<220> FEATURE:
<223> OTHER INFORMATION: antisense sequence

<400> SEQUENCE: 91
ccacttgccc cgcactct                                          18

<210> SEQ ID NO 92
<211> LENGTH: 18
<212> TYPE: DNA
<213> ORGANISM: Artificial Sequence
<220> FEATURE:
<223> OTHER INFORMATION: antisense sequence

<400> SEQUENCE: 92
gagccacttg ccccgcac                                          18

<210> SEQ ID NO 93
<211> LENGTH: 18
<212> TYPE: DNA
<213> ORGANISM: Artificial Sequence
<220> FEATURE:
<223> OTHER INFORMATION: antisense sequence

<400> SEQUENCE: 93
ttccgagcca cttgcccc                                          18

<210> SEQ ID NO 94
<211> LENGTH: 18
<212> TYPE: DNA
<213> ORGANISM: Artificial Sequence
<220> FEATURE:
<223> OTHER INFORMATION: antisense sequence

<400> SEQUENCE: 94
tccgccgctt gtagtcgc                                          18

<210> SEQ ID NO 95
<211> LENGTH: 18
<212> TYPE: DNA
<213> ORGANISM: Artificial Sequence
<220> FEATURE:
<223> OTHER INFORMATION: antisense sequence
```

<400> SEQUENCE: 95
tgcttccgcc gcttgtag                                               18

<210> SEQ ID NO 96
<211> LENGTH: 18
<212> TYPE: DNA
<213> ORGANISM: Artificial Sequence
<220> FEATURE:
<223> OTHER INFORMATION: antisense sequence

<400> SEQUENCE: 96
tcctgcttcc gccgcttg                                               18

<210> SEQ ID NO 97
<211> LENGTH: 18
<212> TYPE: DNA
<213> ORGANISM: Artificial Sequence
<220> FEATURE:
<223> OTHER INFORMATION: antisense sequence

<400> SEQUENCE: 97
gtccccgttc aggtagac                                               18

<210> SEQ ID NO 98
<211> LENGTH: 18
<212> TYPE: DNA
<213> ORGANISM: Artificial Sequence
<220> FEATURE:
<223> OTHER INFORMATION: antisense sequence

<400> SEQUENCE: 98
tcccgtcccc gttcaggt                                               18

<210> SEQ ID NO 99
<211> LENGTH: 18
<212> TYPE: DNA
<213> ORGANISM: Artificial Sequence
<220> FEATURE:
<223> OTHER INFORMATION: antisense sequence

<400> SEQUENCE: 99
ccatcccgtc cccgttca                                               18

<210> SEQ ID NO 100
<211> LENGTH: 18
<212> TYPE: DNA
<213> ORGANISM: Artificial Sequence
<220> FEATURE:
<223> OTHER INFORMATION: antisense sequence

<400> SEQUENCE: 100
tccccatccc gtccccgt                                               18

<210> SEQ ID NO 101
<211> LENGTH: 18
<212> TYPE: DNA
<213> ORGANISM: Artificial Sequence
<220> FEATURE:
<223> OTHER INFORMATION: antisense sequence

<400> SEQUENCE: 101
cccttcccca tcccgtcc                                               18

<210> SEQ ID NO 102

<211> LENGTH: 18
<212> TYPE: DNA
<213> ORGANISM: Artificial Sequence
<220> FEATURE:
<223> OTHER INFORMATION: antisense sequence

<400> SEQUENCE: 102
tgcgtcccct tccccatc                                                   18

<210> SEQ ID NO 103
<211> LENGTH: 18
<212> TYPE: DNA
<213> ORGANISM: Artificial Sequence
<220> FEATURE:
<223> OTHER INFORMATION: antisense sequence

<400> SEQUENCE: 103
aagtgcgtcc ccttcccc                                                   18

<210> SEQ ID NO 104
<211> LENGTH: 18
<212> TYPE: DNA
<213> ORGANISM: Artificial Sequence
<220> FEATURE:
<223> OTHER INFORMATION: antisense sequence

<400> SEQUENCE: 104
cgacaagtgc gtcccctt                                                   18

<210> SEQ ID NO 105
<211> LENGTH: 18
<212> TYPE: DNA
<213> ORGANISM: Artificial Sequence
<220> FEATURE:
<223> OTHER INFORMATION: antisense sequence

<400> SEQUENCE: 105
aaggaagcag ggcatcat                                                   18

<210> SEQ ID NO 106
<211> LENGTH: 18
<212> TYPE: DNA
<213> ORGANISM: Artificial Sequence
<220> FEATURE:
<223> OTHER INFORMATION: antisense sequence

<400> SEQUENCE: 106
ctctccagtg ggcttctt                                                   18

<210> SEQ ID NO 107
<211> LENGTH: 18
<212> TYPE: DNA
<213> ORGANISM: Artificial Sequence
<220> FEATURE:
<223> OTHER INFORMATION: antisense sequence

<400> SEQUENCE: 107
tcatctctcc agtgggct                                                   18

<210> SEQ ID NO 108
<211> LENGTH: 18
<212> TYPE: DNA
<213> ORGANISM: Artificial Sequence
<220> FEATURE:
<223> OTHER INFORMATION: antisense sequence

<400> SEQUENCE: 108

```
gctaaatcca cctcccca                                                 18

<210> SEQ ID NO 109
<211> LENGTH: 18
<212> TYPE: DNA
<213> ORGANISM: Artificial Sequence
<220> FEATURE:
<223> OTHER INFORMATION: antisense sequence

<400> SEQUENCE: 109
tctgccgctt cctccgtc                                                 18

<210> SEQ ID NO 110
<211> LENGTH: 18
<212> TYPE: DNA
<213> ORGANISM: Artificial Sequence
<220> FEATURE:
<223> OTHER INFORMATION: antisense sequence

<400> SEQUENCE: 110
ccgccttctg ccgcttcc                                                 18

<210> SEQ ID NO 111
<211> LENGTH: 18
<212> TYPE: DNA
<213> ORGANISM: Artificial Sequence
<220> FEATURE:
<223> OTHER INFORMATION: antisense sequence

<400> SEQUENCE: 111
gcatggcggg cgagcggc                                                 18

<210> SEQ ID NO 112
<211> LENGTH: 18
<212> TYPE: DNA
<213> ORGANISM: Artificial Sequence
<220> FEATURE:
<223> OTHER INFORMATION: antisense sequence

<400> SEQUENCE: 112
ccgtcgcttg ggcttctc                                                 18

<210> SEQ ID NO 113
<211> LENGTH: 18
<212> TYPE: DNA
<213> ORGANISM: Artificial Sequence
<220> FEATURE:
<223> OTHER INFORMATION: antisense sequence

<400> SEQUENCE: 113
gggcacttga agactcct                                                 18

<210> SEQ ID NO 114
<211> LENGTH: 18
<212> TYPE: DNA
<213> ORGANISM: Artificial Sequence
<220> FEATURE:
<223> OTHER INFORMATION: antisense sequence

<400> SEQUENCE: 114
ctcagggcac ttgaagac                                                 18

<210> SEQ ID NO 115
<211> LENGTH: 18
<212> TYPE: DNA
```

```
<213> ORGANISM: Artificial Sequence
<220> FEATURE:
<223> OTHER INFORMATION: antisense sequence

<400> SEQUENCE: 115
tggtcctcag ggcacttg                                                18

<210> SEQ ID NO 116
<211> LENGTH: 18
<212> TYPE: DNA
<213> ORGANISM: Artificial Sequence
<220> FEATURE:
<223> OTHER INFORMATION: antisense sequence

<400> SEQUENCE: 116
aagctggtcc tcagggca                                                18

<210> SEQ ID NO 117
<211> LENGTH: 18
<212> TYPE: DNA
<213> ORGANISM: Artificial Sequence
<220> FEATURE:
<223> OTHER INFORMATION: antisense sequence

<400> SEQUENCE: 117
gcggcagccc tcctcact                                                18

<210> SEQ ID NO 118
<211> LENGTH: 18
<212> TYPE: DNA
<213> ORGANISM: Artificial Sequence
<220> FEATURE:
<223> OTHER INFORMATION: antisense sequence

<400> SEQUENCE: 118
ctccagcggc agccctcc                                                18

<210> SEQ ID NO 119
<211> LENGTH: 18
<212> TYPE: DNA
<213> ORGANISM: Artificial Sequence
<220> FEATURE:
<223> OTHER INFORMATION: antisense sequence

<400> SEQUENCE: 119
tagggcaggg aatgacat                                                18

<210> SEQ ID NO 120
<211> LENGTH: 18
<212> TYPE: DNA
<213> ORGANISM: Artificial Sequence
<220> FEATURE:
<223> OTHER INFORMATION: antisense sequence

<400> SEQUENCE: 120
cgattagggc agggaatg                                                18

<210> SEQ ID NO 121
<211> LENGTH: 18
<212> TYPE: DNA
<213> ORGANISM: Artificial Sequence
<220> FEATURE:
<223> OTHER INFORMATION: antisense sequence

<400> SEQUENCE: 121
gggcagcgat tagggcag                                                18
```

<210> SEQ ID NO 122
<211> LENGTH: 18
<212> TYPE: DNA
<213> ORGANISM: Artificial Sequence
<220> FEATURE:
<223> OTHER INFORMATION: antisense sequence

<400> SEQUENCE: 122
gcctccccac tgaagtca                                                   18

<210> SEQ ID NO 123
<211> LENGTH: 18
<212> TYPE: DNA
<213> ORGANISM: Artificial Sequence
<220> FEATURE:
<223> OTHER INFORMATION: antisense sequence

<400> SEQUENCE: 123
atgcgggcac cacactta                                                   18

<210> SEQ ID NO 124
<211> LENGTH: 18
<212> TYPE: DNA
<213> ORGANISM: Artificial Sequence
<220> FEATURE:
<223> OTHER INFORMATION: antisense sequence

<400> SEQUENCE: 124
gggcaggcaa caggcagc                                                   18

<210> SEQ ID NO 125
<211> LENGTH: 18
<212> TYPE: DNA
<213> ORGANISM: Artificial Sequence
<220> FEATURE:
<223> OTHER INFORMATION: antisense sequence

<400> SEQUENCE: 125
ccacagtgcc cacaccac                                                   18

<210> SEQ ID NO 126
<211> LENGTH: 18
<212> TYPE: DNA
<213> ORGANISM: Artificial Sequence
<220> FEATURE:
<223> OTHER INFORMATION: antisense sequence

<400> SEQUENCE: 126
cgagccacag tgcccaca                                                   18

<210> SEQ ID NO 127
<211> LENGTH: 18
<212> TYPE: DNA
<213> ORGANISM: Artificial Sequence
<220> FEATURE:
<223> OTHER INFORMATION: antisense sequence

<400> SEQUENCE: 127
tcctcccgag ccacagtg                                                   18

<210> SEQ ID NO 128
<211> LENGTH: 18
<212> TYPE: DNA
<213> ORGANISM: Artificial Sequence
<220> FEATURE:

```
<223> OTHER INFORMATION: antisense sequence

<400> SEQUENCE: 128
caggtcctcc cgagccac                                           18

<210> SEQ ID NO 129
<211> LENGTH: 18
<212> TYPE: DNA
<213> ORGANISM: Artificial Sequence
<220> FEATURE:
<223> OTHER INFORMATION: antisense sequence

<400> SEQUENCE: 129
ggcagagcac cagggcgg                                           18

<210> SEQ ID NO 130
<211> LENGTH: 18
<212> TYPE: DNA
<213> ORGANISM: Artificial Sequence
<220> FEATURE:
<223> OTHER INFORMATION: antisense sequence

<400> SEQUENCE: 130
ctttgaatgg gcagagca                                           18

<210> SEQ ID NO 131
<211> LENGTH: 18
<212> TYPE: DNA
<213> ORGANISM: Artificial Sequence
<220> FEATURE:
<223> OTHER INFORMATION: antisense sequence

<400> SEQUENCE: 131
ggagtctttg aatgggca                                           18

<210> SEQ ID NO 132
<211> LENGTH: 18
<212> TYPE: DNA
<213> ORGANISM: Artificial Sequence
<220> FEATURE:
<223> OTHER INFORMATION: antisense sequence

<400> SEQUENCE: 132
atgccgtgcc attgccag                                           18

<210> SEQ ID NO 133
<211> LENGTH: 18
<212> TYPE: DNA
<213> ORGANISM: Artificial Sequence
<220> FEATURE:
<223> OTHER INFORMATION: antisense sequence

<400> SEQUENCE: 133
ctcaccaggg cacacatc                                           18

<210> SEQ ID NO 134
<211> LENGTH: 18
<212> TYPE: DNA
<213> ORGANISM: Artificial Sequence
<220> FEATURE:
<223> OTHER INFORMATION: antisense sequence

<400> SEQUENCE: 134
cagctcctgc cgttgccg                                           18
```

```
<210> SEQ ID NO 135
<211> LENGTH: 18
<212> TYPE: DNA
<213> ORGANISM: Artificial Sequence
<220> FEATURE:
<223> OTHER INFORMATION: antisense sequence

<400> SEQUENCE: 135
atgagcacgc catcactg                                                 18

<210> SEQ ID NO 136
<211> LENGTH: 18
<212> TYPE: DNA
<213> ORGANISM: Artificial Sequence
<220> FEATURE:
<223> OTHER INFORMATION: antisense sequence

<400> SEQUENCE: 136
tgtagccgcc gtccatag                                                 18

<210> SEQ ID NO 137
<211> LENGTH: 18
<212> TYPE: DNA
<213> ORGANISM: Artificial Sequence
<220> FEATURE:
<223> OTHER INFORMATION: antisense sequence

<400> SEQUENCE: 137
gcctcctgta gccgccgt                                                 18

<210> SEQ ID NO 138
<211> LENGTH: 18
<212> TYPE: DNA
<213> ORGANISM: Artificial Sequence
<220> FEATURE:
<223> OTHER INFORMATION: antisense sequence

<400> SEQUENCE: 138
tagaaggctg ggctgaag                                                 18

<210> SEQ ID NO 139
<211> LENGTH: 18
<212> TYPE: DNA
<213> ORGANISM: Artificial Sequence
<220> FEATURE:
<223> OTHER INFORMATION: antisense sequence

<400> SEQUENCE: 139
gtgtgtagaa ggctgggc                                                 18

<210> SEQ ID NO 140
<211> LENGTH: 18
<212> TYPE: DNA
<213> ORGANISM: Artificial Sequence
<220> FEATURE:
<223> OTHER INFORMATION: antisense sequence

<400> SEQUENCE: 140
gtgtgccctc accactgc                                                 18

<210> SEQ ID NO 141
<211> LENGTH: 18
<212> TYPE: DNA
<213> ORGANISM: Artificial Sequence
<220> FEATURE:
<223> OTHER INFORMATION: antisense sequence
```

-continued

<400> SEQUENCE: 141
gacacggcgg gcaaaggg                                                        18

<210> SEQ ID NO 142
<211> LENGTH: 18
<212> TYPE: DNA
<213> ORGANISM: Artificial Sequence
<220> FEATURE:
<223> OTHER INFORMATION: antisense sequence

<400> SEQUENCE: 142
gaaggtgaca cggcgggc                                                        18

<210> SEQ ID NO 143
<211> LENGTH: 18
<212> TYPE: DNA
<213> ORGANISM: Artificial Sequence
<220> FEATURE:
<223> OTHER INFORMATION: antisense sequence

<400> SEQUENCE: 143
gcccagggtc gctctgat                                                        18

<210> SEQ ID NO 144
<211> LENGTH: 18
<212> TYPE: DNA
<213> ORGANISM: Artificial Sequence
<220> FEATURE:
<223> OTHER INFORMATION: antisense sequence

<400> SEQUENCE: 144
cttccagttt gggtcggg                                                        18

<210> SEQ ID NO 145
<211> LENGTH: 18
<212> TYPE: DNA
<213> ORGANISM: Artificial Sequence
<220> FEATURE:
<223> OTHER INFORMATION: antisense sequence

<400> SEQUENCE: 145
gataaccaaa gcccagag                                                        18

<210> SEQ ID NO 146
<211> LENGTH: 18
<212> TYPE: DNA
<213> ORGANISM: Artificial Sequence
<220> FEATURE:
<223> OTHER INFORMATION: antisense sequence

<400> SEQUENCE: 146
catcgtcctt tcccctcg                                                        18

<210> SEQ ID NO 147
<211> LENGTH: 18
<212> TYPE: DNA
<213> ORGANISM: Artificial Sequence
<220> FEATURE:
<223> OTHER INFORMATION: antisense sequence

<400> SEQUENCE: 147
ggccagggct gaagcacc                                                        18

<210> SEQ ID NO 148
<211> LENGTH: 18

```
<212> TYPE: DNA
<213> ORGANISM: Artificial Sequence
<220> FEATURE:
<223> OTHER INFORMATION: antisense sequence

<400> SEQUENCE: 148
ttgtttccag cccttcat                                                 18

<210> SEQ ID NO 149
<211> LENGTH: 18
<212> TYPE: DNA
<213> ORGANISM: Artificial Sequence
<220> FEATURE:
<223> OTHER INFORMATION: antisense sequence

<400> SEQUENCE: 149
catgtctgcc ctacccaa                                                 18

<210> SEQ ID NO 150
<211> LENGTH: 18
<212> TYPE: DNA
<213> ORGANISM: Artificial Sequence
<220> FEATURE:
<223> OTHER INFORMATION: antisense sequence

<400> SEQUENCE: 150
gctcccctgc tgtgccct                                                 18

<210> SEQ ID NO 151
<211> LENGTH: 18
<212> TYPE: DNA
<213> ORGANISM: Artificial Sequence
<220> FEATURE:
<223> OTHER INFORMATION: antisense sequence

<400> SEQUENCE: 151
tgaataagcc attgtggg                                                 18

<210> SEQ ID NO 152
<211> LENGTH: 18
<212> TYPE: DNA
<213> ORGANISM: Artificial Sequence
<220> FEATURE:
<223> OTHER INFORMATION: antisense sequence

<400> SEQUENCE: 152
ctttatgctc ttctgaat                                                 18

<210> SEQ ID NO 153
<211> LENGTH: 18
<212> TYPE: DNA
<213> ORGANISM: Artificial Sequence
<220> FEATURE:
<223> OTHER INFORMATION: antisense sequence

<400> SEQUENCE: 153
ggatgaaacc acagggca                                                 18

<210> SEQ ID NO 154
<211> LENGTH: 18
<212> TYPE: DNA
<213> ORGANISM: Artificial Sequence
<220> FEATURE:
<223> OTHER INFORMATION: antisense sequence

<400> SEQUENCE: 154
```
tcaaagtcca aggaaatg                                            18

<210> SEQ ID NO 155
<211> LENGTH: 18
<212> TYPE: DNA
<213> ORGANISM: Artificial Sequence
<220> FEATURE:
<223> OTHER INFORMATION: antisense sequence

<400> SEQUENCE: 155
tgaagcaccg agtggcag                                            18

<210> SEQ ID NO 156
<211> LENGTH: 18
<212> TYPE: DNA
<213> ORGANISM: Artificial Sequence
<220> FEATURE:
<223> OTHER INFORMATION: antisense sequence

<400> SEQUENCE: 156
gggcagattg gcactgtg                                            18

<210> SEQ ID NO 157
<211> LENGTH: 18
<212> TYPE: DNA
<213> ORGANISM: Artificial Sequence
<220> FEATURE:
<223> OTHER INFORMATION: antisense sequence

<400> SEQUENCE: 157
ctcctgagat ttgatgac                                            18

<210> SEQ ID NO 158
<211> LENGTH: 18
<212> TYPE: DNA
<213> ORGANISM: Artificial Sequence
<220> FEATURE:
<223> OTHER INFORMATION: antisense sequence

<400> SEQUENCE: 158
ctttccgtag gactggct                                            18

<210> SEQ ID NO 159
<211> LENGTH: 18
<212> TYPE: DNA
<213> ORGANISM: Artificial Sequence
<220> FEATURE:
<223> OTHER INFORMATION: antisense sequence

<400> SEQUENCE: 159
gattctgtag attgatga                                            18

<210> SEQ ID NO 160
<211> LENGTH: 18
<212> TYPE: DNA
<213> ORGANISM: Artificial Sequence
<220> FEATURE:
<223> OTHER INFORMATION: antisense sequence

<400> SEQUENCE: 160
ttcatctacc tcagtttt                                            18

<210> SEQ ID NO 161
<211> LENGTH: 18
<212> TYPE: DNA
<213> ORGANISM: Artificial Sequence

```
<220> FEATURE:
<223> OTHER INFORMATION: antisense sequence

<400> SEQUENCE: 161
tccgttacag cacagcca                                                18

<210> SEQ ID NO 162
<211> LENGTH: 18
<212> TYPE: DNA
<213> ORGANISM: Artificial Sequence
<220> FEATURE:
<223> OTHER INFORMATION: antisense sequence

<400> SEQUENCE: 162
gcatgtgctc ccgtaagg                                                18

<210> SEQ ID NO 163
<211> LENGTH: 18
<212> TYPE: DNA
<213> ORGANISM: Artificial Sequence
<220> FEATURE:
<223> OTHER INFORMATION: antisense sequence

<400> SEQUENCE: 163
cttttcaagt ttctttat                                                18

<210> SEQ ID NO 164
<211> LENGTH: 18
<212> TYPE: DNA
<213> ORGANISM: Artificial Sequence
<220> FEATURE:
<223> OTHER INFORMATION: antisense sequence

<400> SEQUENCE: 164
cttccatcaa aggtctca                                                18

<210> SEQ ID NO 165
<211> LENGTH: 18
<212> TYPE: DNA
<213> ORGANISM: Artificial Sequence
<220> FEATURE:
<223> OTHER INFORMATION: antisense sequence

<400> SEQUENCE: 165
tctaaaacgg ctaatctt                                                18

<210> SEQ ID NO 166
<211> LENGTH: 18
<212> TYPE: DNA
<213> ORGANISM: Artificial Sequence
<220> FEATURE:
<223> OTHER INFORMATION: antisense sequence

<400> SEQUENCE: 166
tcatcttgta atctgtca                                                18

<210> SEQ ID NO 167
<211> LENGTH: 18
<212> TYPE: DNA
<213> ORGANISM: Artificial Sequence
<220> FEATURE:
<223> OTHER INFORMATION: antisense sequence

<400> SEQUENCE: 167
ggactggctg aagatgga                                                18
```

<210> SEQ ID NO 168
<211> LENGTH: 18
<212> TYPE: DNA
<213> ORGANISM: Artificial Sequence
<220> FEATURE:
<223> OTHER INFORMATION: antisense sequence

<400> SEQUENCE: 168
ccctccctga cccatccc                    18

<210> SEQ ID NO 169
<211> LENGTH: 18
<212> TYPE: DNA
<213> ORGANISM: Artificial Sequence
<220> FEATURE:
<223> OTHER INFORMATION: antisense sequence

<400> SEQUENCE: 169
gaatgagcca caaagcgg                    18

<210> SEQ ID NO 170
<211> LENGTH: 18
<212> TYPE: DNA
<213> ORGANISM: Artificial Sequence
<220> FEATURE:
<223> OTHER INFORMATION: antisense sequence

<400> SEQUENCE: 170
caagaacaga gtgtcatc                    18

<210> SEQ ID NO 171
<211> LENGTH: 18
<212> TYPE: DNA
<213> ORGANISM: Artificial Sequence
<220> FEATURE:
<223> OTHER INFORMATION: antisense sequence

<400> SEQUENCE: 171
gtctaaatcc aggtcaat                    18

<210> SEQ ID NO 172
<211> LENGTH: 18
<212> TYPE: DNA
<213> ORGANISM: Artificial Sequence
<220> FEATURE:
<223> OTHER INFORMATION: antisense sequence

<400> SEQUENCE: 172
aaacttacca tctttcaa                    18

<210> SEQ ID NO 173
<211> LENGTH: 18
<212> TYPE: DNA
<213> ORGANISM: Artificial Sequence
<220> FEATURE:
<223> OTHER INFORMATION: antisense sequence

<400> SEQUENCE: 173
ctctgtgtcc tccataac                    18

<210> SEQ ID NO 174
<211> LENGTH: 18
<212> TYPE: DNA
<213> ORGANISM: Artificial Sequence
<220> FEATURE:
<223> OTHER INFORMATION: antisense sequence

<400> SEQUENCE: 174
cttaactgga acagccta                                              18

<210> SEQ ID NO 175
<211> LENGTH: 18
<212> TYPE: DNA
<213> ORGANISM: Artificial Sequence
<220> FEATURE:
<223> OTHER INFORMATION: antisense sequence

<400> SEQUENCE: 175
gcaggaagaa tgaaaatg                                              18

<210> SEQ ID NO 176
<211> LENGTH: 18
<212> TYPE: DNA
<213> ORGANISM: Artificial Sequence
<220> FEATURE:
<223> OTHER INFORMATION: antisense sequence

<400> SEQUENCE: 176
tatttggttg aatcttat                                              18

<210> SEQ ID NO 177
<211> LENGTH: 18
<212> TYPE: DNA
<213> ORGANISM: Artificial Sequence
<220> FEATURE:
<223> OTHER INFORMATION: antisense sequence

<400> SEQUENCE: 177
aaattctatc catcctca                                              18

<210> SEQ ID NO 178
<211> LENGTH: 18
<212> TYPE: DNA
<213> ORGANISM: Artificial Sequence
<220> FEATURE:
<223> OTHER INFORMATION: antisense sequence

<400> SEQUENCE: 178
aaattgtaaa ggttttct                                              18

<210> SEQ ID NO 179
<211> LENGTH: 18
<212> TYPE: DNA
<213> ORGANISM: Artificial Sequence
<220> FEATURE:
<223> OTHER INFORMATION: antisense sequence

<400> SEQUENCE: 179
acaatgaaac tctgtctc                                              18

<210> SEQ ID NO 180
<211> LENGTH: 18
<212> TYPE: DNA
<213> ORGANISM: Artificial Sequence
<220> FEATURE:
<223> OTHER INFORMATION: antisense sequence

<400> SEQUENCE: 180
gcaaaactcc gtctctac                                              18

<210> SEQ ID NO 181

<211> LENGTH: 18
<212> TYPE: DNA
<213> ORGANISM: Artificial Sequence
<220> FEATURE:
<223> OTHER INFORMATION: antisense sequence

<400> SEQUENCE: 181
caatagttgt cagaggct                                                    18

<210> SEQ ID NO 182
<211> LENGTH: 18
<212> TYPE: DNA
<213> ORGANISM: Artificial Sequence
<220> FEATURE:
<223> OTHER INFORMATION: antisense sequence

<400> SEQUENCE: 182
aaggactcat ctcagttt                                                    18

<210> SEQ ID NO 183
<211> LENGTH: 18
<212> TYPE: DNA
<213> ORGANISM: Artificial Sequence
<220> FEATURE:
<223> OTHER INFORMATION: antisense sequence

<400> SEQUENCE: 183
taacaacgca gaagggct                                                    18

<210> SEQ ID NO 184
<211> LENGTH: 18
<212> TYPE: DNA
<213> ORGANISM: Artificial Sequence
<220> FEATURE:
<223> OTHER INFORMATION: antisense sequence

<400> SEQUENCE: 184
agtagggaag tggcataa                                                    18

<210> SEQ ID NO 185
<211> LENGTH: 18
<212> TYPE: DNA
<213> ORGANISM: Artificial Sequence
<220> FEATURE:
<223> OTHER INFORMATION: antisense sequence

<400> SEQUENCE: 185
catcaccagg taagcagc                                                    18

<210> SEQ ID NO 186
<211> LENGTH: 18
<212> TYPE: DNA
<213> ORGANISM: Artificial Sequence
<220> FEATURE:
<223> OTHER INFORMATION: antisense sequence

<400> SEQUENCE: 186
tcctgttgtg aacctatt                                                    18

<210> SEQ ID NO 187
<211> LENGTH: 18
<212> TYPE: DNA
<213> ORGANISM: Artificial Sequence
<220> FEATURE:
<223> OTHER INFORMATION: antisense sequence

<400> SEQUENCE: 187

```
ggacttgtgg gctaaaga                                             18

<210> SEQ ID NO 188
<211> LENGTH: 18
<212> TYPE: DNA
<213> ORGANISM: Artificial Sequence
<220> FEATURE:
<223> OTHER INFORMATION: antisense sequence

<400> SEQUENCE: 188
gctcaggaag acagagtg                                             18

<210> SEQ ID NO 189
<211> LENGTH: 18
<212> TYPE: DNA
<213> ORGANISM: Artificial Sequence
<220> FEATURE:
<223> OTHER INFORMATION: antisense sequence

<400> SEQUENCE: 189
tgaactccta agcaaacc                                             18

<210> SEQ ID NO 190
<211> LENGTH: 18
<212> TYPE: DNA
<213> ORGANISM: Artificial Sequence
<220> FEATURE:
<223> OTHER INFORMATION: antisense sequence

<400> SEQUENCE: 190
gatgatgaag gaactctg                                             18

<210> SEQ ID NO 191
<211> LENGTH: 20
<212> TYPE: DNA
<213> ORGANISM: Artificial Sequence
<220> FEATURE:
<223> OTHER INFORMATION: antisense sequence

<400> SEQUENCE: 191
aggccaagcc ccagctgcgg                                           20

<210> SEQ ID NO 192
<211> LENGTH: 20
<212> TYPE: DNA
<213> ORGANISM: Artificial Sequence
<220> FEATURE:
<223> OTHER INFORMATION: antisense sequence

<400> SEQUENCE: 192
cgccaccttc gctggccgcc                                           20

<210> SEQ ID NO 193
<211> LENGTH: 20
<212> TYPE: DNA
<213> ORGANISM: Artificial Sequence
<220> FEATURE:
<223> OTHER INFORMATION: antisense sequence

<400> SEQUENCE: 193
gagacgaggc tgcttggacg                                           20

<210> SEQ ID NO 194
<211> LENGTH: 20
<212> TYPE: DNA
```

<213> ORGANISM: Artificial Sequence
<220> FEATURE:
<223> OTHER INFORMATION: antisense sequence

<400> SEQUENCE: 194
ggacacagac actgcgcgcc                                          20

<210> SEQ ID NO 195
<211> LENGTH: 20
<212> TYPE: DNA
<213> ORGANISM: Artificial Sequence
<220> FEATURE:
<223> OTHER INFORMATION: antisense sequence

<400> SEQUENCE: 195
ccaaggcgct ggtagaggac                                          20

<210> SEQ ID NO 196
<211> LENGTH: 20
<212> TYPE: DNA
<213> ORGANISM: Artificial Sequence
<220> FEATURE:
<223> OTHER INFORMATION: antisense sequence

<400> SEQUENCE: 196
ttgctcgttc tagtgcgcgg                                          20

<210> SEQ ID NO 197
<211> LENGTH: 20
<212> TYPE: DNA
<213> ORGANISM: Artificial Sequence
<220> FEATURE:
<223> OTHER INFORMATION: antisense sequence

<400> SEQUENCE: 197
catagtaact tgattatcac                                          20

<210> SEQ ID NO 198
<211> LENGTH: 20
<212> TYPE: DNA
<213> ORGANISM: Artificial Sequence
<220> FEATURE:
<223> OTHER INFORMATION: antisense sequence

<400> SEQUENCE: 198
agcagactca tagtaacttg                                          20

<210> SEQ ID NO 199
<211> LENGTH: 20
<212> TYPE: DNA
<213> ORGANISM: Artificial Sequence
<220> FEATURE:
<223> OTHER INFORMATION: antisense sequence

<400> SEQUENCE: 199
acagtttagc agactcatag                                          20

<210> SEQ ID NO 200
<211> LENGTH: 20
<212> TYPE: DNA
<213> ORGANISM: Artificial Sequence
<220> FEATURE:
<223> OTHER INFORMATION: antisense sequence

<400> SEQUENCE: 200
acagcgctac aggagctggc                                          20

```
<210> SEQ ID NO 201
<211> LENGTH: 20
<212> TYPE: DNA
<213> ORGANISM: Artificial Sequence
<220> FEATURE:
<223> OTHER INFORMATION: antisense sequence

<400> SEQUENCE: 201
attgatttta tgatgcaggc                                               20

<210> SEQ ID NO 202
<211> LENGTH: 20
<212> TYPE: DNA
<213> ORGANISM: Artificial Sequence
<220> FEATURE:
<223> OTHER INFORMATION: antisense sequence

<400> SEQUENCE: 202
gtgacctgca tcccttattg                                               20

<210> SEQ ID NO 203
<211> LENGTH: 20
<212> TYPE: DNA
<213> ORGANISM: Artificial Sequence
<220> FEATURE:
<223> OTHER INFORMATION: antisense sequence

<400> SEQUENCE: 203
gtctcagttc catcttgtgc                                               20

<210> SEQ ID NO 204
<211> LENGTH: 20
<212> TYPE: DNA
<213> ORGANISM: Artificial Sequence
<220> FEATURE:
<223> OTHER INFORMATION: antisense sequence

<400> SEQUENCE: 204
agagcaaact cacaatgtgc                                               20

<210> SEQ ID NO 205
<211> LENGTH: 20
<212> TYPE: DNA
<213> ORGANISM: Artificial Sequence
<220> FEATURE:
<223> OTHER INFORMATION: antisense sequence

<400> SEQUENCE: 205
ttttggaagg gacgctggca                                               20

<210> SEQ ID NO 206
<211> LENGTH: 20
<212> TYPE: DNA
<213> ORGANISM: Artificial Sequence
<220> FEATURE:
<223> OTHER INFORMATION: antisense sequence

<400> SEQUENCE: 206
aaatgccatt gatgcagcac                                               20

<210> SEQ ID NO 207
<211> LENGTH: 20
<212> TYPE: DNA
<213> ORGANISM: Artificial Sequence
<220> FEATURE:
```

-continued

<223> OTHER INFORMATION: antisense sequence

<400> SEQUENCE: 207
attcacagat gacatttgcc 20

<210> SEQ ID NO 208
<211> LENGTH: 20
<212> TYPE: DNA
<213> ORGANISM: Artificial Sequence
<220> FEATURE:
<223> OTHER INFORMATION: antisense sequence

<400> SEQUENCE: 208
cgtgccaagt gattcctctg 20

<210> SEQ ID NO 209
<211> LENGTH: 20
<212> TYPE: DNA
<213> ORGANISM: Artificial Sequence
<220> FEATURE:
<223> OTHER INFORMATION: antisense sequence

<400> SEQUENCE: 209
ggtgttctct tgtaggtggc 20

<210> SEQ ID NO 210
<211> LENGTH: 20
<212> TYPE: DNA
<213> ORGANISM: Artificial Sequence
<220> FEATURE:
<223> OTHER INFORMATION: antisense sequence

<400> SEQUENCE: 210
ggccaacatt ctcatgtgtg 20

<210> SEQ ID NO 211
<211> LENGTH: 20
<212> TYPE: DNA
<213> ORGANISM: Artificial Sequence
<220> FEATURE:
<223> OTHER INFORMATION: antisense sequence

<400> SEQUENCE: 211
cgctcaaact atgaacagcc 20

<210> SEQ ID NO 212
<211> LENGTH: 20
<212> TYPE: DNA
<213> ORGANISM: Artificial Sequence
<220> FEATURE:
<223> OTHER INFORMATION: antisense sequence

<400> SEQUENCE: 212
aggcgaccct ctaactggtg 20

<210> SEQ ID NO 213
<211> LENGTH: 20
<212> TYPE: DNA
<213> ORGANISM: Artificial Sequence
<220> FEATURE:
<223> OTHER INFORMATION: antisense sequence

<400> SEQUENCE: 213
ccattttagc agtcagctcc 20

```
<210> SEQ ID NO 214
<211> LENGTH: 20
<212> TYPE: DNA
<213> ORGANISM: Artificial Sequence
<220> FEATURE:
<223> OTHER INFORMATION: antisense sequence

<400> SEQUENCE: 214
cgaatggttc gtttgagctc                                              20

<210> SEQ ID NO 215
<211> LENGTH: 20
<212> TYPE: DNA
<213> ORGANISM: Artificial Sequence
<220> FEATURE:
<223> OTHER INFORMATION: antisense sequence

<400> SEQUENCE: 215
ccattgcact gctgtgcttc                                              20

<210> SEQ ID NO 216
<211> LENGTH: 20
<212> TYPE: DNA
<213> ORGANISM: Artificial Sequence
<220> FEATURE:
<223> OTHER INFORMATION: antisense sequence

<400> SEQUENCE: 216
gcagtcggta actgaaggtg                                              20

<210> SEQ ID NO 217
<211> LENGTH: 20
<212> TYPE: DNA
<213> ORGANISM: Artificial Sequence
<220> FEATURE:
<223> OTHER INFORMATION: antisense sequence

<400> SEQUENCE: 217
gccttacagg tgcttcagac                                              20

<210> SEQ ID NO 218
<211> LENGTH: 20
<212> TYPE: DNA
<213> ORGANISM: Artificial Sequence
<220> FEATURE:
<223> OTHER INFORMATION: antisense sequence

<400> SEQUENCE: 218
agcaagcagc tctggtttgg                                              20

<210> SEQ ID NO 219
<211> LENGTH: 20
<212> TYPE: DNA
<213> ORGANISM: Artificial Sequence
<220> FEATURE:
<223> OTHER INFORMATION: antisense sequence

<400> SEQUENCE: 219
ggctacccat gtcaaagcgg                                              20

<210> SEQ ID NO 220
<211> LENGTH: 20
<212> TYPE: DNA
<213> ORGANISM: Artificial Sequence
<220> FEATURE:
<223> OTHER INFORMATION: antisense sequence
```

```
<400> SEQUENCE: 220 ttgttttga gcaagtgagg                                                    20

<210> SEQ ID NO 221
<211> LENGTH: 20
<212> TYPE: DNA
<213> ORGANISM: Artificial Sequence
<220> FEATURE:
<223> OTHER INFORMATION: antisense sequence

<400> SEQUENCE: 221
ggcactgttt tctccaggta                                                   20

<210> SEQ ID NO 222
<211> LENGTH: 20
<212> TYPE: DNA
<213> ORGANISM: Artificial Sequence
<220> FEATURE:
<223> OTHER INFORMATION: antisense sequence

<400> SEQUENCE: 222
acatatttcc cgtggcttgt                                                   20

<210> SEQ ID NO 223
<211> LENGTH: 20
<212> TYPE: DNA
<213> ORGANISM: Artificial Sequence
<220> FEATURE:
<223> OTHER INFORMATION: antisense sequence

<400> SEQUENCE: 223
ggaacgtgtg gattcccagg                                                   20

<210> SEQ ID NO 224
<211> LENGTH: 20
<212> TYPE: DNA
<213> ORGANISM: Artificial Sequence
<220> FEATURE:
<223> OTHER INFORMATION: antisense sequence

<400> SEQUENCE: 224
tgctgcaaca tgccacaggc                                                   20

<210> SEQ ID NO 225
<211> LENGTH: 20
<212> TYPE: DNA
<213> ORGANISM: Artificial Sequence
<220> FEATURE:
<223> OTHER INFORMATION: antisense sequence

<400> SEQUENCE: 225
atacaccaga gcaaaagccc                                                   20

<210> SEQ ID NO 226
<211> LENGTH: 20
<212> TYPE: DNA
<213> ORGANISM: Artificial Sequence
<220> FEATURE:
<223> OTHER INFORMATION: control sequence

<400> SEQUENCE: 226
aaaagactga acttttaagg                                                   20

<210> SEQ ID NO 227
<211> LENGTH: 20
```

```
<212> TYPE: DNA
<213> ORGANISM: Artificial Sequence
<220> FEATURE:
<223> OTHER INFORMATION: control sequence

<400> SEQUENCE: 227
acttaattac catgactagt                                               20

<210> SEQ ID NO 228
<211> LENGTH: 20
<212> TYPE: DNA
<213> ORGANISM: Artificial Sequence
<220> FEATURE:
<223> OTHER INFORMATION: control sequence

<400> SEQUENCE: 228
ccacgaggag caccatcaag                                               20
```